(12) United States Patent
Vankayalapati

(10) Patent No.: US 11,053,221 B2
(45) Date of Patent: Jul. 6, 2021

(54) SUBSTITUTED PYRIMIDINES FOR INHIBITING EMBRYONIC LEUCINE ZIPPER KINASE ACTIVITY

(71) Applicant: Arrien Pharmaceuticals LLC, Salt Lake City, UT (US)

(72) Inventor: Hariprasad Vankayalapati, Salt Lake City, UT (US)

(73) Assignee: ARRIEN PHARMACEUTICALS LLC, Salt Lake City, UT (US)

( * ) Notice: Subject to any disclaimer, the term of this patent is extended or adjusted under 35 U.S.C. 154(b) by 0 days.

(21) Appl. No.: 16/664,649

(22) Filed: Oct. 25, 2019

(65) Prior Publication Data
US 2020/0131154 A1  Apr. 30, 2020

Related U.S. Application Data

(60) Provisional application No. 62/751,405, filed on Oct. 26, 2018.

(51) Int. Cl.
| | |
|---|---|
| A61K 31/506 | (2006.01) |
| C07D 239/24 | (2006.01) |
| C07D 403/04 | (2006.01) |
| A61P 35/02 | (2006.01) |
| C07D 401/14 | (2006.01) |

(52) U.S. Cl.
CPC ............ C07D 403/04 (2013.01); A61P 35/02 (2018.01); C07D 401/14 (2013.01)

(58) Field of Classification Search
CPC .......................... A61K 31/506; C07D 239/24
USPC ........................................... 514/256; 544/333
See application file for complete search history.

(56) References Cited

FOREIGN PATENT DOCUMENTS

WO    WO 20/087024    * 4/2020

OTHER PUBLICATIONS

Jordan, V. C. Nature Reviews: Drug Discovery, 2, 2003, 205.*
Dörwald, F. Zaragoza. Side Reactions in Organic Synthesis: A Guide to Successful Synthesis Design, Weinheim: Wiley-VCH Verlag GmbH & Co. KGaA, 2005, Preface.*
Wolff, Manfred E., Ed. Burger's Medicinal Chemistry and Drug Discovery—Fifth Edition, vol. 1: Principles and Practice, New York: John Wiley & Sons, 1994, 975-977.*
Hackam, et al. JAMA, 296(14), 2006, 1731-1732.*

* cited by examiner

*Primary Examiner* — Douglas M Willis
(74) *Attorney, Agent, or Firm* — Seed IP Law Group LLP

(57) ABSTRACT

Compounds having activity as chemotherapeutic agents are provided. The compounds have the following structure (I):

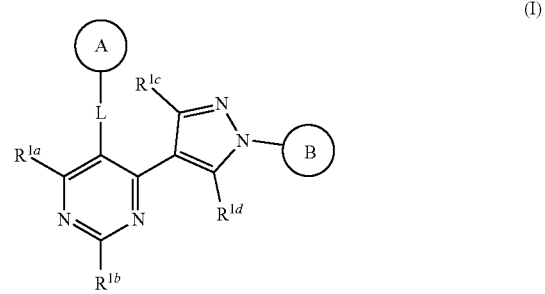

or a pharmaceutically acceptable salt, stereoisomer, isotopic form or prodrug thereof, wherein $R^{1a}$, $R^{1b}$, $R^{1c}$, $R^{1d}$, L,

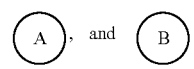

and are as defined herein. Methods associated with preparation and use of such compounds, pharmaceutical compositions comprising such compounds and methods for treating cancer (e.g., hematological cancers) are also provided.

22 Claims, No Drawings

SUBSTITUTED PYRIMIDINES FOR INHIBITING EMBRYONIC LEUCINE ZIPPER KINASE ACTIVITY

BACKGROUND

Technical Field

The present disclosure is generally directed to novel compounds and methods for their preparation and use as therapeutic or prophylactic agents, for example for treatment of cancer (e.g., hematological cancer).

Description of the Related Art

Cancer is a group of diseases involving abnormal cell growth with a potential to spread to various parts of the body. There are hundreds of types of cancers that affect humans. Millions of people are diagnosed with cancers with millions more being diagnosed every year. The most common types of cancers include lung cancer, breast cancers, prostate cancers, colorectal cancers, among others. Treatment for cancers includes surgery, radiation therapy, chemotherapy, immunotherapy, hormone therapy, stem cell replacement, and others. Treatment options can be invasive and have a variety of undesirable side effects. Chemotherapy is a common type of cancer treatment, and although it can be effective, chemotherapy can have intense side effects.

Accordingly, while progress has been made in this field, there remains a need in the art for improved compounds and methods for treatment of cancer, for example hematological cancers. The present disclosure fulfills this need and provides further related advantages.

BRIEF SUMMARY

In brief, embodiments of the present disclosure provide compounds, including pharmaceutically acceptable salts, isotopic forms, stereoisomers and prodrugs thereof. Methods for use of such compounds for treatment of various diseases or conditions, such as cancer (e.g., hematological cancer), are also provided.

In one embodiment, compounds having the following structure (I) are provided:

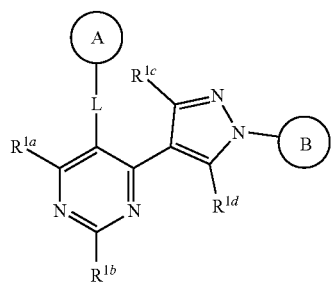

(I)

or a pharmaceutically acceptable salt stereoisomer, isotopic form or prodrug thereof, wherein $R^{1a}$, $R^{1b}$, $R^{1c}$, $R^{1d}$, L, and are as defined herein. Pharmaceutical compositions comprising one or more compounds of structure (I) and a pharmaceutically acceptable carrier are also provided in various other embodiments.

In other embodiments, the present disclosure provides a method for treatment of cancer (e.g., hematological cancers), the method comprising administering an effective amount of a pharmaceutical composition comprising any one or more of the compounds of structure (I) to a subject in need thereof.

These and other aspects of the disclosure will be apparent upon reference to the following detailed description.

DETAILED DESCRIPTION

In the following description, certain specific details are set forth in order to provide a thorough understanding of various embodiments of the disclosure. However, one skilled in the art will understand that the disclosure may be practiced without these details.

Unless the context requires otherwise, throughout the present specification and claims, the word "comprise" and variations thereof, such as, "comprises" and "comprising" are to be construed in an open, inclusive sense, that is, as "including, but not limited to".

In the present description, any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size, or thickness, are to be understood to include any integer within the recited range, unless otherwise indicated. As used herein, the terms "about" and "approximately" mean 20%, +10%, 5% or 1% of the indicated range, value, or structure, unless otherwise indicated. It should be understood that the terms "a" and "an" as used herein refer to "one or more" of the enumerated components. The use of the alternative (e.g., "or") should be understood to mean either one, both, or any combination thereof of the alternatives.

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Unless defined otherwise, all technical and scientific terms used herein have the same meaning as is commonly understood by one of skill in the art to which this disclosure belongs. As used in the specification and claims, the singular form "a", "an" and "the" include plural references unless the context clearly dictates otherwise.

"Amino" refers to the —NH$_2$ radical.
"Carboxy" or "carboxyl" refers to the —CO$_2$H radical.
"Cyano" refers to the —CN radical.
"Hydroxy" or "hydroxyl" refers to the —OH radical.
"Oxo" refers to the =O substituent.
"Alkyl" refers to a saturated, straight or branched hydrocarbon chain radical consisting solely of carbon and hydrogen atoms, having from one to twelve carbon atoms (C$_1$-C$_{12}$ alkyl), preferably one to eight carbon atoms (C$_1$-C$_8$ alkyl) or one to six carbon atoms (C$_1$-C$_6$ alkyl), and which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl and the like. Unless stated otherwise specifically in the specification, an alkyl group is optionally substituted.

"Alkenyl" refers to an unsaturated, straight or branched hydrocarbon chain radical consisting solely of carbon and hydrogen atoms, which contains one or more carbon-carbon double bonds), having from two to twelve carbon atoms ($C_2$-$C_{12}$ alkenyl), preferably two to eight carbon atoms ($C_2$-$C_8$ alkenyl) or two to six carbon atoms ($C_2$-$C_6$ alkenyl), and which is attached to the rest of the molecule by a single bond, e.g., ethenyl, prop-1-enyl, but-1-enyl, pent-1-enyl, penta-1,4-dienyl, and the like. Unless stated otherwise specifically in the specification, an alkenyl group is optionally substituted.

"Alkynyl" refers to an unsaturated, straight or branched hydrocarbon chain radical consisting solely of carbon and hydrogen atoms, which contains one or more carbon-carbon triple bonds), having from two to twelve carbon atoms ($C_2$-$C_{12}$ alkynyl), preferably two to eight carbon atoms ($C_2$-$C_8$ alkynyl) or two to six carbon atoms ($C_2$-$C_6$ alkynyl), and which is attached to the rest of the molecule by a single bond, e.g., ethynyl, propynyl, butynyl, pentynyl, hexynyl, and the like. Unless stated otherwise specifically in the specification, an alkynyl group is optionally substituted.

"Alkylene" or "alkylene chain" refers to a straight or branched divalent hydrocarbon chain linking the rest of the molecule to a radical group, consisting solely of carbon and hydrogen, which is saturated or unsaturated (i.e., contains one or more double bonds or an "alkenylene" and/or triple bonds or an "alkynylene"), and having from one to twelve carbon atoms, e.g., methylene, ethylene, propylene, n-butylene, ethenylene, propenylene, n-butenylene, propynylene, n-butynylene, and the like. The alkylene chain is attached to the rest of the molecule through a single or double bond and to the radical group through a single or double bond. The points of attachment of the alkylene chain to the rest of the molecule and to the radical group can be through one carbon or any two carbons within the chain. Unless stated otherwise specifically in the specification, an alkylene chain is optionally substituted.

"Alkoxy" refers to a radical of the formula —$OR_a$ where $R_a$ is an alkyl radical as defined above containing one to twelve carbon atoms. Unless stated otherwise specifically in the specification, an alkoxy group is optionally substituted.

"Alkylaminyl" refers to a radical of the formula —$NHR_a$ or —$NR_aR_a$ where each $R_a$ is, independently, an alkyl radical as defined above containing one to twelve carbon atoms. Unless stated specifically otherwise, an alkylaminyl is optionally substituted.

"Aminoalkyl" refers to an alkyl group comprising at least one amino substituent. The amino substituent can be on a tertiary, secondary or primary carbon. Unless stated specifically otherwise, an aminoalkyl is optionally substituted.

"Alkylaminylalkyl" refers to an alkyl group comprising at least one alkylaminyl substituent. The alkylaminyl substituent can be on a tertiary, secondary or primary carbon. Unless stated otherwise specifically in the specification, an alkylaminylalkyl group is optionally substituted.

"Alkylsulfonyl" refers to a radical of the formula —$S(O)_2R_a$ where $R_a$ is an alkyl radical as defined above containing one to twelve carbon atoms. Unless stated specifically otherwise, an alkylsulfonyl is optionally substituted.

"Aromatic ring" refers to a cyclic planar portion of a molecule (i.e., a radical) with a ring of resonance bonds that exhibits increased stability relative to other connective arrangements with the same sets of atoms. Generally, aromatic rings contains a set of covalently bound co-planar atoms and comprises a number of R-electrons (for example, alternating double and single bonds) that is even but not a multiple of 4 (i.e., 4n+2 π-electrons, where n=0, 1, 2, 3, etc.). Aromatic rings include, but are not limited to, phenyl, naphthenyl, imidazolyl, pyrrolyl, pyridinyl, pyrimidinyl, pyrazinyl, pyridonyl, pyridazinyl, pyrimidonyl. Unless stated otherwise specifically in the specification, an "aromatic ring" includes all radicals that are optionally substituted.

"Aryl" refers to a carbocyclic ring system radical comprising 6 to 18 carbon ring atoms and at least one aromatic ring. For purposes of embodiments of this invention, the aryl radical is a monocyclic, bicyclic, tricyclic or tetracyclic ring system, which may include fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" or the prefix "ar-" (such as in "aralkyl") is meant to include aryl radicals that are optionally substituted.

"Carbocyclic" or "carbocycle" refers to a ring system, wherein each of the ring atoms are carbon.

"Cycloalkyl" refers to a stable non-aromatic monocyclic or polycyclic carbocyclic radical, which may include fused or bridged ring systems, having from three to fifteen carbon atoms, preferably having from three to ten carbon atoms, and which is saturated or unsaturated and attached to the rest of the molecule by a single bond. Monocyclic radicals include, for example, cyclopropyl, cyclobutyl, cyclopentyl, cyclohexyl, cycloheptyl, and cyclooctyl. Polycyclic radicals include, for example, adamantyl, norbornyl, decalinyl, 7,7-dimethyl-bicyclo[2.2.1]heptanyl, and the like. Unless otherwise stated specifically in the specification, a cycloalkyl group is optionally substituted.

"Fused" refers to any ring structure described herein which is fused to an existing ring structure in the compounds of the invention. When the fused ring is a heterocyclyl ring or a heteroaryl ring, any carbon atom on the existing ring structure which becomes part of the fused heterocyclyl ring or the fused heteroaryl ring can be replaced with a nitrogen atom.

"Halo" or "halogen" refers to bromo, chloro, fluoro or iodo.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like. A "perhaloalkyl" is an alkyl radical, as defined above, wherein each H atom is replaced with a halogen. Unless stated otherwise specifically in the specification, a haloalkyl group is optionally substituted.

"Haloalkoxy" refers to a radical of the formula —$OR_a$ where $R_a$ is a haloalkyl radical as defined herein containing one to twelve carbon atoms. Unless stated otherwise specifically in the specification, a haloalkoxy group is optionally substituted.

"Heteroalkylene" or "heteroalkylene chain" refers to a straight or branched divalent chain linking the rest of the molecule to a radical group, consisting of carbon, hydrogen and at least one heteroatom within the chain linkage (e.g., oxygen, nitrogen, sulfur, phosphorus, etc.), which is saturated or unsaturated (i.e., contains one or more double and/or triple bonds). The heteroalkylene chain is attached to the rest of the molecule through a single or double bond and to the radical group through a single or double bond. The points of attachment of the heteroalkylene chain to the rest of the molecule and to the radical group can be through one carbon, any two carbons, one heteroatom, or any two heteroatoms within the chain. Unless stated otherwise specifically in the specification, a heteroalkylene chain is optionally substituted.

"Heteroatomic" or "heteroatomic chain" refers to a straight or branched divalent chain linking the rest of the molecule to a radical group, consisting solely of atoms other than carbon and hydrogen within the chain linkage (e.g., oxygen, nitrogen, sulfur, phosphorus, etc.), which is saturated or unsaturated (i.e., contains one or more double and/or triple bonds). The heteroatomic chain is attached to the rest of the molecule through a single or double bond and to the radical group through a single or double bond. The points of attachment of the heteroatomic chain to the rest of the molecule and to the radical group can be through one heteroatom or any two heteroatoms within the chain. Unless stated otherwise specifically in the specification, a heteroatomic chain is optionally substituted.

"Heterocyclyl" or "heterocyclic ring" refers to a stable 3- to 18-membered non-aromatic ring radical having one to twelve ring carbon atoms (e.g., two to twelve) and from one to six ring heteroatoms selected from the group consisting of nitrogen, oxygen and sulfur. Unless stated otherwise specifically in the specification, the heterocyclyl radical is a monocyclic, bicyclic, tricyclic or tetracyclic ring system, which may include fused, spirocyclic ("spiro-heterocyclyl") and/or bridged ring systems; and the nitrogen, carbon or sulfur atoms in the heterocyclyl radical is optionally oxidized; the nitrogen atom is optionally quaternized; and the heterocyclyl radical is partially or fully saturated. Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,2,3,4-tetrahydroquinolinyl, and 1,1-dioxo-thiomorpholinyl. Unless stated otherwise specifically in the specification, a heterocyclyl group is optionally substituted.

The term "substituted" as used herein means any of the above groups (e.g., alkyl, alkenyl, alkynyl, alkylene, alkoxy, alkylaminyl, aminoalkyl, alkylaminylalkyl, alkylsulfonyl, aryl, cycloalkyl, haloalkyl, haloalkoxy, heteroalkylene and/or heterocyclyl) wherein at least one hydrogen atom (e.g., 1, 2, 3 or all hydrogen atoms) is replaced by a bond to a non-hydrogen atom such as, but not limited to: a halogen atom such as F, Cl, Br, and I; cyano, an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —NR$_g$R$_h$, —NR$_g$C(=O)R$_h$, —NR$_g$C(=O)NR$_g$R$_h$, —NR$_g$C(=O)OR$_h$, —NR$_g$SO$_2$R$_h$, —OC(=O)NR$_g$R$_h$, —OR$_g$, —SR$_g$, —SOR$_g$, —SO$_2$R$_g$, —OSO$_2$R$_g$, —SO$_2$OR$_g$, =NSO$_2$R$_g$, and —SO$_2$NR$_g$R$_h$. "Substituted" also means any of the above groups in which one or more hydrogen atoms are replaced with —C(=O)R$_g$, —C(=O)OR$_g$, —C(=O)NR$_g$R$_h$, —CH$_2$SO$_2$R$_g$, —CH$_2$SO$_2$NR$_g$R$_h$. In the foregoing, R$_g$ and R$_h$ are the same or different and independently hydrogen, optionally substituted alkyl, optionally substituted alkoxy, optionally substituted alkylaminyl, optionally substituted aryl, optionally substituted cycloalkyl, optionally substituted haloalkyl, or optionally substituted heterocyclyl. "Substituted" further means any of the above groups in which one or more hydrogen atoms are replaced by a bond to an amino, cyano, hydroxyl, oxo (=O), halo or optionally substituted: alkyl, alkoxy, alkylaminyl, aryl, cycloalkyl, haloalkyl and/or heterocyclyl, group. In addition, each of the foregoing substituents may also be optionally substituted with one or more of the above substituents.

It is understood that each choice for $R^{1a}$, $R^{1b}$, $R^{1c}$, $R^{1d}$, L,

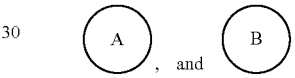

is optionally substituted as described above unless specifically stated otherwise, and provided that all valences are satisfied by the substitution. Specifically, each choice for $R^{1a}$, $R^{1b}$, $R^{1c}$, $R^{1d}$, L,

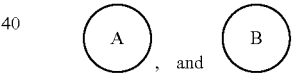

and is optionally substituted unless specifically stated otherwise, and provided such substitution results in a stable molecule (e.g., groups such as H and halo are not optionally substituted).

The term "effective amount" or "therapeutically effective amount" refers to that amount of a compound described herein that is sufficient to effect the intended application including but not limited to disease treatment, as defined below. The therapeutically effective amount may vary depending upon the intended treatment application (in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g., reduction of platelet adhesion and/or cell migration. The specific dose will vary depending on the particular compounds chosen, the dosing regimen to be followed, whether it is administered in combination with other compounds, timing of administration, the tissue to which it is administered, and the physical delivery system in which it is carried.

As used herein, "treatment" or "treating" refer to an approach for obtaining beneficial or desired results with respect to a disease, disorder or medical condition including but not limited to a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the subject, notwithstanding that the subject may still be afflicted with the underlying disorder. In certain embodiments, for prophylactic benefit, the compositions are administered to a subject at risk of developing a particular disease, or to a subject reporting one or more of the physiological symptoms of a disease, even though a diagnosis of this disease may not have been made.

A "therapeutic effect," as that term is used herein, encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

The term "co-administration," "administered in combination with," and their grammatical equivalents, as used herein, encompass administration of two or more agents to an animal, including humans, so that both agents and/or their metabolites are present in the subject at the same time. Co-administration includes simultaneous administration in separate compositions, administration at different times in separate compositions, or administration in a composition in which both agents are present.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

In some embodiments, pharmaceutically acceptable salts include quaternary ammonium salts such as quaternary amine alkyl halide salts (e.g., methyl bromide).

The term "inhibitor" refers to a compound having the ability to inhibit a biological function of a target protein, whether by inhibiting the activity or expression of the protein. A preferred biological activity inhibited by a compound is associated with the development, growth, or spread of a tumor.

An "anti-cancer agent," "anti-tumor agent" or "chemotherapeutic agent" refers to any agent useful in the treatment of a neoplastic condition. One class of anti-cancer agents comprises chemotherapeutic agents. "Chemotherapy" means the administration of one or more chemotherapeutic drugs and/or other agents to a cancer patient by various methods, including intravenous, oral, intramuscular, intraperitoneal, intravesical, subcutaneous, transdermal, buccal, or inhalation or in the form of a suppository.

The term "selective inhibition" or "selectively inhibit" refers to a biologically active agent's ability to preferentially reduce the target signaling activity as compared to off-target signaling activity, via direct or indirect interaction with the target.

"Subject" refers to an animal, such as a mammal, for example a human. The methods described herein can be useful in both human therapeutics and veterinary applications. In some embodiments, the subject is a mammal, and in some embodiments, the subject is human.

"Mammal" includes humans and both domestic animals such as laboratory animals and household pets (e.g., cats, dogs, swine, cattle, sheep, goats, horses, rabbits), and non-domestic animals such as wildlife and the like.

"Radiation therapy" means exposing a subject, using routine methods and compositions known to the practitioner, to radiation emitters such as alpha-particle emitting radionuclides (e.g., actinium and thorium radionuclides), low linear energy transfer (LET) radiation emitters (i.e., beta emitters), conversion electron emitters (e.g., strontium-89 and samarium-153-EDTMP, or high-energy radiation, including without limitation x-rays, gamma rays, and neutrons.

Prodrugs of the disclosed compounds are included in various embodiments. "Prodrug" is meant to indicate a compound that may be converted under physiological conditions or by solvolysis to a biologically active compound described herein (e.g., compound of structure (I)). Thus, the term "prodrug" refers to a precursor of a biologically active compound that is pharmaceutically acceptable. In some aspects, a prodrug is inactive when administered to a subject, but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam). A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein. The term "prodrug" is also meant to include any covalently bonded carriers, which release the active compound in vivo when such prodrug is administered to a mammalian subject. Prodrugs of an active compound, as described herein, are typically prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of a hydroxy functional group, or acetamide, formamide and benzamide derivatives of an amine functional group in the active compound and the like.

The term "in vivo" refers to an event that takes place in a subject's body.

Embodiments disclosed herein are also meant to encompass all pharmaceutically acceptable compounds of structure (I) being isotopically-labelled by having one or more atoms replaced by an atom having a different atomic mass or mass number (i.e., an "isotopic form" of a compound of structure (I)). Examples of isotopes that can be incorporated into the disclosed compounds include isotopes of hydrogen, carbon, nitrogen, oxygen, phosphorous, fluorine, chlorine, and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. These radiolabeled compounds could be useful to help determine or measure the effectiveness of the compounds, by characterizing, for example, the site or mode of action, or binding affinity to pharmacologically important site of action. Certain isotopically-labeled compounds of structure (I), for example, those incorporating a radioactive isotope, are useful in drug and/or substrate tissue distribution studies. The radioactive isotopes tritium, i.e. $^{3}H$, and carbon-14, i.e. $^{14}C$, are particularly useful for this purpose in view of their ease of incorporation and ready means of detection.

Substitution with heavier isotopes such as deuterium, i.e., $^{2}H$, may afford certain therapeutic advantages resulting from greater metabolic stability, for example, increased in vivo half-life or reduced dosage requirements, and hence are preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds of structure (I) can generally be prepared by conventional techniques known to those skilled in the art or by processes analogous to those described in the Examples as set out below using an appropriate isotopically-labeled reagent in place of the non-labeled reagent previously employed.

Certain embodiments are also meant to encompass the in vivo metabolic products of the disclosed compounds. Such products may result from, for example, the oxidation, reduction, hydrolysis, amidation, esterification, and the like of the administered compound, primarily due to enzymatic processes. Accordingly, the embodiments include compounds produced by a process comprising administering a compound of this disclosure to a mammal for a period of time sufficient to yield a metabolic product thereof. Such products are typically identified by administering a radiolabeled compound of the disclosure in a detectable dose to an animal, such as rat, mouse, guinea pig, monkey, or to human, allowing sufficient time for metabolism to occur, and isolating its conversion products from the urine, blood or other biological samples.

"Stable compound" and "stable structure" are meant to indicate a compound that is sufficiently robust to survive isolation to a useful degree of purity from a reaction mixture, and formulation into an efficacious therapeutic agent.

Often crystallizations produce a solvate of the compound of the invention. As used herein, the term "solvate" refers to an aggregate that comprises one or more molecules of a compound of the disclosure with one or more molecules of solvent. In some embodiments, the solvent is water, in which case the solvate is a hydrate. Alternatively, in other embodiments, the solvent is an organic solvent. Thus, the compounds of the present disclosure may exist as a hydrate, including a monohydrate, dihydrate, hemihydrate, sesquihydrate, trihydrate, tetrahydrate and the like, as well as the corresponding solvated forms. In some aspects, the compound of the disclosure is a true solvate, while in other cases, the compound of the disclosure merely retains adventitious water or is a mixture of water plus some adventitious solvent.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

A "pharmaceutical composition" refers to a formulation of a compound of the disclosure and a medium generally accepted in the art for the delivery of the biologically active compound to mammals, e.g., humans. Such a medium includes all pharmaceutically acceptable carriers, diluents or excipients therefor.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

The compounds of the disclosure (i.e., compounds of structure (I) and embodiments thereof), or their pharmaceutically acceptable salts may contain one or more centers of geometric asymmetry and may thus give rise to enantiomers, diastereomers, and other stereoisomeric forms that are defined, in terms of absolute stereochemistry, as (R)- or (S)- or, as (D)- or (L)- for amino acids. Embodiments thus include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included.

Embodiments of the present disclosure include all manner of rotamers and conformationally restricted states of a compound of the invention. Atropisomers, which are stereoisomers arising because of hindered rotation about a single bond, where energy differences due to steric strain or other contributors create a barrier to rotation that is high enough to allow for isolation of individual conformers, are also included. As an example, certain compounds of the disclosure may exist as mixtures of atropisomers or purified or enriched for the presence of one atropisomer.

A "stereoisomer" refers to a compound made up of the same atoms bonded by the same bonds but having different three-dimensional structures, which are not interchangeable. The present disclosure contemplates various stereoisomers and mixtures thereof and includes "enantiomers", which refers to two stereoisomers whose molecules are non-superimposable mirror images of one another.

A "tautomer" refers to a proton shift from one atom of a molecule to another atom of the same molecule. Embodiments thus include tautomers of the disclosed compounds.

The chemical naming protocol and structure diagrams used herein are a modified form of the I.U.P.A.C. nomenclature system, using the ACD/Name Version 9.07 software program and/or ChemDraw software naming program (CambridgeSoft). For complex chemical names employed herein, a substituent group is typically named before the group to which it attaches. For example, cyclopropylethyl comprises an ethyl backbone with a cyclopropyl substituent. Except as described below, all bonds are identified in the chemical structure diagrams herein, except for all bonds on some carbon atoms, which are assumed to be bonded to sufficient hydrogen atoms to complete the valency.

Compounds

In an aspect, the disclosure provides compounds that are useful as chemotherapeutic agents. In one particular embodiment, the disclosure provides a compound having the following structure (I):

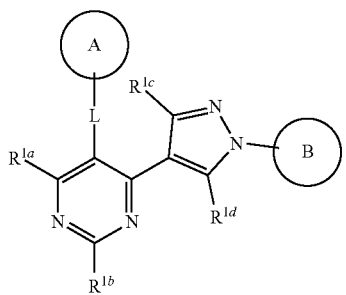

(I)

or a pharmaceutically acceptable salt, isotopic form, stereoisomer or prodrug thereof, wherein:

A is optionally substituted cycloalkyl or optionally substituted heterocyclyl;

is optionally substituted aryl;

L is a direct bond or a heteroatomic, heteroalkylene or alkylene linker; and $R^{1a}$, $R^{1b}$, $R^{1c}$ and $R^{1d}$ are each independently H, halo, $C_1$-$C_6$ alkyl, $C_2$-$C_6$ alkenyl or $C_2$-$C_6$ alkynyl.

In some more specific embodiments, $R^{1a}$, $R^{1b}$, $R^{1c}$ and $R^{1d}$ are each independently H or halo. In some specific embodiments, $R^{1c}$ and $R^{1d}$ are each H. In some embodiments, $R^{1a}$ is halo, for example, $R^{1a}$ is chloro. In some more specific embodiments, $R^{1b}$ is H. In some embodiments, $R^{1a}$ and $R^{1b}$ are each H.

In some embodiments, L is a direct bond. In some other embodiments, L is a heteroalkylene linker, for example, a heteroalkylene linker having one of the following structures:

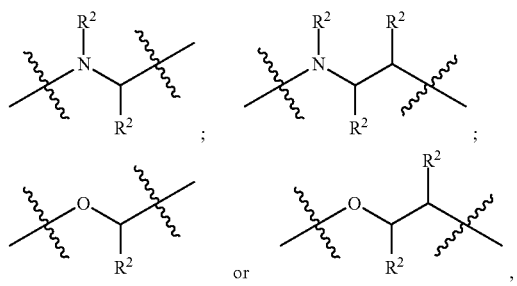

wherein $R^2$ is, at each occurrence, independently H or $C_1$-$C_6$ alkyl.

In some more specific embodiments, $R^2$ is, at each occurrence, independently H or methyl.

In some specific embodiments, the compound of structure (I) has one of the following structures (Ia), (Ib), (Ic), or (Id):

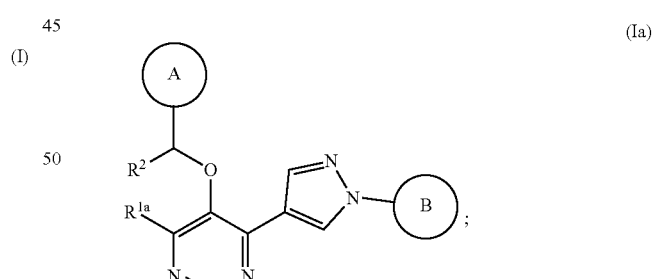

(Ia)

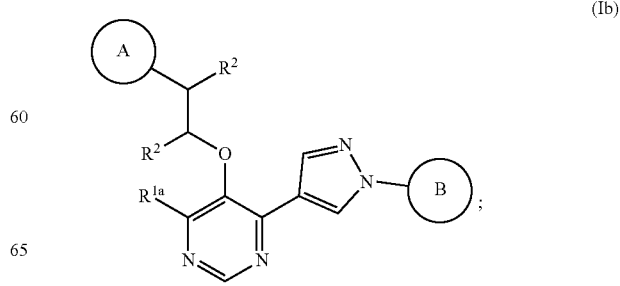

(Ib)

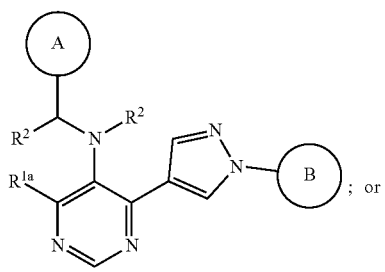
(Ic)
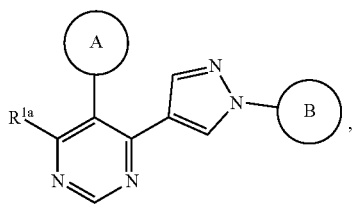
(Id)
wherein:
R¹ is H or halo; and
R² is H or methyl.
In certain specific embodiments, the compound has one of the following structures (Ia'), (Ia"), (Ib'), (Ib"), (Ic'), (Ic"), (Id') or (Id"):
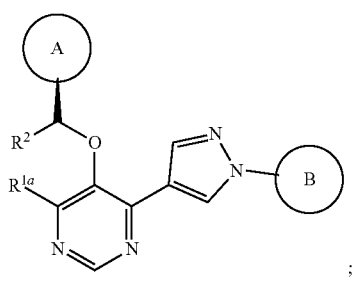
(Ia')
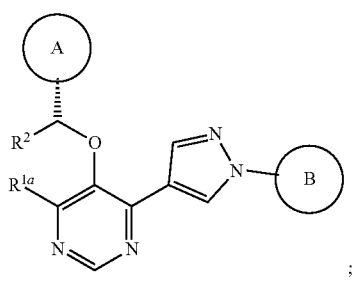
(Ia")
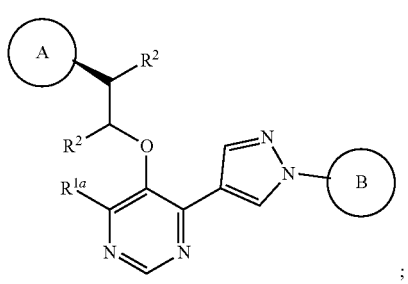
(Ib')
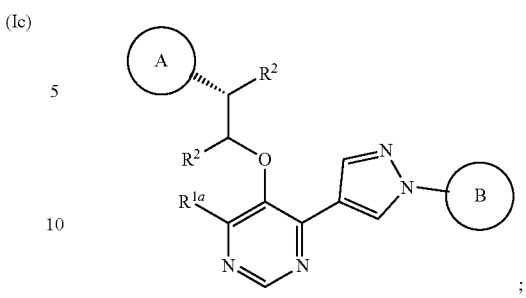
(Ib")
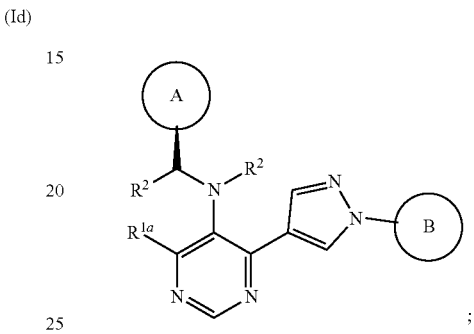
(Ic')
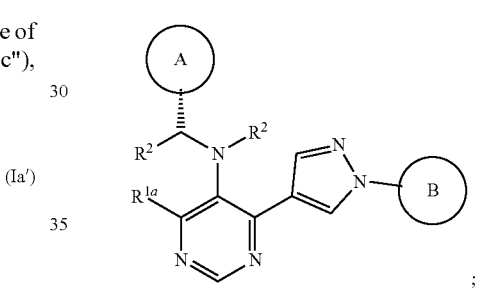
(Ic")
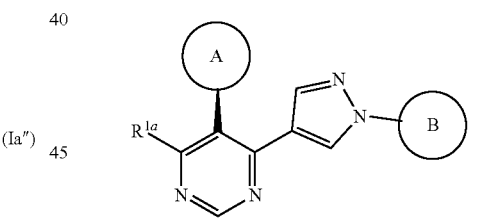
(Id')
or
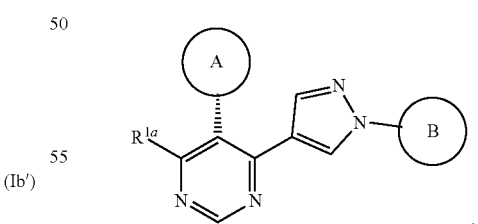
(Id")
In certain embodiments of the compound of structure (I),
(A)

is cycloalkyl. For example, in some specific embodiments,

is cyclobutyl, cyclopentyl or cyclohexyl.

In other embodiments,

is heterocyclyl. For example, in some embodiments,

is piperidinyl.

As disclosed above,

is optionally substituted. Accordingly, in some embodiments,

is substituted. In certain more specific embodiments,

is substituted with at least one substituent selected from $C_1$-$C_6$ alkyl, hydroxyl, amino, alkylaminyl, aminoalkyl, alkylaminylalkyl or combinations thereof. In certain other embodiments,

is unsubstituted. In some specific embodiments,

has one of the following structures:

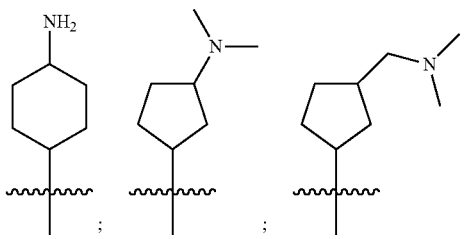

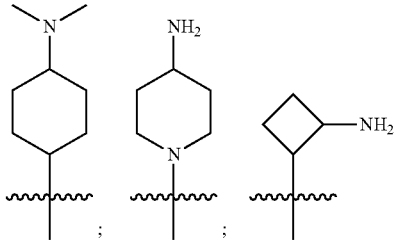

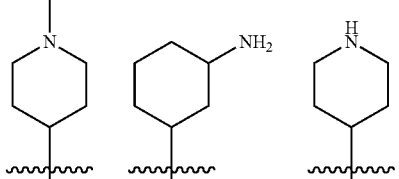

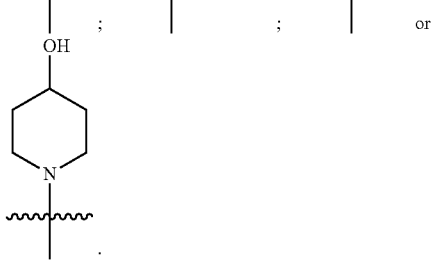

In some particular embodiments,

has one of the following structures:

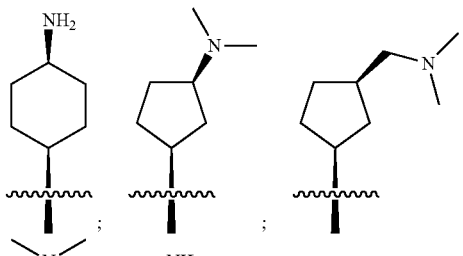

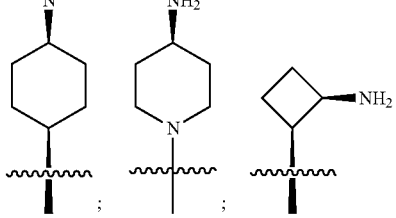

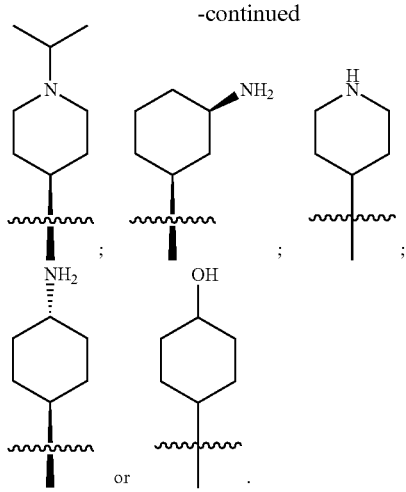

In certain embodiments, (B)

is phenyl. In some embodiments, (B)

is substituted. In some specific embodiments, (B)

is substituted with at least one substituent selected from $C_1$-$C_6$ alkyl, halo, haloalkyl, haloalkoxy, cyano, alkoxy, hydroxyl, alkylsulfonyl and heterocyclyl. In some more specific embodiments, (B)

is substituted with at least one substituent selected from methyl, fluoro, cyano, methoxy, hydroxyl, trifluoromethoxy, ethylsulfonyl, morpholinyl and N-methylpiperazinyl. In certain other embodiments, (B)

is unsubstituted.

In some specific embodiments, (B)

has one of the following structures:

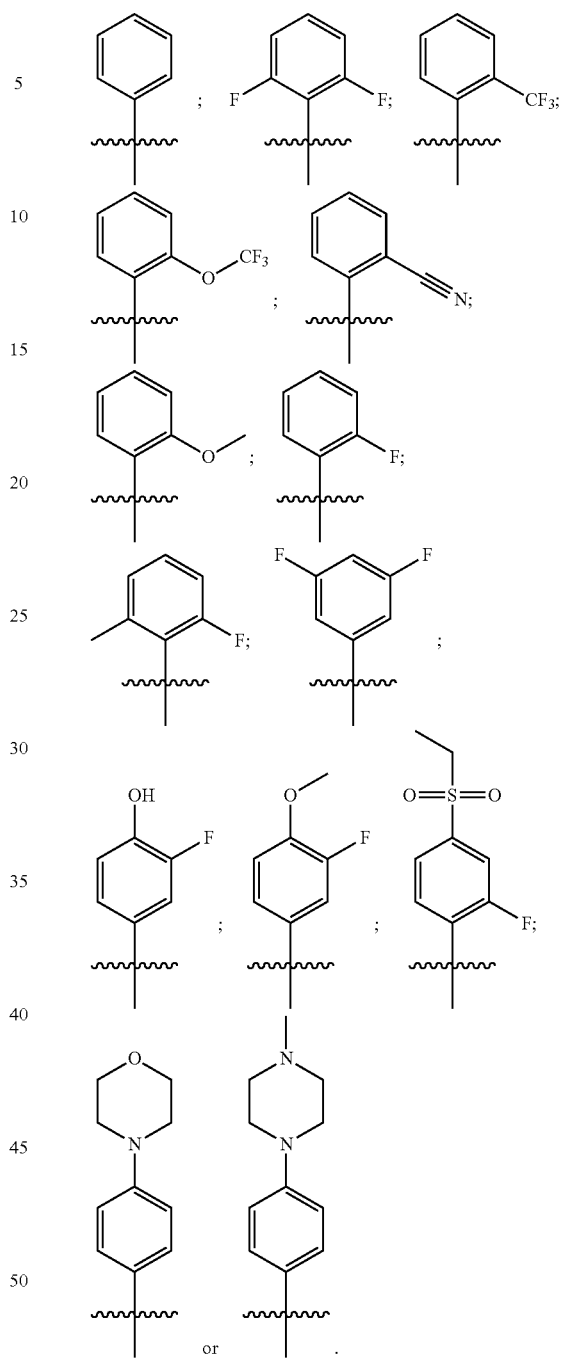

In some embodiments, the compound of structure (I) is a pharmaceutically acceptable salt (e.g., a base addition salt or an acid addition salt) or may exist as a substantially purified enantiomer or diastereomer. Accordingly, some embodiments provide a pharmaceutically acceptable salt of the compound according to any one of the foregoing embodiments. Another embodiment provides a substantially purified enantiomer or diastereomer according to any one of the foregoing embodiments.

In various different embodiments, the compound has one of the structures set forth in Table 1 below. Exemplary compounds in Table 1 were prepared by the methods set forth in the examples or known in the art and analyzed by mass spectrometry and/or $^1$H NMR.

TABLE 1

| | Representative compounds of structure (I) | | |
|---|---|---|---|
| No. | Structure | Name | Salt |
| I-1 | | (1s,4s)-4-(((4-(1-(2,6-difluorophenyl)-1H-pyrazol-4-yl)pyrimidin-5-yl)oxy)methyl)cyclohexan-1-amine | HCl |
| I-2 | | (1s,4s)-4-(((4-(1-(2-(trifluoromethyl)phenyl)-1H-pyrazol-4-yl)pyrimidin-5-yl)oxy)methyl)cyclohexan-1-amine | HCl |
| I-3 | | (1s,4s)-4-(((4-(1-(2-(trifluoromethoxy)phenyl)-1H-pyrazol-4-yl)pyrimidin-5-yl)oxy)methyl)cyclohexan-1-amine | HCl |
| I-4 | | 2-(4-(5-(((1s,4s)-4-aminocyclohexyl)methoxy)pyrimidin-4-yl)-1H-pyrazol-1-yl)benzonitrile | HCl |

TABLE 1-continued

Representative compounds of structure (I)

| No. | Structure | Name | Salt |
|---|---|---|---|
| I-5 | 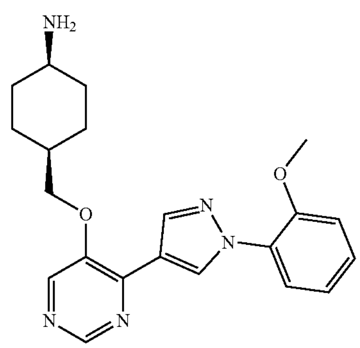 [SMILES: COc1ccccc1-n1cc(-c2ncncc2OC[C@H]2CC[C@@H](N)CC2)cn1] | (1s,4s)-4-(((4-(1-(2-methoxyphenyl)-1H-pyrazol-4-yl)pyrimidin-5-yl)oxy)methyl)cyclohexan-1-amine | HCl |
| I-6 | 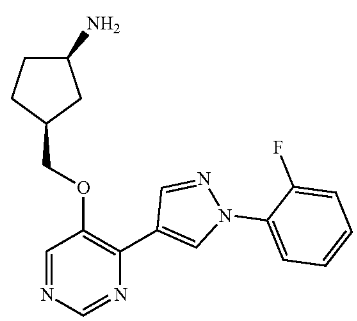 [SMILES: N[C@@H]1CC[C@H](COc2cncnc2-c2cnn(-c3ccccc3F)c2)C1] | (1R,3S)-3-(((4-(1-(2-fluorophenyl)-1H-pyrazol-4-yl)pyrimidin-5-yl)oxy)methyl)cyclopentan-1-amine | HCl |
| I-7 | 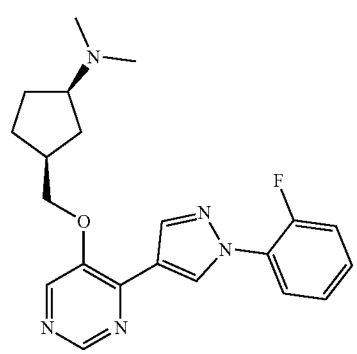 [SMILES: CN(C)[C@@H]1CC[C@H](COc2cncnc2-c2cnn(-c3ccccc3F)c2)C1] | (1R,3S)-3-(((4-(1-(2-fluorophenyl)-1H-pyrazol-4-yl)pyrimidin-5-yl)oxy)methyl)-N,N-dimethylcyclopentan-1-amine | — |
| I-8 | 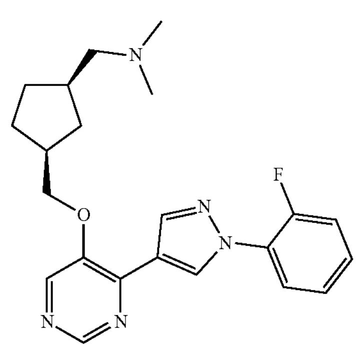 [SMILES: CN(C)C[C@@H]1CC[C@H](COc2cncnc2-c2cnn(-c3ccccc3F)c2)C1] | 1-((1R,3S)-3-(((4-(1-(2-fluorophenyl)-1H-pyrazol-4-yl)pyrimidin-5-yl)oxy)methyl)cyclopentyl)-N,N-dimethylmethanamine | — |

TABLE 1-continued

Representative compounds of structure (I)

| No. | Structure | Name | Salt |
|---|---|---|---|
| I-9 | 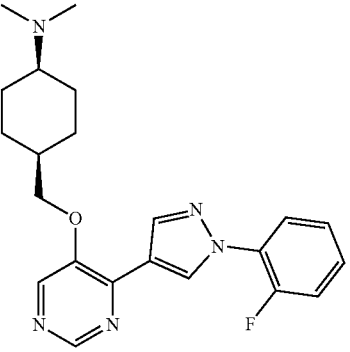 [SMILES: CN(C)[C@H]1CC[C@@H](COc2cncnc2-c2cnn(-c3ccccc3F)c2)CC1] | (1s,4s)-4-(((4-(1-(2-fluorophenyl)-1H-pyrazol-4-yl)pyrimidin-5-yl)oxy)methyl)-N,N-dimethylcyclohexan-1-amine | — |
| I-10 | 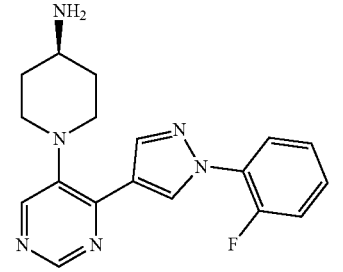 | 1-(4-(1-(2-fluorophenyl)-1H-pyrazol-4-yl)pyrimidin-5-yl)piperidin-4-amine | HCl |
| I-11 | 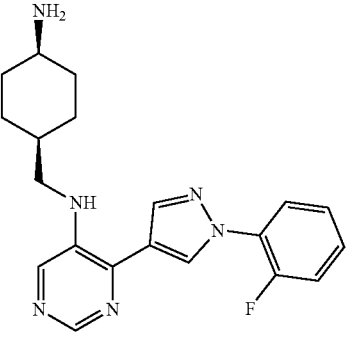 [SMILES: N[C@H]1CC[C@@H](CNc2cncnc2-c2cnn(-c3ccccc3F)c2)CC1] | N-(((1s,4s)-4-aminocyclohexyl)methyl)-4-(1-(2-fluorophenyl)-1H-pyrazol-4-yl)pyrimidin-5-amine | TFA |
| I-12 | 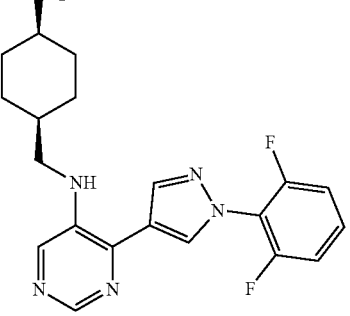 | (1s,4s)-4-(((4-(1-(2,6-difluorophenyl)-1H-pyrazol-4-yl)pyrimidin-5-yl)oxy)methyl)cyclohexan-1-amine | TFA |

TABLE 1-continued

Representative compounds of structure (I)

| No. | Structure | Name | Salt |
|---|---|---|---|
| I-13 | 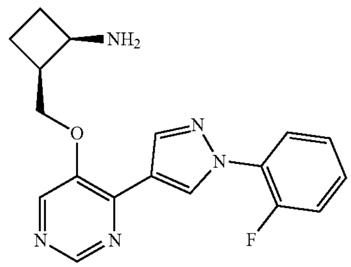 [SMILES: N[C@@H]1CC[C@@H]1COc1cncnc1-c1cnn(-c2ccccc2F)c1] | (1R,2S)-2-(((4-(1-(2-fluorophenyl)-1H-pyrazol-4-yl)pyrimidin-5-yl)oxy)methyl)cyclobutan-1-amine | HCl |
| I-14 | 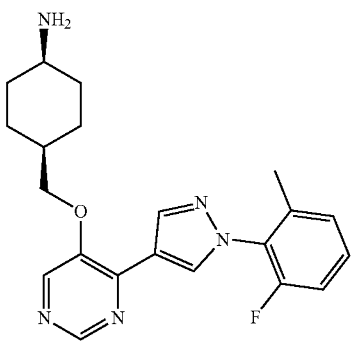 [SMILES: Cc1cccc(F)c1-n1cc(-c2ncncc2OC[C@H]2CC[C@@H](N)CC2)cn1] | (1s,4s)-4-(((4-(1-(2-fluoro-6-methylphenyl)-1H-pyrazol-4-yl)pyrimidin-5-yl)oxy)methyl)cyclohexan-1-amine | HCl |
| I-15 | 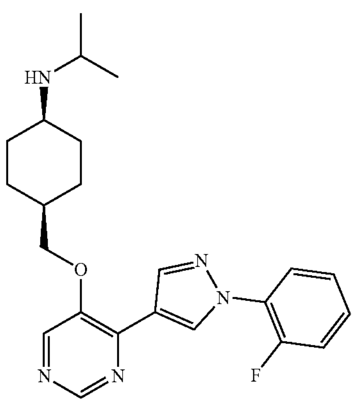 [SMILES: CC(C)N[C@H]1CC[C@@H](COc2cncnc2-c2cnn(-c3ccccc3F)c2)CC1] | (1s,4s)-4-(((4-(1-(2-fluorophenyl)-1H-pyrazol-4-yl)pyrimidin-5-yl)oxy)methyl)-N-isopropylcyclohexan-1-amine | TFA |
| I-16 | 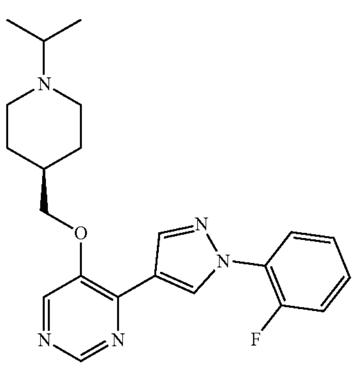 | 4-(1-(2-fluorophenyl)-1H-pyrazol-4-yl)-5-((1-isopropylpiperidin-4-yl)methoxy)pyrimidine | HCl |

TABLE 1-continued

Representative compounds of structure (I)

| No. | Structure | Name | Salt |
|---|---|---|---|
| I-17 | 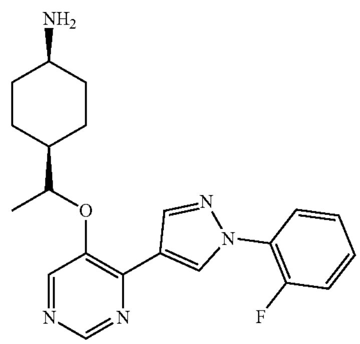 [SMILES: CC(Oc1cncnc1-c1cnn(-c2ccccc2F)c1)[C@H]1CC[C@@H](N)CC1] | (1S,4s)-4-((R)-1-((4-(1-(2-fluorophenyl)-1H-pyrazol-4-yl)pyrimidin-5-yl)oxy)ethyl)cyclohexan-1-amine | — |
| I-18 | 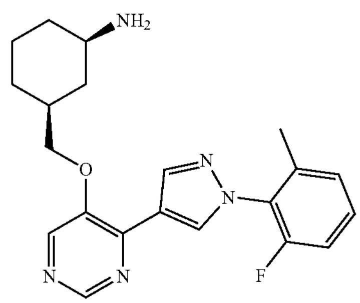 [SMILES: Cc1cccc(F)c1-n1cc(-c2ncncc2OC[C@H]2CCC[C@@H](N)C2)cn1] | (1R,3S)-3-(((4-(1-(2-fluoro-6-methylphenyl)-1H-pyrazol-4-yl)pyrimidin-5-yl)oxy)methyl)cyclohexan-1-amine | HCl |
| I-19 | 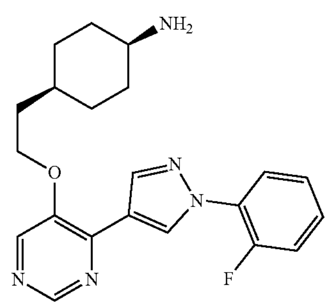 [SMILES: N[C@H]1CC[C@@H](CCOc2cncnc2-c2cnn(-c3ccccc3F)c2)CC1] | (1s,4s)-4-(2-((4-(1-(2-fluorophenyl)-1H-pyrazol-4-yl)pyrimidin-5-yl)oxy)ethyl)cyclohexan-1-amine | — |
| I-20 | 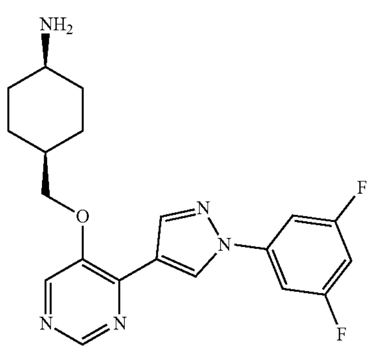 [SMILES: N[C@H]1CC[C@@H](COc2cncnc2-c2cnn(-c3cc(F)cc(F)c3)c2)CC1] | (1s,4s)-4-(((4-(1-(3,5-difluorophenyl)-1H-pyrazol-4-yl)pyrimidin-5-yl)oxy)methyl)cyclohexan-1-amine | HCl |

TABLE 1-continued

Representative compounds of structure (I)

| No. | Structure | Name | Salt |
|---|---|---|---|
| I-21 | 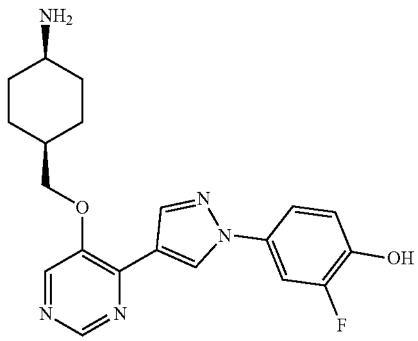 [SMILES: N[C@H]1CC[C@@H](COc2cncnc2-c2cnn(-c3ccc(O)c(F)c3)c2)CC1] | 4-(4-(5-(((1s,4s)-4-aminocyclohexyl)methoxy)pyrimidin-4-yl)-1H-pyrazol-1-yl)-2-fluorophenol | TFA |
| I-22 | 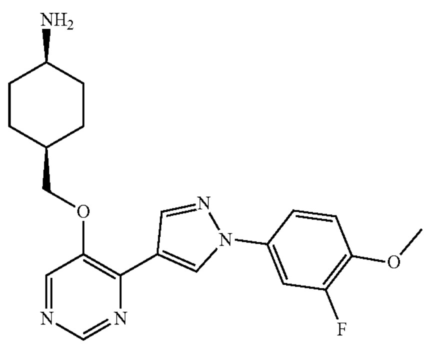 [SMILES: COc1ccc(-n2cc(-c3ncncc3OC[C@H]3CC[C@@H](N)CC3)cn2)cc1F] | (1s,4s)-4-(((4-(1-(3-fluoro-4-methoxyphenyl)-1H-pyrazol-4-yl)pyrimidin-5-yl)oxy)methyl)cyclohexan-1-amine | HCl |
| I-23 | 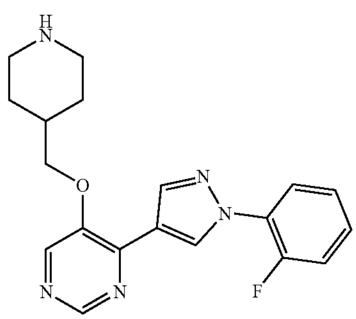 [SMILES: Fc1ccccc1-n1cc(-c2ncncc2OCC2CCNCC2)cn1] | 4-(1-(2-fluorophenyl)-1H-pyrazol-4-yl)-5-(piperidin-4-ylmethoxy)pyrimidine | — |
| I-24 | 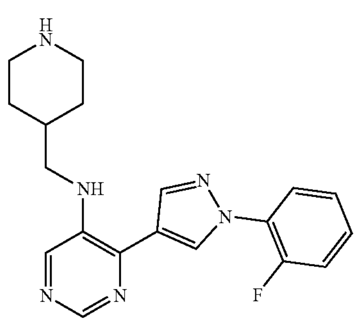 [SMILES: Fc1ccccc1-n1cc(-c2ncncc2NCC2CCNCC2)cn1] | 4-(1-(2-fluorophenyl)-1H-pyrazol-4-yl)-N-(piperidin-4-ylmethyl)pyrimidin-5-amine | — |

TABLE 1-continued

Representative compounds of structure (I)

| No. | Structure | Name | Salt |
|---|---|---|---|
| I-25 | 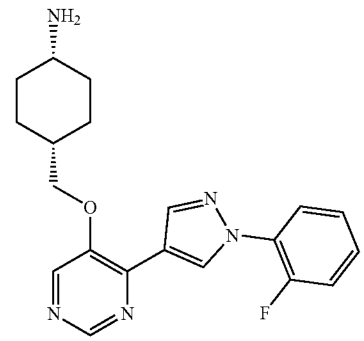 [SMILES: N[C@H]1CC[C@@H](COc2cncnc2-c2cnn(-c3ccccc3F)c2)CC1] | (1s,4s)-4-(((4-(1-(2-fluorophenyl)-1H-pyrazol-4-yl)pyrimidin-5-yl)oxy)methyl)cyclohexan-1-amine | — |
| I-26 | 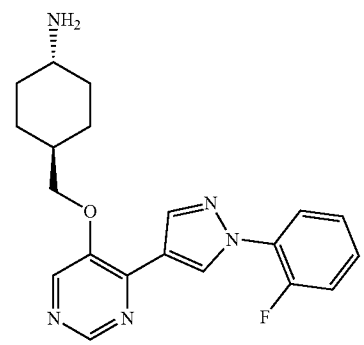 [SMILES: N[C@H]1CC[C@H](COc2cncnc2-c2cnn(-c3ccccc3F)c2)CC1] | (1r,4r)-4-(((4-(1-(2-fluorophenyl)-1H-pyrazol-4-yl)pyrimidin-5-yl)oxy)methyl)cyclohexan-1-amine | — |
| I-27 | 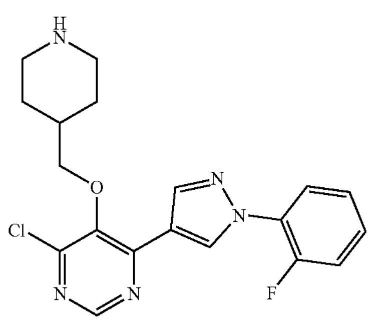 [SMILES: Fc1ccccc1-n1cc(-c2ncnc(Cl)c2OCC2CCNCC2)cn1] | 4-chloro-6-(1-(2-fluorophenyl)-1H-pyrazol-4-yl)-5-(piperidin-4-ylmethoxy)pyrimidine | — |
| I-28 | 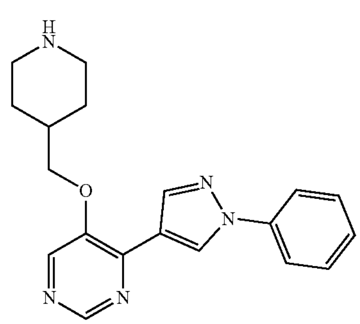 [SMILES: c1ccc(-n2cc(-c3ncncc3OCC3CCNCC3)cn2)cc1] | 4-(1-phenyl-1H-pyrazol-4-yl)-5-(piperidin-4-ylmethoxy)pyrimidine | — |

TABLE 1-continued

Representative compounds of structure (I)

| No. | Structure | Name | Salt |
|---|---|---|---|
| I-29 | 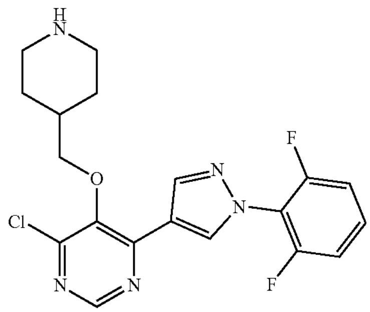 [SMILES: Fc1cccc(F)c1-n1cc(-c2ncnc(Cl)c2OCC2CCNCC2)cn1] | 4-chloro-6-(1-(2,6-difluorophenyl)-1H-pyrazol-4-yl)-5-(piperidin-4-ylmethoxy)pyrimidine | — |
| I-30 | 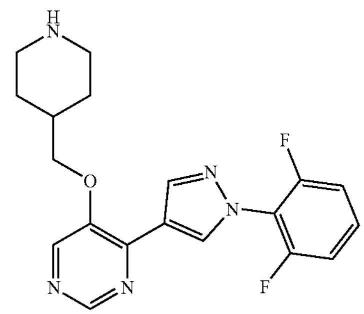 [SMILES: Fc1cccc(F)c1-n1cc(-c2ncncc2OCC2CCNCC2)cn1] | 4-(1-(2,6-difluorophenyl)-1H-pyrazol-4-yl)-5-(piperidin-4-ylmethoxy)pyrimidine | — |
| I-31 | 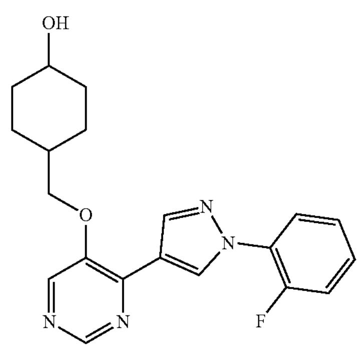 [SMILES: OC1CCC(COc2cncnc2-c2cnn(-c3ccccc3F)c2)CC1] | 4-(((4-(1-(2-fluorophenyl)-1H-pyrazol-4-yl)pyrimidin-5-yl)oxy)methyl)cyclohexan-1-ol | — |
| I-32 | 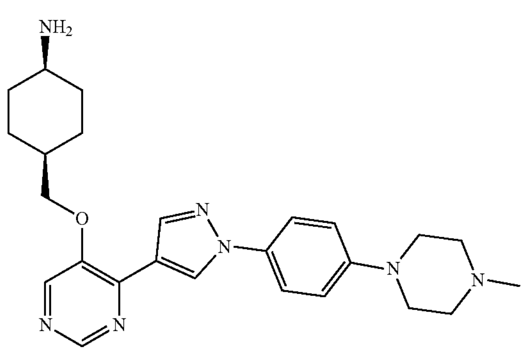 [SMILES: CN1CCN(c2ccc(-n3cc(-c4ncncc4OC[C@H]4CC[C@@H](N)CC4)cn3)cc2)CC1] | (1s,4s)-4-(((4-(1-(4-(4-methylpiperazin-1-yl)phenyl)-1H-pyrazol-4-yl)pyrimidin-5-yl)oxy)methyl)cyclohexan-1-amine | — |

TABLE 1-continued

Representative compounds of structure (I)

| No. | Structure | Name | Salt |
|---|---|---|---|
| I-33 | 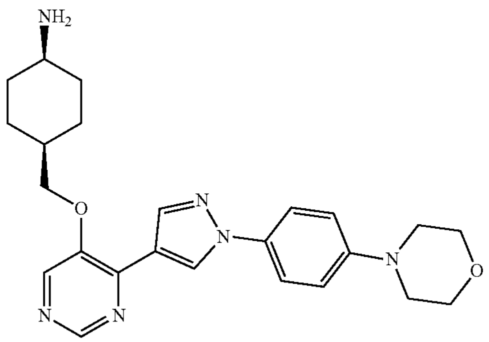 [SMILES: N[C@H]1CC[C@@H](COc2cncnc2-c2cnn(-c3ccc(N4CCOCC4)cc3)c2)CC1] | (1s,4s)-4-(((4-(1-(4-morpholinophenyl)-1H-pyrazol-4-yl)pyrimidin-5-yl)oxy)methyl)cyclohexan-1-amine | — |
| I-34 | 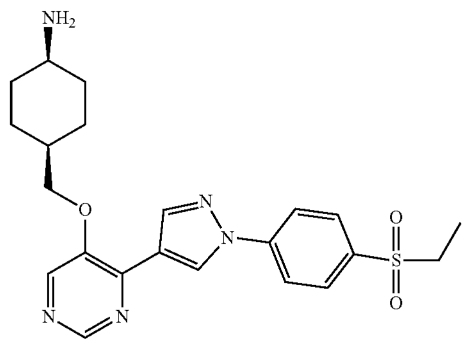 [SMILES: CCS(=O)(=O)c1ccc(-n2cc(-c3ncncc3OC[C@H]3CC[C@@H](N)CC3)cn2)cc1] | (1s,4s)-4-(((4-(1-(4-(ethylsulfonyl)phenyl)-1H-pyrazol-4-yl)pyrimidin-5-yl)oxy)methyl)cyclohexan-1-amine | — |
| I-35 | 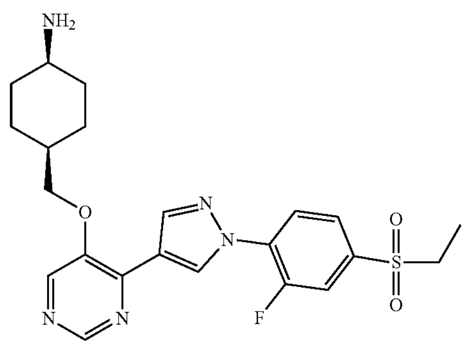 [SMILES: CCS(=O)(=O)c1ccc(-n2cc(-c3ncncc3OC[C@H]3CC[C@@H](N)CC3)cn2)c(F)c1] | (1s,4s)-4-(((4-(1-(4-(ethylsulfonyl)-2-fluorophenyl)-1H-pyrazol-4-yl)pyrimidin-5-yl)oxy)methyl)cyclohexan-1-amine | — |

It is understood that in the present description, combinations of substituents and/or variables of the depicted formulae are permissible only if such contributions result in stable compounds.

Furthermore, all compounds of the disclosure which exist in free base or acid form can be converted to their pharmaceutically acceptable salts by treatment with the appropriate inorganic or organic base or acid by methods known to one skilled in the art. Salts of the compounds of the disclosure can be converted to their free base or acid form by standard techniques.

Pharmaceutical Compositions

Other embodiments are directed to pharmaceutical compositions. The pharmaceutical composition comprises any one (or more) of the foregoing compounds and a pharmaceutically acceptable carrier. In some embodiments, the pharmaceutical composition is formulated for oral administration. In other embodiments, the pharmaceutical composition is formulated for injection. In still more embodiments, the pharmaceutical compositions comprise a compound as disclosed herein and an additional therapeutic agent. Non-limiting examples of such therapeutic agents are described herein below.

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In certain embodiments, a compound as described herein is administered in a local rather than systemic manner, for example, via injection of the compound directly into an organ, often in a depot preparation or sustained release formulation. In specific embodiments, long acting formulations are administered by implantation (for example subcutaneously or intramuscularly) or by intramuscular injection. Furthermore, in other embodiments, the drug is delivered in a targeted drug delivery system, for example, in a liposome coated with organ-specific antibody. In such embodiments, the liposomes are targeted to and taken up selectively by the organ. In yet other embodiments, the compound as described herein is provided in the form of a rapid release formulation, in the form of an extended release formulation, or in the form of an intermediate release formulation. In yet other embodiments, the compound described herein is administered topically.

The compounds according to the disclosure are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that are used in some embodiments. An exemplary dosage is 10 to 30 mg per day. The exact dosage will depend upon the route of administration, the form in which the compound is administered, the subject to be treated, the body weight of the subject to be treated, and the preference and experience of the attending physician.

In some embodiments, a compound of the disclosure is administered in a single dose. Typically, such administration will be by injection, e.g., intravenous injection, in order to introduce the agent quickly. However, other routes are used as appropriate. A single dose of a compound of the disclosure may also be used for treatment of an acute condition.

In some embodiments, a compound of the disclosure is administered in multiple doses. In some embodiments, dosing is about once, twice, three times, four times, five times, six times, or more than six times per day. In other embodiments, dosing is about once a month, once every two weeks, once a week, or once every other day. In another embodiment a compound of the disclosure and another agent are administered together about once per day to about 6 times per day. In another embodiment the administration of a compound of the disclosure and an agent continues for less than about 7 days. In yet another embodiment the administration continues for more than about 6, 10, 14, 28 days, two months, six months, or one year. In some cases, continuous dosing is achieved and maintained as long as necessary.

Administration of the compounds of the disclosure may continue as long as necessary. In some embodiments, a compound of the disclosure is administered for more than 1, 2, 3, 4, 5, 6, 7, 14, or 28 days. In some embodiments, a compound of the disclosure is administered for less than 28, 14, 7, 6, 5, 4, 3, 2, or 1 day. In some embodiments, a compound of the disclosure is administered chronically on an ongoing basis, e.g., for the treatment of chronic effects.

In some embodiments, the compounds of the disclosure are administered in dosages. It is known in the art that due to intersubject variability in compound pharmacokinetics, individualization of dosing regimen is necessary for optimal therapy. Dosing for a compound of the disclosure may be found by routine experimentation in light of the instant disclosure.

In some embodiments, the compounds described herein are formulated into pharmaceutical compositions. In specific embodiments, pharmaceutical compositions are formulated in a conventional manner using one or more physiologically acceptable carriers comprising excipients and auxiliaries which facilitate processing of the active compounds into preparations which can be used pharmaceutically. Proper formulation is dependent upon the route of administration chosen. Any pharmaceutically acceptable techniques, carriers, and excipients are used as suitable to formulate the pharmaceutical compositions described herein: Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999).

Provided herein are pharmaceutical compositions comprising a compound of structure (I) and a pharmaceutically acceptable diluent(s), excipient(s), or carrier(s). In certain embodiments, the compounds described are administered as pharmaceutical compositions in which compounds of structure (I) are mixed with other active ingredients, as in combination therapy. Encompassed herein are all combinations of actives set forth in the combination therapies section below and throughout this disclosure. In specific embodiments, the pharmaceutical compositions include one or more compounds of structure (I).

A pharmaceutical composition, as used herein, refers to a mixture of a compound of structure (I) with other chemical components, such as carriers, stabilizers, diluents, dispersing agents, suspending agents, thickening agents, and/or excipients. In certain embodiments, the pharmaceutical composition facilitates administration of the compound to an organism. In some embodiments, practicing the methods of treatment or use provided herein, therapeutically effective amounts of compounds of structure (I) provided herein are administered in a pharmaceutical composition to a mammal having a disease, disorder or medical condition to be treated. In specific embodiments, the mammal is a human. In certain embodiments, therapeutically effective amounts vary depending on the severity of the disease, the age and relative health of the subject, the potency of the compound used and other factors. The compounds described herein are used singly or in combination with one or more therapeutic agents as components of mixtures.

In one embodiment, one or more compounds of structure (I) is formulated in an aqueous solutions. In specific embodiments, the aqueous solution is selected from, by way of example only, a physiologically compatible buffer, such as Hank's solution, Ringer's solution, or physiological saline buffer. In other embodiments, one or more compound of structure (I) is/are formulated for transmucosal administration. In specific embodiments, transmucosal formulations include penetrants that are appropriate to the barrier to be permeated. In still other embodiments wherein the compounds described herein are formulated for other parenteral injections, appropriate formulations include aqueous or non-aqueous solutions. In specific embodiments, such solutions include physiologically compatible buffers and/or excipients.

In another embodiment, compounds described herein are formulated for oral administration. Compounds described herein are formulated by combining the active compounds with, e.g., pharmaceutically acceptable carriers or excipients. In various embodiments, the compounds described herein are formulated in oral dosage forms that include, by way of example only, tablets, powders, pills, dragees, capsules, liquids, gels, syrups, elixirs, slurries, suspensions and the like.

In certain embodiments, pharmaceutical preparations for oral use are obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as: for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. In specific embodiments, disintegrating agents are optionally added. Disintegrating agents include, by way of example only, cross-linked croscarmellose sodium, polyvinylpyrrolidone, agar, or alginic acid or a salt thereof such as sodium alginate.

In one embodiment, dosage forms, such as dragee cores and tablets, are provided with one or more suitable coating. In specific embodiments, concentrated sugar solutions are used for coating the dosage form. The sugar solutions, optionally contain additional components, such as by way of example only, gum arabic, talc, polyvinylpyrrolidone, carbopol gel, polyethylene glycol, and/or titanium dioxide, lacquer solutions, and suitable organic solvents or solvent mixtures. Dyestuffs and/or pigments are also optionally added to the coatings for identification purposes. Additionally, the dyestuffs and/or pigments are optionally utilized to characterize different combinations of active compound doses.

In certain embodiments, therapeutically effective amounts of at least one of the compounds described herein are formulated into other oral dosage forms. Oral dosage forms include push-fit capsules made of gelatin, as well as soft, sealed capsules made of gelatin and a plasticizer, such as glycerol or sorbitol. In specific embodiments, push-fit capsules contain the active ingredients in admixture with one or more filler. Fillers include, by way of example only, lactose, binders such as starches, and/or lubricants such as talc or magnesium stearate and, optionally, stabilizers. In other embodiments, soft capsules, contain one or more active compound that is dissolved or suspended in a suitable liquid. Suitable liquids include, by way of example only, one or more fatty oil, liquid paraffin, or liquid polyethylene glycol. In addition, stabilizers are optionally added.

In other embodiments, therapeutically effective amounts of at least one of the compounds described herein are formulated for buccal or sublingual administration. Formulations suitable for buccal or sublingual administration include, by way of example only, tablets, lozenges, or gels. In still other embodiments, the compounds described herein are formulated for parental injection, including formulations suitable for bolus injection or continuous infusion. In specific embodiments, formulations for injection are presented in unit dosage form (e.g., in ampoules) or in multi-dose containers. Preservatives are, optionally, added to the injection formulations. In still other embodiments, the pharmaceutical compositions are formulated in a form suitable for parenteral injection as sterile suspensions, solutions or emulsions in oily or aqueous vehicles. Parenteral injection formulations optionally contain formulatory agents such as suspending, stabilizing and/or dispersing agents. In specific embodiments, pharmaceutical formulations for parenteral administration include aqueous solutions of the active compounds in water-soluble form. In additional embodiments, suspensions of the active compounds (e.g., compounds of structure (I)) are prepared as appropriate oily injection suspensions. Suitable lipophilic solvents or vehicles for use in the pharmaceutical compositions described herein include, by way of example only, fatty oils such as sesame oil, or synthetic fatty acid esters, such as ethyl oleate or triglycerides, or liposomes. In certain specific embodiments, aqueous injection suspensions contain substances which increase the viscosity of the suspension, such as sodium carboxymethyl cellulose, sorbitol, or dextran. Optionally, the suspension contains suitable stabilizers or agents which increase the solubility of the compounds to allow for the preparation of highly concentrated solutions. Alternatively, in other embodiments, the active ingredient is in powder form for constitution with a suitable vehicle, e.g., sterile pyrogen-free water, before use.

In still other embodiments, the compounds of structure (I) are administered topically. The compounds described herein are formulated into a variety of topically administrable compositions, such as solutions, suspensions, lotions, gels, pastes, medicated sticks, balms, creams or ointments. Such pharmaceutical compositions optionally contain solubilizers, stabilizers, tonicity enhancing agents, buffers and preservatives.

In yet other embodiments, the compounds of structure (I) are formulated for transdermal administration. In specific embodiments, transdermal formulations employ transdermal delivery devices and transdermal delivery patches and can be lipophilic emulsions or buffered, aqueous solutions, dissolved and/or dispersed in a polymer or an adhesive. In various embodiments, such patches are constructed for continuous, pulsatile, or on demand delivery of pharmaceutical agents. In additional embodiments, the transdermal delivery of the compounds of structure (I) is accomplished by means of iontophoretic patches and the like. In certain embodiments, transdermal patches provide controlled delivery of the compounds of structure (I). In specific embodiments, the rate of absorption is slowed by using rate-controlling membranes or by trapping the compound within a polymer matrix or gel. In alternative embodiments, absorption enhancers are used to increase absorption. Absorption enhancers or carriers include absorbable pharmaceutically acceptable solvents that assist passage through the skin. For example, in one embodiment, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

In other embodiments, the compounds of structure (I) are formulated for administration by inhalation. Various forms suitable for administration by inhalation include, but are not limited to, aerosols, mists or powders. Pharmaceutical compositions of any of compound of structure (I) are conveniently delivered in the form of an aerosol spray presentation from pressurized packs or a nebulizer, with the use of a suitable propellant (e.g., dichlorodifluoromethane, trichlorofluoromethane, dichlorotetrafluoroethane, carbon dioxide or other suitable gas). In specific embodiments, the dosage unit of a pressurized aerosol is determined by providing a valve to deliver a metered amount. In certain embodiments, capsules and cartridges of, such as, by way of example only, gelatin for use in an inhaler or insufflator is formulated containing a powder mix of the compound and a suitable powder base such as lactose or starch.

In still other embodiments, the compounds of structure (I) are formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG, and the like. In suppository forms of the compositions, a low-melting wax such as, but not limited to, a mixture of fatty acid glycerides, optionally in combination with cocoa butter is first melted.

In certain embodiments, pharmaceutical compositions are formulated in any conventional manner using one or more physiologically acceptable carriers comprising excipients and auxiliaries which facilitate processing of the active compounds into preparations which can be used pharmaceutically. Proper formulation is dependent upon the route of administration chosen. Any pharmaceutically acceptable techniques, carriers, and excipients are optionally used as suitable. Pharmaceutical compositions comprising a compound of structure (I) are manufactured in a conventional manner, such as, by way of example only, by means of conventional mixing, dissolving, granulating, dragee-making, levigating, emulsifying, encapsulating, entrapping or compression processes.

Pharmaceutical compositions include at least one pharmaceutically acceptable carrier, diluent or excipient and at least one compound of structure (I), described herein as an active ingredient. The active ingredient is in free-acid or free-base form, or in a pharmaceutically acceptable salt form. In addition, the methods and pharmaceutical compositions described herein include the use of N-oxides, crystalline forms (also known as polymorphs), as well as active metabolites of these compounds having the same type of activity. All tautomers of the compounds described herein are included within the scope of the compounds presented herein. Additionally, the compounds described herein encompass unsolvated as well as solvated forms with pharmaceutically acceptable solvents such as water, ethanol, and the like. The solvated forms of the compounds presented herein are also considered to be disclosed herein. In addition, the pharmaceutical compositions optionally include other medicinal or pharmaceutical agents, carriers, adjuvants, such as preserving, stabilizing, wetting or emulsifying agents, solution promoters, salts for regulating the osmotic pressure, buffers, and/or other therapeutically valuable substances.

Methods for the preparation of compositions comprising the compounds described herein include formulating the compounds with one or more inert, pharmaceutically acceptable excipients or carriers to form a solid, semi-solid or liquid. Solid compositions include, but are not limited to, powders, tablets, dispersible granules, capsules, cachets, and suppositories. Liquid compositions include solutions in which a compound is dissolved, emulsions comprising a compound, or a solution containing liposomes, micelles, or nanoparticles comprising a compound as disclosed herein. Semi-solid compositions include, but are not limited to, gels, suspensions and creams. The form of the pharmaceutical compositions described herein include liquid solutions or suspensions, solid forms suitable for solution or suspension in a liquid prior to use, or as emulsions. These compositions also optionally contain minor amounts of nontoxic, auxiliary substances, such as wetting or emulsifying agents, pH buffering agents, and so forth.

In some embodiments, pharmaceutical composition comprising at least one compound of structure (I) illustratively takes the form of a liquid where the agents are present in solution, in suspension or both. Typically when the composition is administered as a solution or suspension a first portion of the agent is present in solution and a second portion of the agent is present in particulate form, in suspension in a liquid matrix. In some embodiments, a liquid composition includes a gel formulation. In other embodiments, the liquid composition is aqueous.

In certain embodiments, useful aqueous suspensions contain one or more polymers as suspending agents. Useful polymers include water-soluble polymers such as cellulosic polymers, e.g., hydroxypropyl methylcellulose, and water-insoluble polymers such as cross-linked carboxyl-containing polymers. Certain pharmaceutical compositions described herein comprise a mucoadhesive polymer, selected for example from carboxymethylcellulose, carbomer (acrylic acid polymer), poly(methylmethacrylate), polyacrylamide, polycarbophil, acrylic acid/butyl acrylate copolymer, sodium alginate and dextran.

Useful pharmaceutical compositions also, optionally, include solubilizing agents to aid in the solubility of a compound of structure (I). The term "solubilizing agent" generally includes agents that result in formation of a micellar solution or a true solution of the agent. Certain acceptable nonionic surfactants, for example polysorbate 80, are useful as solubilizing agents, as can ophthalmically acceptable glycols, polyglycols, e.g., polyethylene glycol 400, and glycol ethers.

Furthermore, useful pharmaceutical compositions optionally include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

Additionally, useful compositions also, optionally, include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

Other useful pharmaceutical compositions optionally include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

Still other useful compositions include one or more surfactants to enhance physical stability or for other purposes. Suitable nonionic surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40.

Still other useful compositions include one or more antioxidants to enhance chemical stability where required. Suitable antioxidants include, by way of example only, ascorbic acid and sodium metabisulfite.

In certain embodiments, aqueous suspension compositions are packaged in single-dose non-reclosable containers. Alternatively, multiple-dose reclosable containers are used, in which case it is typical to include a preservative in the composition.

In alternative embodiments, other delivery systems for hydrophobic pharmaceutical compounds are employed. Liposomes and emulsions are examples of delivery vehicles or carriers useful herein. In certain embodiments, organic solvents such as N-methylpyrrolidone are also employed. In additional embodiments, the compounds described herein are delivered using a sustained-release system, such as semipermeable matrices of solid hydrophobic polymers containing the therapeutic agent. Various sustained-release materials are useful herein. In some embodiments, sustained-release capsules release the compounds for a few weeks up to over 100 days. Depending on the chemical nature and the biological stability of the therapeutic reagent, additional strategies for protein stabilization are employed.

In certain embodiments, the formulations described herein comprise one or more antioxidants, metal chelating agents, thiol containing compounds and/or other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (1) pentosan polysulfate and other heparinoids, (m) divalent cations such as magnesium and zinc; or (n) combinations thereof.

In some embodiments, the concentration of the compound of structure (I) provided in the pharmaceutical compositions of the present disclosure is less than 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v or v/v.

In some embodiments, the concentration of the compound of structure (I) provided in the pharmaceutical compositions of the present disclosure is greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25%6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v, or v/v.

In some embodiments, the concentration of the compound of structure (I) provided in the pharmaceutical compositions of the present disclosure is in the range from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12%, approximately 1% to approximately 10% w/w, w/v or v/v.

In some embodiments, the concentration of the compound of structure (I) provided in the pharmaceutical compositions of the present disclosure is in the range from approximately 0.001% to approximately 10%, approximately 0.01% to approximately 5%, approximately 0.02% to approximately 4.5%, approximately 0.03% to approximately 4%, approximately 0.04% to approximately 3.5%, approximately 0.05% to approximately 3%, approximately 0.06% to approximately 2.5%, approximately 0.07% to approximately 2%, approximately 0.08% to approximately 1.5%, approximately 0.09% to approximately 1%, approximately 0.1% to approximately 0.9% w/w, w/v or v/v.

In some embodiments, the amount the compound of structure (I) provided in the pharmaceutical compositions of the present disclosure is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g.

In some embodiments, the amount of the compound of structure (I) provided in the pharmaceutical compositions of the present disclosure is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, 3 g, 3.5, 4 g, 4.5 g, 5 g, 5.5 g, 6 g, 6.5 g, 7 g, 7.5 g, 8 g, 8.5 g, 9 g, 9.5 g, or 10 g.

In some embodiments, the amount of the compound of structure (I) provided in the pharmaceutical compositions of the present disclosure is in the range of 0.0001-10 g, 0.0005-9 g, 0.001-8 g, 0.005-7 g, 0.01-6 g, 0.05-5 g, 0.1-4 g, 0.5-4 g, or 1-3 g.

Kits/Articles of Manufacture

For use in the therapeutic applications described herein, kits and articles of manufacture are also provided. In some embodiments, such kits comprise a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. The containers are formed from a variety of materials such as glass or plastic.

The articles of manufacture provided herein contain packaging materials. Packaging materials for use in packaging pharmaceutical products include those found in, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. For example, the container(s) includes one or more compounds described herein, optionally in a composition or in combination with another agent as disclosed herein. The container(s) optionally have a sterile access port (for example the container is an intravenous solution bag or a vial having a stopper pierceable by a hypodermic injection needle). Such kits optionally comprise a compound with an identifying description or label or instructions relating to its use in the methods described herein.

For example, a kit typically includes one or more additional containers, each with one or more of various materials (such as reagents, optionally in concentrated form, and/or devices) desirable from a commercial and user standpoint for use of a compound described herein. Non-limiting examples of such materials include, but not limited to, buffers, diluents, filters, needles, syringes; carrier, package, container, vial and/or tube labels listing contents and/or instructions for use, and package inserts with instructions for use. A set of instructions will also typically be included. A label is optionally on or associated with the container. For example, a label is on a container when letters, numbers or other characters forming the label are attached, molded or etched into the container itself, a label is associated with a container when it is present within a receptacle or carrier that also holds the container, e.g., as a package insert. In addition, a label is used to indicate that the contents are to be used for a specific therapeutic application. In addition, the label indicates directions for use of the contents, such as in the methods described herein. In certain embodiments, the pharmaceutical compositions are presented in a pack or dispenser device which contains one or more unit dosage forms containing a compound provided herein. The pack for example contains metal or plastic foil, such as a blister pack. Or, the pack or dispenser device is accompanied by instructions for administration. Or, the pack or dispenser is accompanied with a notice associated with the container in form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for prescription drugs, or the approved product insert. In some embodiments, compositions containing a compound provided herein formulated in a compatible pharmaceutical carrier are prepared, placed in an appropriate container, and labeled for treatment of an indicated condition.

Methods of Treatment and Administration

Embodiments of the present disclosure provide a method for treating cancer. One embodiment provides a method for treating cancer, the method comprising administering an effective amount of a pharmaceutical composition as disclosed in any one of the embodiments herein to a subject in need thereof.

In some embodiments, the cancer is a hematological cancer. For example, in some embodiments, the cancer is leukemia (e.g., acute myeloid leukemia). In some embodiments, the cancer is a solid tumor. In some embodiments, the cancer is breast cancer (e.g., triple negative breast cancer). In some embodiments, the cancer is lung cancer (e.g., non-small cell lung cancer). In some specific embodiments, the cancer is brain cancer (e.g., glioblastoma).

Further therapeutic agents that can be combined with a compound of the disclosure are found in Goodman and Gilman's "The Pharmacological Basis of Therapeutics" Tenth Edition edited by Hardman, Limbird and Gilman or the Physician's Desk Reference, both of which are incorporated herein by reference in their entirety.

The compounds described herein can be used in combination with the agents disclosed herein or other suitable agents, depending on the condition being treated. Hence, in some embodiments the one or more compounds of the disclosure will be co-administered with other agents as described above. When used in combination therapy, the compounds described herein are administered with the second agent simultaneously or separately. This administration in combination can include simultaneous administration of the two agents in the same dosage form, simultaneous administration in separate dosage forms, and separate administration. That is, a compound described herein and any of the agents described above can be formulated together in the same dosage form and administered simultaneously. Alternatively, a compound of the disclosure and any of the agents described above can be simultaneously administered, wherein both the agents are present in separate formulations. In another alternative, a compound of the present disclosure can be administered just followed by and any of the agents described above, or vice versa. In some embodiments of the separate administration protocol, a compound of the disclosure and any of the agents described above are administered a few minutes apart, or a few hours apart, or a few days apart.

The compounds disclosed herein include a 1H-pyrazolpyrimidine class of compounds as inhibitors of MELK (Maternal Embryonic Leucine zipper Kinase), its mutant MELK (T460M), FLT3 (FMS like Tyrosine Kinase, cluster of differentiation antigen 135 (CD135), fetal liver kinase 2 (FLK2)) and its mutant) FLT3 mutant forms; FLT3 (D835Y), FLT3 (F594R595insR), FLT3 (F594R595insREY), FLT3 (ITD), FLT3 (ITD)-NPOS, FLT3 (ITD)-W51 and FLT3 (R595_E596insEY) kinases. Pharmaceutical compositions containing compounds of structure (I) compound and methods of using the compounds or compositions to treat various types of diseases or conditions mediated by MELK, FLT3 such as for example, disease states associated with abnormal cell growth such as cancer. Additionally, these compounds are important therapeutic agents for the treatment of AML, breast, TNBC, GBM, lung, prostate cancers.

Methods of Preparation

Compounds of structure (I) can be prepared according to methods known in the art and according to methods disclosed herein. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, for example, Advanced Organic Chemistry: Reactions, Mechanisms, and Structure, 5th edition (Wiley, December 2000)) or prepared as described herein.

Geneeral Reaction Scheme 1 ("Method A")

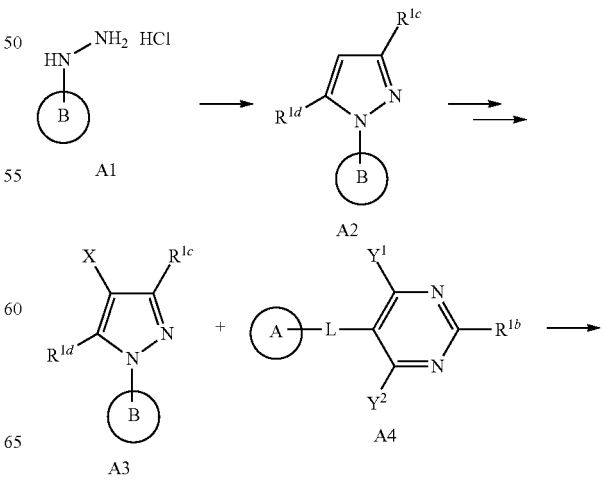

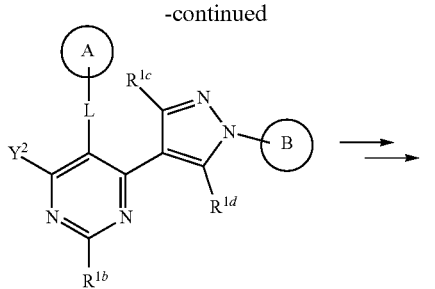

A5

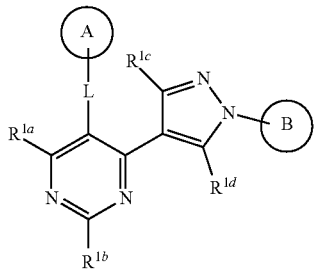

Structure (I)

Embodiments of the compound of structure (I) can be prepared according to General Reaction Scheme 1 ("Method A"), wherein $R^{1a}$, $R^{1b}$, $R^{1c}$, $R^{1d}$, L,

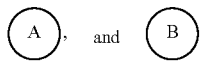

are as defined herein for structure (I). Compounds of structure A1 are purchased or prepared according to methods known in the art. Conversion of the hydrazine hydrochloride A1 to the desired product A2 can be carried out using an appropriately selected reagent and solvent (e.g., 1,1,3,3-tetramethoxypropane in ethanol) under appropriate reaction conditions (e.g., 90° C. for 16 hours). The product A2 can then be converted to add a reactive moiety X. The reactive moiety X can be selected (and, alternatively, modified if necessary) based on the compatibility with the other synthetic steps (e.g., complementary reactivity to $Y^1$ and/or $Y^2$) in view of the entire reaction scheme. X may include, but is not limited to, a halide, a pseudo-halide (e.g., triflate), a boronic acid, or a boronic ester. Reaction conditions for adding the reactive moiety X are well known in the art and can be selected based on the desired X to be added (e.g., N-iodosuccinimide in acetic acid; or pinacol borane, triethylamine, S-phos, and bis(acetonitrile)dichloropalladium(II); or bis(pinacollato)diboron, base, and [1,1'-bis(diphenylphosphino)ferrocene]-dichloropalladium(II)). Next A3 was reacted with A4, which can also be purchased or prepared according to methods known in the art, having reactive groups (e.g., a halide such as chloro) $Y^1$ and $Y^2$, to yield the desired product A5 under appropriate conditions (e.g., Suzuki coupling conditions, such as, base, and [1,1'-bis(diphenylphosphino)ferrocene]-dichloropalladium(II) in dioxane/$H_2O$ while heating). After the coupling step is complete, A5 can be optionally converted to remove $Y^2$ as necessary (e.g., using palladium on carbon, base, methanol, and $H_2$) and protecting groups can be removed as needed to yield the desired product, a compound of structure (I).

General Reaction Scheme 2 ("Method B")

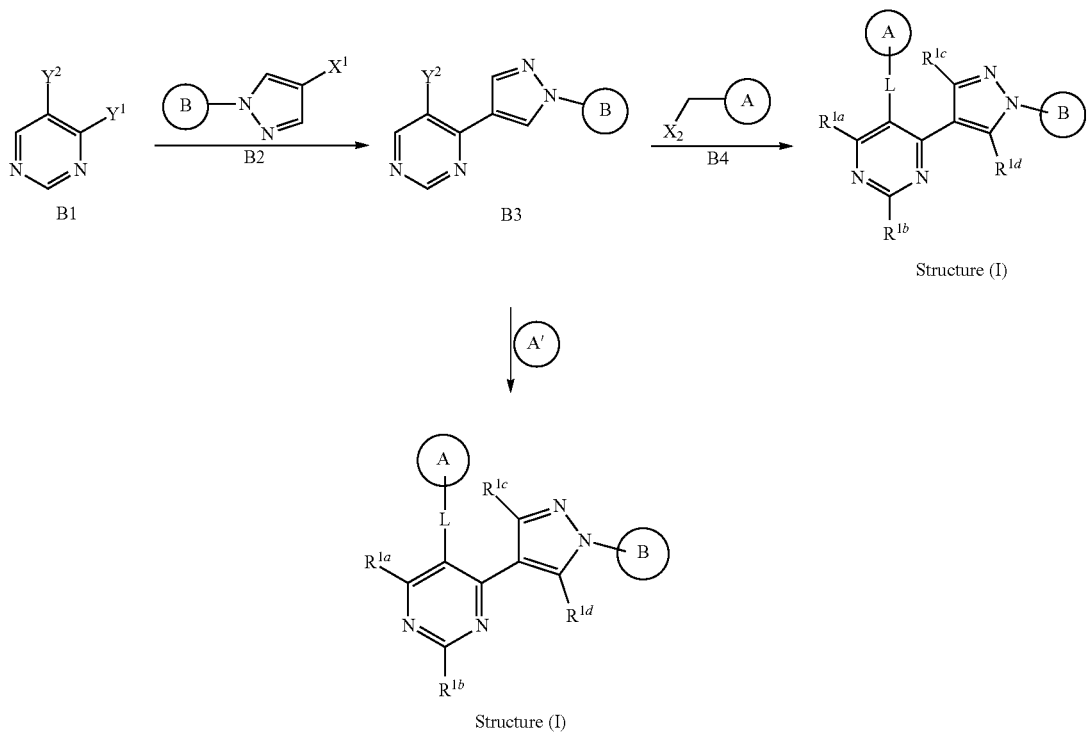

Embodiments of the compound of structure (I) can be prepared according to General Reaction Scheme 2 ("Method B"), wherein $R^{1a}$, $R^{1b}$, $R^{1c}$, $R^{1d}$, L (A), and (B)

are as defined herein for structure (I). Compounds of structures B1 and B2 are purchased or prepared according to methods known in the art. $X^1$, $X^2$, $Y^1$, and $Y^2$ are reactive groups, for example, reactive groups having complementary reactivity to form a covalent bond (e.g., forming a carbon-carbon bond with a halide and boronic ester via a Suzuki cross-coupling reaction or amine and halide to form a secondary amine). Compound B1 is reacted with compound B2 using appropriate conditions (e.g., wherein $Y^1$ is chloro and $X^1$ is a boronic ester and base with tetrakis(triphenylphosphine)palladium is used) to yield compound B3. B3 is then reacted with B4 (including protected forms thereof) under suitable conditions (e.g., wherein $X^2$ is an amine and $Y^2$ is chloro and $Cs_2CO_3$ and chloro(2-dicyclohexyl-phosphino-2',4',6'-triisopropyl-1,1'-biphenyl)[2-(2'-amino-1,1'-biphenyl)]-palladium(II) are used) to yield a compound of structure (I).

Alternatively B3 can be reacted with (A'), or a protected form thereof, which is a moiety similar to (A), but having a reactive moiety suitable for coupling to a reactive group $Y^2$ (e.g., when $Y^2$ is halo and (A')

comprises a secondary amine). The reaction of B3 with (A')

under suitable conditions (e.g., using $Cs_2CO_3$ and chloro(2-dicyclohexyl-phosphino-2',4',6'-triisopropyl-1,1'-biphenyl) [2-(2'-amino-1,1'-biphenyl)]-palladium(II)) results in a compound of structure (I) (e.g., wherein L is a direct bond).

General Reaction Scheme 3 ("Method C")

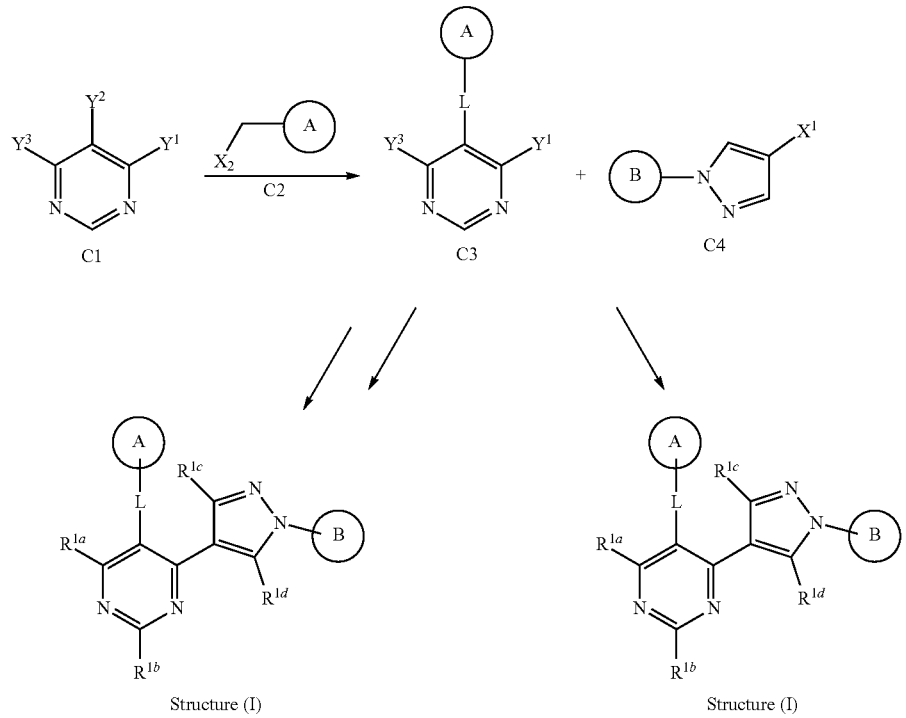

Embodiments of the compound of structure (I) can be prepared according to General Reaction Scheme 3 ("Method C"), wherein $R^{1a}$, $R^{1b}$, $R^{1c}$, $R^{1d}$, L, (A), and (B)

are as defined herein for structure (I). Compounds of structures $C_1$ and $C_2$ are purchased or prepared according to methods known in the art. $X^1$, $X^2$, $Y^1$, $Y^2$, and $Y^3$ are reactive groups, for example, reactive groups having complementary reactivity to form a covalent bond (e.g., —OH, halo/boronate ester). Compound C1 is reacted with compound C2 using appropriate conditions (e.g., DIAD, triphenylphosphine) to yield compound C3. C3 is then reacted with C4 (including protected forms thereof) under suitable conditions (e.g., wherein $X^1$ is pinacolborane and $Y^1$ is chloro and $Na_2CO_3$ and $PdCl_2(dppf)$ are used). The product of the reaction between C3 and C4 can be deprotected (e.g., using hydrochloric acid in diethyl ether) to yield a compound of structure (I). Alternatively, an additional reaction can be carried out to modify $Y^3$ (e.g., convert from a chloro to hydrogen using palladium on carbon and $H_2$ and base) before performing a deprotection step (e.g., using hydrochloric acid in diethyl ether).

compound D2 using appropriate conditions (e.g., CuI, $K_2CO_3$) to yield compound D3. D3 is then derivatized to add a reactive group (e.g., using $Br_2$ and acetic acid), which can be further modified as needed (e.g., using bis(pinacolato) diboron $PdCl_2(dppf)$ and potassium acetate). D4 is then reacted with D5 (including protected forms thereof) under suitable conditions (e.g., wherein $X^2$ is pinacolborane and $Y^1$ is chloro and $Na_2CO_3$ and $PdCl_2(dppf)$ are used). The product of the reaction between D4 and D5 can be deprotected (e.g., using hydrochloric acid in diethyl ether) to yield a compound of structure (I). Alternatively, an additional reaction can be carried out to modify $Y^2$ (e.g., convert from a chloro to hydrogen using palladium on carbon and $H_2$ and base) before performing a deprotection step (e.g., using hydrochloric acid in diethyl ether).

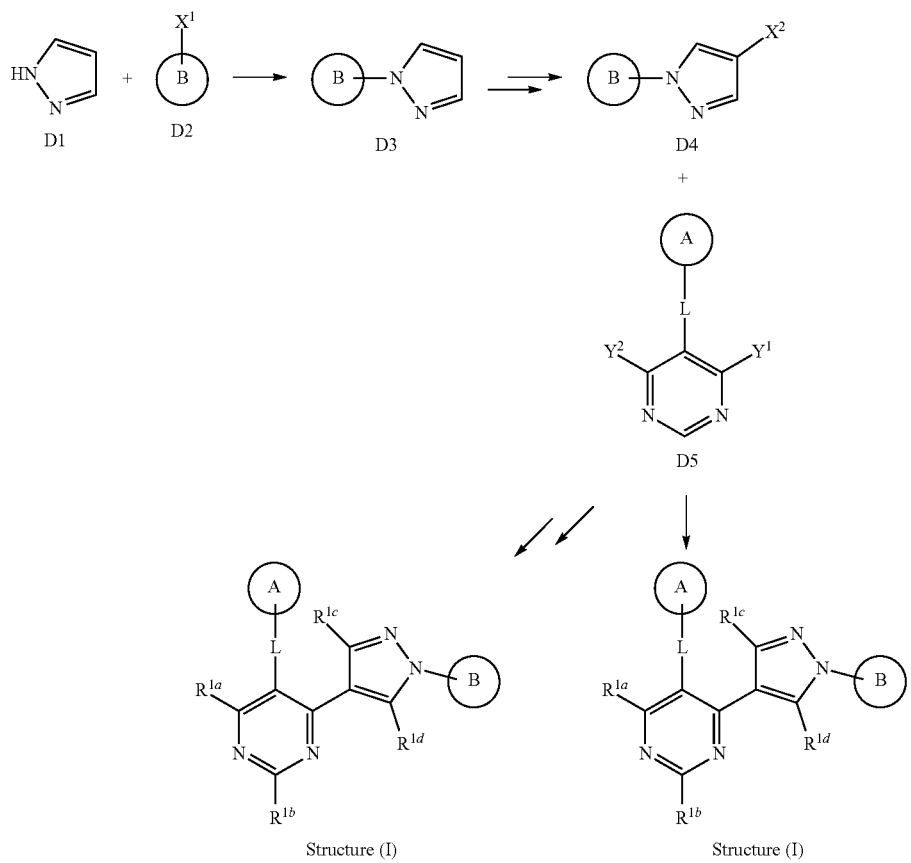

Embodiments of the compound of structure (I) can be prepared-according to General Reaction Scheme 4 ("Method D"), wherein $R^{1a}$, $R^{1b}$, $R^{1c}$, $R^{1d}$, L, (A), and (B)

are as defined herein for structure (I). Compounds of structures D1 and D2 are purchased or prepared according to methods known in the art. $X^1$, $X^2$, $Y^1$ and $Y^2$ are reactive groups, for example, reactive groups having complementary reactivity to form a covalent bond (e.g., halo to react with secondary amine of D1). Compound D1 is reacted with

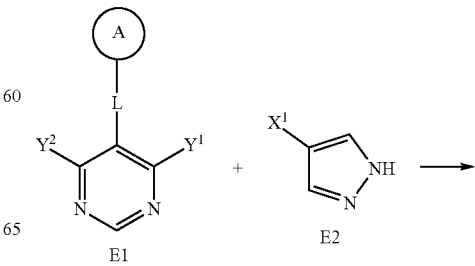

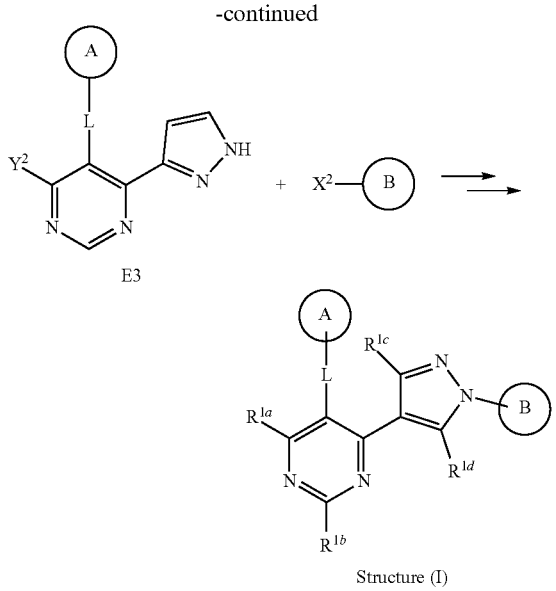

Structure (I)

Embodiments of the compound of structure (I) can be prepared according to General Reaction Scheme 5 ("Method E"), wherein $R^{1a}$, $R^{1b}$, $R^{1c}$, $R^{1d}$, L,

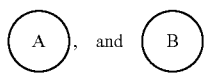

are as defined herein for structure (I). Compounds of structures E1 and E2 are purchased or prepared according to methods known in the art. $X^1$, $X^2$, $Y^1$ and $Y^2$ are reactive groups, for example, reactive groups having complementary reactivity to form a covalent bond (e.g., $X^1$ and $Y^1$ can be boronate ester and halo, respectively, and $X^2$ can be halo to react with secondary amine of E3). Compound E1 is reacted with compound E2 using appropriate conditions (e.g., bis(pinacolato)diboron PdCl$_2$(dppf) and sodium carbonate) to yield compound E3. E3 is then reacted with E4 (including protected forms thereof) under suitable conditions (e.g., wherein $X^2$ is a boronic acid and copper acetate and base are used). The product of the reaction between E3 and E4 can be deprotected (e.g., using hydrochloric acid in diethyl ether) to yield a compound of structure (I). Alternatively, an additional reaction can be carried out to modify $Y^2$ (e.g., convert from a chloro to hydrogen using palladium on carbon and H$_2$ and base) before performing a deprotection step (e.g., using hydrochloric acid in diethyl ether).

The above reaction schemes can be modified as necessary to prepare other compounds of structure (I) by adding, removing, or modifying substituents. For example, substituents or reactive moieties can be added, removed, or modified to reach a desired

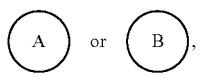

or protected form thereof. compounds of structure (I) are available to those of ordinary skill in the art. For example, other compounds of structure (I) can be prepared according to analogous methods using the appropriate starting material. It will also be appreciated by those skilled in the art that in the processes for preparing the compounds described herein the functional groups of intermediate compounds may need to be protected by suitable protecting groups. Such functional groups include, but are not limited to, hydroxy, amino, mercapto and carboxylic acid. Suitable protecting groups for hydroxy include trialkylsilyl or diarylalkylsilyl (for example, t-butyldimethylsilyl, t-butyldiphenylsilyl or trimethylsilyl), tetrahydropyranyl, benzyl, and the like. Suitable protecting groups for amino include t-butoxycarbonyl ("BOC"), benzyloxycarbonyl, and the like. Suitable protecting groups for mercapto include —C(O)—R" (where R" is alkyl, aryl or arylalkyl), p-methoxybenzyl, trityl and the like. Suitable protecting groups for carboxylic acid include alkyl, aryl or arylalkyl esters. Protecting groups are optionally added or removed in accordance with standard techniques, which are known to one skilled in the art and as described herein. The use of protecting groups is described in detail in Green, T. W. and P. G. M. Wutz, *Protective Groups in Organic Synthesis* (1999), 3rd Ed., Wiley. As one of skill in the art would appreciate, the protecting group may also be a polymer resin such as a Wang resin, Rink resin or a 2-chlorotrityl-chloride resin.

It will also be appreciated by those skilled in the art, although such protected derivatives of compounds of this disclosure may not possess pharmacological activity as such, they may be administered to a mammal and thereafter metabolized in the body to form compounds of the disclosure which are pharmacologically active. Such derivatives may therefore be described as "prodrugs". Prodrugs of compounds of this disclosure are included within the scope of embodiments of the invention.

The examples and preparations provided below further illustrate and exemplify the compounds of the present disclosure and methods of preparing such compounds. It is to be understood that the scope of the present disclosure is not limited in any way by the scope of the following examples and preparations. In the following examples, and throughout the specification and claims, molecules with a single stereocenter, unless otherwise noted, exist as a racemic mixture. Those molecules with two or more stereocenters, unless otherwise noted, exist as a racemic mixture of diastereomers. Single enantiomers/diastereomers may be obtained by methods known to those skilled in the art.

EXAMPLES

The following examples are provided for exemplary purposes. Methods for preparation of compounds of structure (I) are known in the art or can be derived by one of ordinary skill in the art.

The in vivo efficacy of exemplary compounds of structure (I) in an established human AML, Breast, GBM xenograft growth inhibition experiments are conducted along with multi-kinase, targeted kinase reference agents, and standard chemotherapeutic agents/drugs. The potent and selective MELK, FLT3 inhibitors are administered orally in dose escalation in vivo experiments starting from 10, 20, 40, and 60 mg/Kg after 4-6 weeks of sub-cutaneous AML, breast and GBM cancer cells injection into mice.

Example 1

General Reaction: Exemplary Preparation of A2 (Method A)

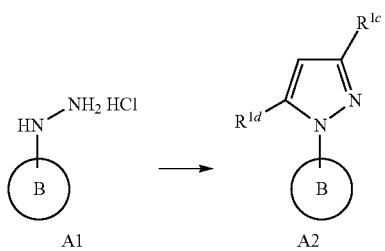

Method 1A—A solution of A1 (1 eq) and 1,1,3,3-tetramethoxypropane (1.1 eq) in ethanol (10 vol) was stirred at 90° C. for 16 h. The reaction mass was cooled to ambient temperature and concentrated in vacuo to remove ethanol (distillation of minor amount of product was observed in distilled solvent). The residue thus obtained was diluted with water and extracted with dichloromethane (2×). The combined organic layer was washed with saturated brine solution, dried over anhydrous sodium sulfate, filtered and concentrated to afford crude desired product A2.

Method 1B—The crude product obtained as above was purified by silica gel column chromatography to afford compound A2.

Example 2

General Reaction: Exemplary Preparation of A2' (Method A)

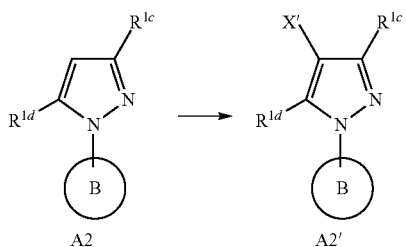

Method 2A—N-iodosuccinimide (1.4 eq) was added to a stirred solution of A2 (1 eq) in acetic acid (10 vol) at ambient temperature. The reaction mixture was stirred at 130° C. for 0.5 h. The reaction mass was cooled to ambient temperature, poured into ice-water and extracted with ethyl acetate (2×). The combined organic layer was washed with water, saturated brine solution, dried over anhydrous sodium sulfate, filtered and concentrated in vacuo. The crude product was purified by silica gel column chromatography to afford compound A2'.

Method 2B—N-iodosuccinimide (1.4 eq) was added to a stirred solution of A2 (1 eq) in acetic acid (10 vol) at ambient temperature. The reaction mixture was stirred at 120° C. for 0.5 h. The reaction mass was cooled to ambient temperature, poured into ice-water and extracted with dichloromethane (2×). The combined organic layer was washed with water, saturated brine solution, dried over anhydrous sodium sulfate, filtered and concentrated in vacuo to afford compound A2'.

Method 2C—N-iodosuccinimide (1 eq) was added to a stirred solution of A2 (1 eq) in acetic acid (10 vol) at ambient temperature. The reaction mixture was stirred at ambient temperature for 16 h. The reaction mass was poured into ice-water and extracted with dichloromethane (2×). The combined organic layer was washed with water, saturated brine solution, dried over anhydrous sodium sulfate, filtered and concentrated in vacuo to afford compound A2'.

Method 2D—N-iodosuccinimide (1.4 eq) was added to a stirred solution of A2 (1 eq) in acetic acid (10 vol) at ambient temperature. The reaction mixture was stirred at 130° C. for 0.5 h. The reaction mass was cooled to ambient temperature, poured into ice-water, and solid precipitated out. Obtained solid was filtered, washed with water and dried in vacuo to afford compound A2'.

Example 3

General Reaction. Exemplary Preparation of A3 (Method A)

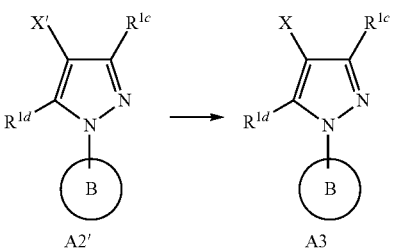

Method 3A—Pinacol borane (1.2 eq), triethylamine (2.5 eq), S-Phos (0.09 eq) and bis(acetonitrile)dichloropalladium (II) (0.03 eq) were added to a stirred solution of A2' (1 eq) in toluene (10 vol) at ambient temperature under nitrogen atmosphere. The reaction mixture was stirred at 90° C. for 16 h. The reaction mass was cooled to ambient temperature, quenched with saturated $NH_4C_1$ solution and extracted with dichloromethane (2×). The combined organic layer was washed with saturated brine solution, dried over anhydrous sodium sulfate, filtered and concentrated in vacuo. The crude product was purified by silica gel column chromatography to afford compound A3.

Method 3B— Bis(pinacolato)diboron (2 eq), Potassium acetate (3 eq) and [1,1'-bis(diphenylphosphino)ferrocene] dichloropalladium(II) or $PdCl_2$(dppf) (1:1) (0.1 eq) were added to a stirred solution of A2' (1 eq) in DMSO (10 vol) at ambient temperature under nitrogen atmosphere. The reaction mixture was stirred at 80° C. for 16 h. The reaction mass was cooled to ambient temperature, diluted with water and extracted with dichloromethane (2×). The combined organic layer was washed with saturated brine solution, dried over anhydrous sodium sulfate, filtered and concentrated in vacuo. The crude product was purified by silica gel column chromatography to afford compound A3.

Example 4

General Reaction: Exemplary Preparation of A5 (Method A)

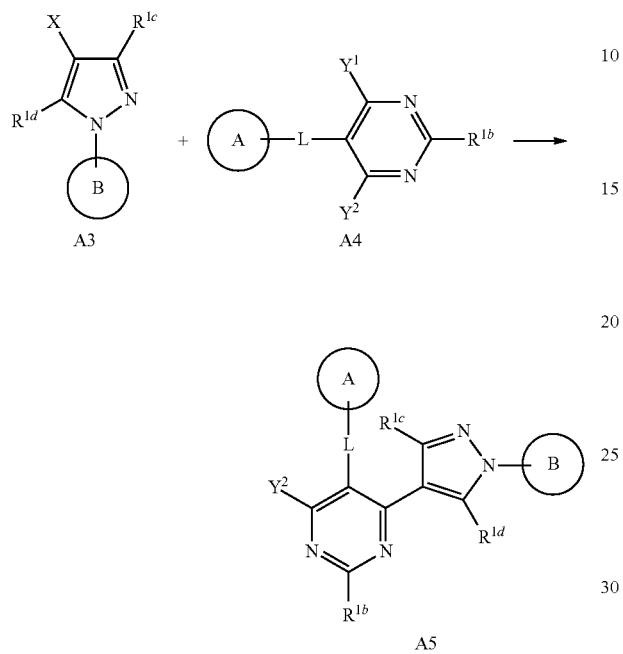

Method 4A—A3 (1.1 eq), $Na_2CO_3$ (2 eq) and [1,1'-Bis(diphenylphosphino)ferrocene]-dichloropalladium(II) (1:1) (0.1 eq) were added to a stirred solution of A4 (1 eq) in dioxane (9 vol) and water (1 vol) at ambient temperature under nitrogen atmosphere. The reaction mixture was stirred at 90° C. for 8 h. The reaction mass was cooled to ambient temperature and concentrated in vacuo. The crude product was purified by silica gel column chromatography to afford compound A5.

Example 5

General Reaction: Exemplary Preparation of A5' (Method A)

Method 5A—Palladium on carbon (10%) (10% by weight) and $NaHCO_3$ (2 eq) were added to a stirred solution of A5 (1 eq) in methanol (10 vol) at ambient temperature under a nitrogen atmosphere. The reaction mixture was stirred at ambient temperature under hydrogen atmosphere (Bladder) for 16 h. The reaction mass was filtered through celite bed, washed with methanol and the filtrate was concentrated in vacuo. The crude product was purified by silica gel column chromatography to afford compound A5'.

Example 6

General Reaction: Exemplary Preparation of Compound of Structure (I)

(METHOD A)

Structure (I)

Method 6A (deprotection)—2M hydrochloric acid in diethyl ether was added to a stirred solution of A5' in dichloromethane at 0° C. The reaction mixture was stirred at ambient temperature for 16 h. The reaction mass was concentrated in vacuo and the residue was lyophilized to afford a compound of structure (I).

Method 6B (deprotection)—2M hydrochloric acid in diethyl ether was added to a stirred solution of A5' in dichloromethane at 0° C. The reaction mixture was stirred at ambient temperature for 1 h. The reaction mass was filtered, solid washed with diethyl ether and dried in vacuo to afford a compound of Structure (I).

Example 7

General Reaction Exemplary Preparation of B3 (Method B)

Method 7A—B1 (1.1 eq), $K_2CO_3$ (2 eq) and tetrakis(triphenylphosphine)palladium (0.05 eq) were added to a stirred solution of B2 (1 eq) in dimethoxyethane (DME; 8 vol) and water (2 vol) at ambient temperature under nitrogen atmosphere. The reaction mixture was stirred at 90° C. for 16 h. The reaction mass was cooled to ambient temperature and concentrated in vacuo. The crude product was purified by silica gel column chromatography to afford compound B3.

Example 8

General Reaction Exemplary Preparation of (Protected) Compound of Structure (I) (Method B)

Method 8A—B4 (1.5 eq), Cs$_2$CO$_3$ (3 eq) and chloro(2-dicyclohexyl-phosphino-2',4',6'-triisopropyl-1,1'-biphenyl)[2-(2'-amino-1,1'-biphenyl)]-palladium(II) (0.1 eq) were added to a stirred solution of B3 (1 eq) in toluene (15 vol) at ambient temperature under nitrogen atmosphere. The reaction mixture was stirred at 130° C. for 40 h.

The reaction mass was cooled to ambient temperature and concentrated in vacuo. The crude product was purified by silica gel column chromatography to afford a protected form of a compound of structure (I).

Example 9

General Reaction Exemplary Deprotection of Compound of Structure (I)

Method 9A (deprotection)—2M hydrochloric acid in diethyl ether was added to a stirred solution of protected intermediate in dichloromethane at 0° C. The reaction mixture was stirred at ambient temperature for 3 h. The reaction mass was concentrated in vacuo and the residue was purified by prep HPLC afford a compound of structure (I).

Method 9B (deprotection)—2M hydrochloric acid in diethyl ether was added to a stirred solution of protected intermediate in dichloromethane at 0° C. The reaction mixture was stirred at ambient temperature for 3 h. The reaction mass was concentrated in vacuo and the residue was lyophilized to afford a compound of structure (I).

Example 10

General Procedure for Boc Protection of Amino Acid (Method 10A)

Method 10A: To an ice cold solution of an R-amino acid and K$_2$CO$_3$ in acetone/water mixture was added di-tertbutyl dicarbonate (boc-anhydride) and the reaction mixture was stirred at room temperature for 16 h. After reaction completion (TLC), acetone was removed in vacuo at a temperature not more than 50° C. and the aqueous layer was washed with hexane to remove any excess of boc-anhydride. The aqueous layer was then acidified with 1.5 N HCl (pH-5), and the solid formed was collected on a Buchner funnel, the cake was thoroughly washed with water and dried to afford the title compound as off white solid.

Example 11

General Procedure for Reduction of Boc Amino Acid to Alcohol (Method 11A)

Method 11A: A solution of an R—N-Boc amino acid obtained according to Example 10 and triethylamine (3.0 eq.) in dichloromethane (10 vol) was cooled to −40° C. and isobutyl chloroformate (1.1 eq) was added drop wise. The reaction mixture was warmed to room temperature and stirred for additional 1 h. After completion (TLC), the reaction mixture was neutralized with 1.5 N HCl and the crude product was extracted with dichloromethane. The organic phase was successively washed with water and brine, dried over Na$_2$SO$_4$, and concentrated in vacuo to afford crude mixed anhydride as light yellow gum. Sodium borohydride was added to the crude residue dissolved in THF (10 vol), at −30° C. Methanol was added slowly through an addition funnel at the same temperature during which effervescence slowly starts and the reaction mixture was warmed to room temperature and continued the stirring for additional 1 h. The reaction mixture was neutralized with 1.5N HCl and the crude product was extracted in ethyl acetate. The organic layer was successively washed with water and brine, dried over Na$_2$SO$_4$, concentrated, and purified to afford the title compound.

Example 12

Synthesis of Compound Intermediate 12

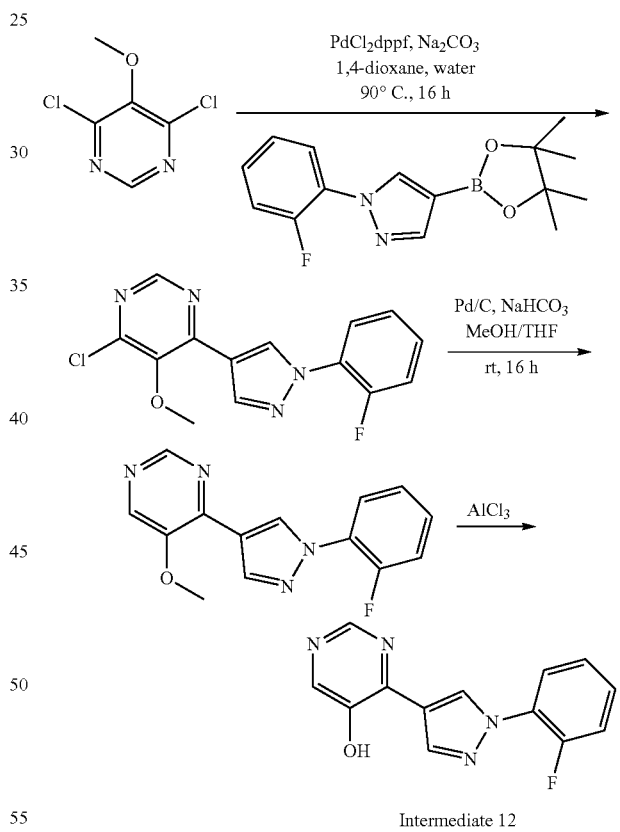

To a solution of 4,6-dichloro-5-methoxypyrimidine (3 g, 0.1675 mol), 1-(2-fluorophenyl)-4-(4,4,5,5-tetramethyl-1,3,2-dioxaborolan-2-yl)-1H-pyrazole (4.20 g, 0.01843 mol) and sodium carbonate (2.66 g, 0.02513 mol) in dioxane:water was added Pd(dppf)Cl$_2$. dichloromethane complex (50 mg, 0.0006 mol) and the reaction mixture was heated at 90° C. for 16 h. After the completion of reaction the crude was filtered through a celite bed and the filtrate was diluted with ethyl acetate thoroughly washed with water. The crude material obtained was purified by column chromatography (230-400 silica gel (10% EA/hexanes as an eluent) to afford the product as a brown solid.

Yield: 40% (2 g).
Appearance: Brown solid.
LC/MS: Calculated 304.71; Observed m/z [M+H]$^+$305.1.

To a solution of 4-chloro-6-(1-(2-fluorophenyl)-1H-pyrazol-4-yl)-5-methoxypyrimidine (6 g, 00197 mol) in THF:methanol (50 mL) was added sodium bicarbonate (3.31 g, 0.0394 mol) and 10% Pd/C (600 mg). The resulting mixture was stirred at RT under hydrogen atmosphere for 16 h. After completion of the reaction, the crude mixture was filtered through a celite bed and washed with methanol:ethyl acetate. The organic layer was concentrated in vacuo and the crude material was purified by column chromatography (230-400 silica gel (50% EA/hexanes as an eluent) to afford the product as an off white solid.

Yield: 75% (4 g).
Appearance: Off white solid.
LC/MS: Calculated 270.27; Observed m/z [M+H]$^+$271.1.

To a solution of 4-(1-(2-fluorophenyl)-1H-pyrazol-4-yl)-5-methoxypyrimidine (4 g, 0.01481 mol) in dichloroethane (DCE; 100 mL) at 0° C. was added aluminum trichloride (7.8 g, 0.02962 mol) in two portions. The reaction mixture was stirred at 0° C. for 10 min, then at 60° C. for 16 h. After completion, the reaction mixture cooled to 0° C. and quenched with aqueous 1M HCl (80 mL) followed by methanol (8 mL) added slowly while stirring vigorously. The mixture was poured into water (50 mL), the DCE layer separated, and the aqueous phase extracted with ethyl acetate. The combined organic layers were washed with brine, dried over sodium sulfate, filtered and concentrated. The crude material obtained was purified by column chromatography (230-400 silica gel (5% methanol/dichloromethane as an eluent) to afford the product as a colorless gum.

Yield: 63% (2.4 g).
Appearance: colorless gum.
LC/MS: Calculated 256.24; Observed m/z [M+H]$^+$257.1.

Example 13

Synthesis of Compound Intermediate 13

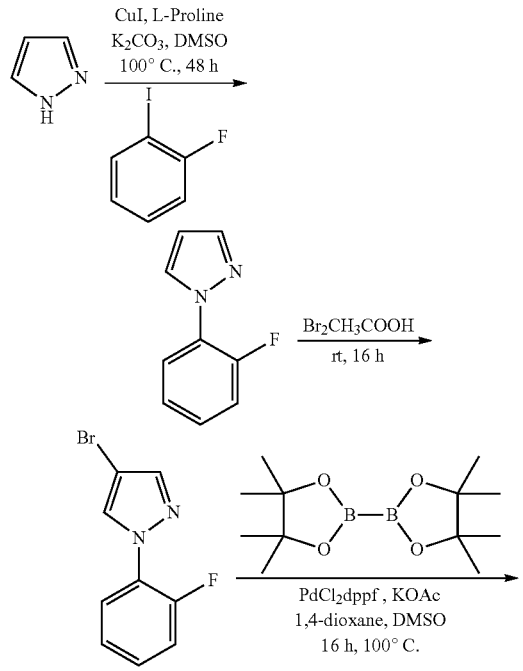

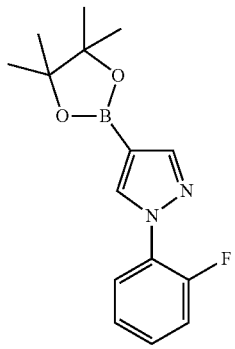

Intermediate 13

To a solution of 1-fluoro-2-iodobenzene (19.5 g, 87.8 mmol) in DMSO (40 mL) was added pyrazole (4 g, 58.8 mmol) followed by CuI (0.52 g, 2.73 mmol), L-proline (0.67 g, 5.217 mmol), and potassium carbonate (4.4 g, 31.88 mmol). The reaction mixture was heated to 100° C. for 48 h. The reaction mixture was cooled to room temperature, filtered through a celite bed and the filtrate was extracted with dichloromethane. The organic layer was concentrated and the residue was purified by flash column chromatography to yield 1-(2-fluorophenyl)-1H-pyrazole (3 g, 33% yield).

LC/MS APC: Calculated 162.06 Observed m/z [M+H]$^+$ 163.2.

$^1$H-NMR 400 MHz, DMSO-d$_6$: δ 8.21 (d, J=5.60 Hz, 1H), 7.81 (t, J=8.00 Hz, 1H), 7.80-7.78 (m, 1H), 7.50-7.34 (m, 3H), 6.58 (d, J=4.00 Hz, 1H).

To solution of 1-(2-fluorophenyl)-1H-pyrazole in acetic acid (5 mL) was added bromine (3 g, 18.5 mmol) in acetic acid (10 mL) at 0° C. The reaction mixture was stirred at room temperature for 16 h. The reaction mixture was cooled to room temperature, poured into ice and H$_2$O in a 100 mL beaker and excess saturated, aqueous NaHCO$_3$ was added until all the acetic acid had been quenched. Ethyl acetate (50 mL) was added and the layers were separated. The aqueous layer was extracted with ethyl acetate twice and the combined organics were dried over Na$_2$SO$_4$ and concentrated in vacuo to give a crude solid which was purified by flash column chromatography (SiO$_2$, 1:1 hexanes-ethyl acetate) to give 4-bromo-1-(2-fluorophenyl)-1H-pyrazole (2 g, 46% yield).

LC/MS APC: Calculated Observed m/z [M+H]$^+$241.2.

$^1$H-NMR 400 MHz, DMSO-d$_6$: δ 8.48 (s, 1H), 7.94 (s, 1H), 7.64 (t, J=8.00 Hz, 1H), 7.52-7.47 (m, 2H), 7.39-7.36 (m, 1H).

A mixture of 4-bromo-1-(2-fluorophenyl)-1H-pyrazole (3.0 g, 12.4 mmol), potassium acetate (2.43 g, 24.7 mmol), bis(pinacolato)diboron (3.77 g, 14.9 mmol) and Pd(dppf)Cl$_2$ (0.9 g, 1.23 mmol) was suspended in DMSO (4 mL) and 1,4-dioxane (15 mL). The system was exchanged with N$_2$. The mixture was stirred at 100° C. for 16 h. The reaction mixture was diluted with water (60 mL). The resulting mixture was extracted with dichloromethane (50 mL×3). The combined organic layers were washed with saturated aqueous NaCl (15 mL), dried over anhydrous Na$_2$SO$_4$ and concentrated in vacuo. The residue was purified by silica gel column chromatography eluted with 20:1 hexanes/ethyl acetate to give 1-(2-fluorophenyl)-4-(4,4,5,5-tetramethyl-1,3,2-dioxaborolan-2-yl)-1H-pyrazole (2.0 g, 58% yield).

LC/MS APC: Calculated 288.14 Observed m/z [M+H]$^+$ 289.1.

¹H-NMR 400 MHz, DMSO-d₆: δ 8.35 (s, 1H), 7.91 (s, 1H), 7.80 (t, J=8.00 Hz, 1H), 7.51-7.44 (m, 2H), 7.39-7.34 (m, 1H), 1.25 (s, 12H).

Example 14

Synthesis of Compound I-1

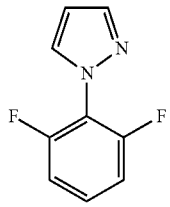

Using Method 1A, 4.0 g of (2,6-difluorophenyl)hydrazine hydrochloride was converted into 1-(2,6-difluorophenyl)-1H-pyrazole.

Yield (96%): 3.8 g.
Appearance: Pale brown liquid.
LC/MS: Calculated 180.16; Observed m/z [M+H]⁺180.9.
LC/MS purity: 68.32%.

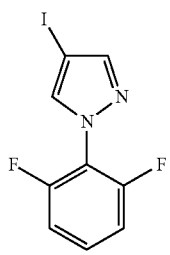

Using Method 2A, 3.8 g of 1-(2,6-difluorophenyl)-1H-pyrazole was converted into 1-(2,6-difluorophenyl)-4-iodo-1H-pyrazole.

Yield (62%): 4.0 g.
Appearance: Pale brown liquid.
LC/MS: Calculated 306.05; Observed m/z [M+H]⁺307.0.
LC/MS purity: 97.53%.

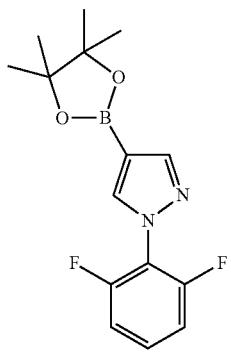 [SMILES: CC1(C)OB(c2cnn(-c3c(F)cccc3F)c2)OC1(C)C]

Using Method 3A, 4.0 g of 1-(2,6-difluorophenyl)-4-iodo-1H-pyrazole was converted into 1-(2,6-difluorophenyl)-4-(4,4,5,5-tetramethyl-1,3,2-dioxaborolan-2-yl)-1H-pyrazole.

Yield (63%): 2.5 g.
Appearance: Pale brown solid.
LC/MS: Calculated 306.12; Observed m/z [M+H]⁺307.3.
LC/MS purity: 75.14%.

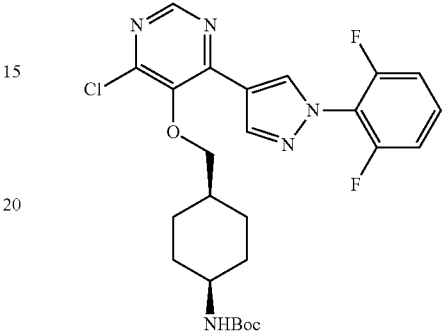

Using Method 4A, 447 mg of 1-(2,6-difluorophenyl)-4-(4,4,5,5-tetramethyl-1,3,2-dioxaborolan-2-yl)-1H-pyrazole was converted into tert-butyl (((1s, 4s)-4-(((4-chloro-6-(1-(2,6-difluorophenyl)-1H-pyrazol-4-yl)pyrimidin-5-yl)oxy)methyl)cyclohexyl)carbamate.

Yield (43%): 300 mg.
Appearance: White solid.
LC/MS: Calculated 519.98; Observed m/z [M+H]⁺520.2.
LC/MS purity: 92.50%.

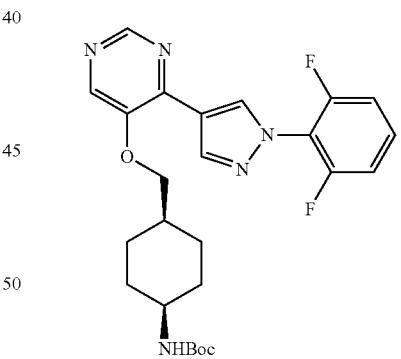

Using Method 5A, 300 mg of tert-butyl (((1s, 4s)-4-(((4-chloro-6-(1-(2,6-difluorophenyl)-1H-pyrazol-4-yl)pyrimidin-5-yl)oxy)methyl)cyclohexyl)carbamate was converted into tert-butyl (((1s, 4s)-4-(((4-(1-(2,6-difluorophenyl)-1H-pyrazol-4-yl)pyrimidin-5-yl)oxy)-methyl)cyclohexyl)carbamate.

Yield (54%): 150 mg.
Appearance: White solid.
LC/MS: Calculated 485.54; Observed m/z [M+H]⁺486.3.
LC/MS purity: 99.91%.

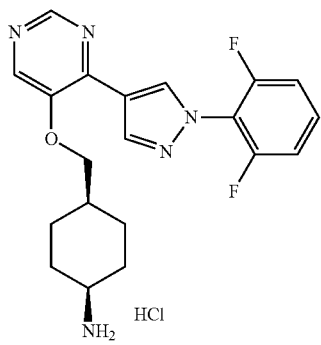

Using Method 6A, 150 mg of tert-butyl ((1s, 4s)-4-(((4-(1-(2,6-difluorophenyl)-1H-pyrazol-4-yl)pyrimidin-5-yl)oxy)methyl)cyclohexyl)carbamate was converted into (1s, 4s)-4-(((4-(1-(2,6-difluorophenyl)-1H-pyrazol-4-yl)pyrimidin-5-yl)oxy)methyl)-cyclohexan-1-amine hydrochloride.
Yield (100%): 130 mg.
Appearance: Off white solid.
LC/MS: Calculated 421.88; Observed m/z [M+H]$^+$386.1.
HPLC purity: 99.05%.

Example 15

Preparation of Compound I-2

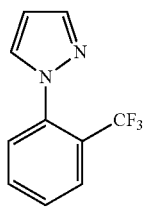

Using Method 1A (Example 1), 4.5 g of (2-(trifluoromethyl)phenyl)hydrazine hydrochloride was converted into 1-(2-(trifluoromethyl)phenyl)-1H-pyrazole.
Yield (90%): 4.0 g.
Appearance: Pale brown liquid.
LC/MS: Calculated 212.18; Observed m/z [M+H]$^+$213.1.
LC/MS purity: 87.78%.

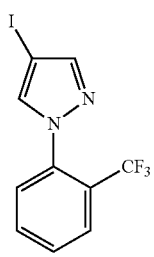 [SMILES: FC(F)(F)c1ccccc1-n1cc(I)cn1]

Using Method 2B, 4 g of 1-(2-(trifluoromethyl)phenyl)-1H-pyrazole was converted into 4-iodo-1-(2-(trifluoromethyl)phenyl)-1H-pyrazole.
Yield (79%): 4.8 g.
Appearance: Pale brown solid.
LC/MS: Calculated 338.07; Observed m/z [M+H]$^+$339.0.
LC/MS purity—98.74%.

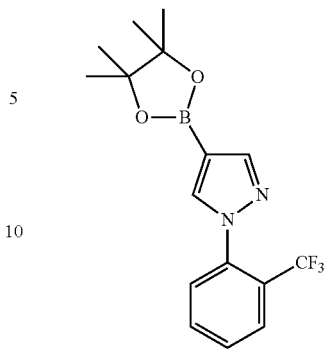

Using Method 3A, 4.8 g of 4-iodo-1-(2-(trifluoromethyl)phenyl)-1H-pyrazole was converted into 4-(4,4,5,5-tetramethyl-1,3,2-dioxaborolan-2-yl)-1-(2-(trifluoromethyl)-phenyl)-1H-pyrazole.
Yield (63%): 3 g.
Appearance: Pale brown gummy solid.
LC/MS: Calculated 338.14; Observed m/z [M+H]+ 339.1.
LC/MS purity: 82.42%.

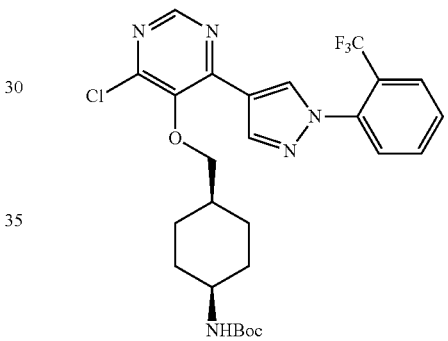

Using Method 4A, 493 mg of 4-(4,4,5,5-tetramethyl-1,3,2-dioxaborolan-2-yl)-1-(2-(trifluoromethyl)phenyl)-1H-pyrazole was converted into tert-butyl ((1s, 4s)-4-(((4-chloro-6-(1-(2-(trifluoromethyl)phenyl)-1H-pyrazol-4-yl)pyrimidin-5-yl)oxy)methyl)cyclohexyl)-carbamate.
Yield (34%): 250 mg.
Appearance: White solid.
LC/MS: Calculated 552.00; Observed m/z [M+H]$^+$552.2.
LC/MS purity: 91.55%.

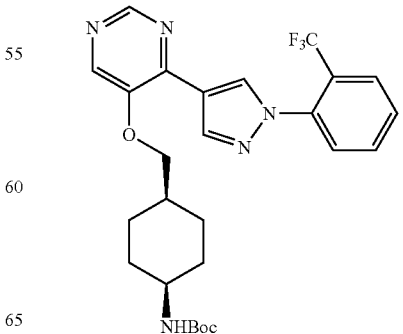

Using Method 5A, 250 mg of tert-butyl ((1s, 4s)-4-(((4-chloro-6-(1-(2-(trifluoromethyl)phenyl)-1H-pyrazol-4-yl)pyrimidin-5-yl)oxy)methyl)cyclohexyl)carbamate was converted into tert-butyl ((1s, 4s)-4-(((4-(1-(2-(trifluoromethyl)phenyl)-1H-pyrazol-4-yl)-pyrimidin-5-yl)oxy)methyl)cyclohexyl)carbamate.

Yield (85%): 200 mg.
Appearance: White solid.
LC/MS: Calculated 517.55; Observed m/z [M+H]$^+$518.1.
LC/MS purity: 99.75%.

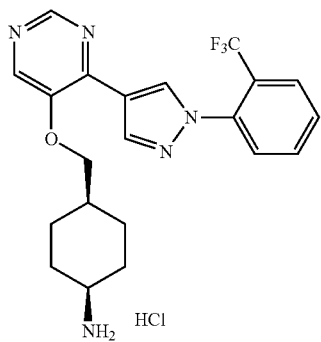 [SMILES: N[C@H]1CC[C@@H](COc2cncnc2-c2cnn(-c3ccccc3C(F)(F)F)c2)CC1 ; Cl]

Using Method 6A, 200 mg of tert-butyl ((1s, 4s)-4-(((4-(1-(2-(trifluoromethyl)phenyl)-1H-pyrazol-4-yl)pyrimidin-5-yl)oxy)methyl)cyclohexyl)carbamate was converted into ((1s, 4s)-4-(((4-(1-(2-(trifluoromethyl)phenyl)-1H-pyrazol-4-yl)pyrimidin-5-yl)-oxy)methyl)cyclohexan-1-amine hydrochloride.

Yield (100%): 180 mg.
Appearance: Pale brown solid.
LC/MS: Calculated 453.89; Observed m/z [M+H]$^+$418.1.
HPLC purity: 99.40%.

Example 16

Synthesis of Compound I-3

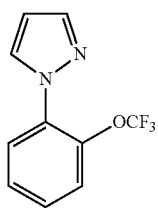

Using Method 1A, 2 g of (2-(trifluoromethoxy)phenyl) hydrazine hydrochloride was converted into 1-(2-(trifluoromethoxy)phenyl)-1H-pyrazole.

Yield (100%): 2 g.
Appearance: Pale brown liquid.
LC/MS: Calculated 228.17; Observed m/z [M+H]$^+$229.1.
LC/MS purity: 94.19%.

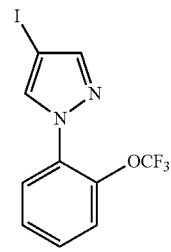 [SMILES: FC(F)(F)Oc1ccccc1-n1cc(I)cn1]

Using Method 2C, 1.0 g of 1-(2-(trifluoromethoxy)phenyl)-1H-pyrazole was converted into 4-iodo-1-(2-(trifluoromethoxy)phenyl)-1H-pyrazole.

Yield (72%): 1.1 g.
Appearance: Pale brown liquid.
LC/MS: Calculated 354.07; Observed m/z [M+H]$^+$355.0.
LC/MS purity: 58.62%.

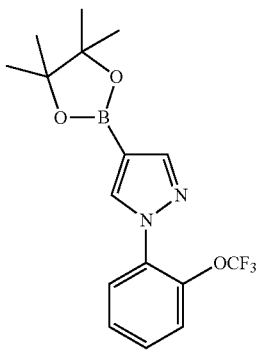 [SMILES: CC1(C)OB(c2cnn(-c3ccccc3OC(F)(F)F)c2)OC1(C)C]

Using Method 3B, 1.1 g of 4-iodo-1-(2-(trifluoromethoxy)phenyl)-1H-pyrazole was converted into 4-(4,4,5,5-tetramethyl-1,3,2-dioxaborolan-2-yl)-1-(2-(trifluoromethoxy)-phenyl)-1H-pyrazole.

Yield (54%): 600 mg.
Appearance: Pale brown solid.
LC/MS: Calculated 354.14; Observed m/z [M+H]$^+$355.1.
LC/MS purity: 87.77%.

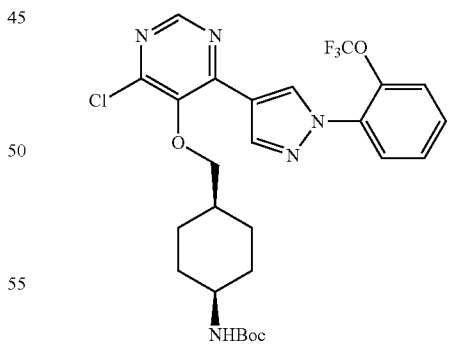

Using Method 4A, 600 mg of 4-(4,4,5,5-tetramethyl-1,3,2-dioxaborolan-2-yl)-1-(2-(trifluoromethoxy)phenyl)-1H-pyrazole was converted into tert-butyl ((1s, 4s)-4-(((4-chloro-6-(1-(2-(trifluoromethoxy)phenyl)-1H-pyrazol-4-yl)pyrimidin-5-yl)oxy)methyl)cyclohexyl)-carbamate.

Yield (33%): 300 mg.
Appearance: White solid.
LC/MS: Calculated 567.99; Observed m/z [M+H]$^+$568.2.
LC/MS purity: 98.97%.

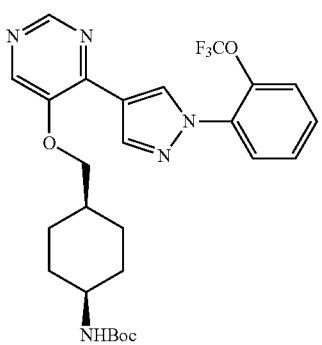 [SMILES: CC(C)(C)OC(=O)N[C@H]1CC[C@@H](COc2cncnc2-c2cnn(-c3ccccc3OC(F)(F)F)c2)CC1]

Using Method 5A, 300 mg of tert-butyl ((1s, 4s)-4-(((4-chloro-6-(1-(2-(trifluoromethoxy)phenyl)-1H-pyrazol-4-yl)pyrimidin-5-yl)oxy)methyl)cyclohexyl)carbamate was converted into tert-butyl ((1s, 4s)-4-(((4-(1-(2-(trifluoromethoxy)phenyl)-1H-pyrazol-4-yl)-pyrimidin-5-yl)oxy)methyl)cyclohexyl)carbamate.

Yield (81%): 230 mg.
Appearance: White solid.
LC/MS: Calculated 533.55; Observed m/z [M+H]$^+$534.3.
LC/MS purity: 99.40%.

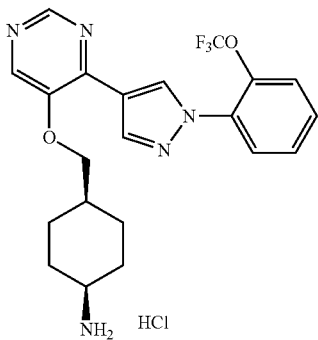 [SMILES: N[C@H]1CC[C@@H](COc2cncnc2-c2cnn(-c3ccccc3OC(F)(F)F)c2)CC1 ; Cl]

Using Method 6A, 230 mg of tert-butyl ((1s, 4s)-4-(((4-(1-(2-(trifluoromethoxy)phenyl)-1H-pyrazol-4-yl)pyrimidin-5-yl)oxy)methyl)cyclohexyl)carbamate was converted into (1s, 4s)-4-(((4-(1-(2-(trifluoromethoxy)phenyl)-1H-pyrazol-4-yl)pyrimidin-5-yl)-oxy)methyl)cyclohexan-1-amine hydrochloride.

Yield (99%): 200 mg.
Appearance: Off white solid.
LC/MS: Calculated 469.89; Observed m/z [M+H]$^+$434.1.
HPLC purity: 95.79%.

Example 17

Preparation of Compound I-4

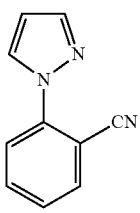

1H-pyrazole (1.12 g, 0.0165 mol, 1 eq) and K$_2$CO$_3$ (2.73 g, 0.0198, 1.2 eq) were added to a stirred solution of 2-fluorobenzonitrile (2 g, 0.165 mol, 1 eq) in DMF (30 mL) at ambient temperature. The reaction mixture was stirred at 120° C. for 16 h. The reaction mass was concentrated in vacuo and residue was diluted with water and extracted with ethyl acetate (2×75 mL). The combined organic layer was washed with water (100 mL), saturated brine solution (100 mL), dried over anhydrous sodium sulfate, filtered and concentrated in vacuo to afford 2-(1H-pyrazol-1-yl)benzonitrile.

Yield (89%): 2.5 g.
Appearance: Pale brown liquid.
LC/MS: Calculated 169.19; Observed m/z [M+H]$^+$170.1.
LC/MS purity: 99.15%0.

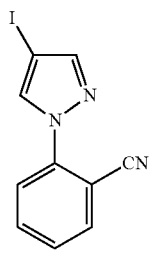 [SMILES: N#Cc1ccccc1-n1cc(I)cn1]

Using Method 2C, 2.5 g of 2-(1H-pyrazol-1-yl)benzonitrile was converted into 2-(4-iodo-1H-pyrazol-1-yl)benzonitrile.

Yield (69%): 3 g.
Appearance: Pale brown solid.
LC/MS: Calculated 295.08; Observed m/z [M+H]$^+$295.9.
LC/MS purity: 92.10%.

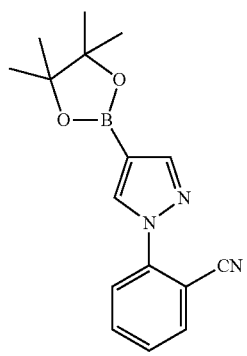 [SMILES: CC1(C)OB(c2cnn(-c3ccccc3C#N)c2)OC1(C)C]

Using Method 3B, 3 g of 2-(4-iodo-1H-pyrazol-1-yl)benzonitrile was converted into 2-(4-(4,4,5,5-tetramethyl-1,3,2-dioxaborolan-2-yl)-1H-pyrazol-1-yl)benzonitrile.

Yield (50%): 1.5 g.
Appearance: Pale brown solid.
LC/MS: Calculated 295.15; Observed m/z [M+H]$^+$296.2.
LC/MS purity: 57.56%.

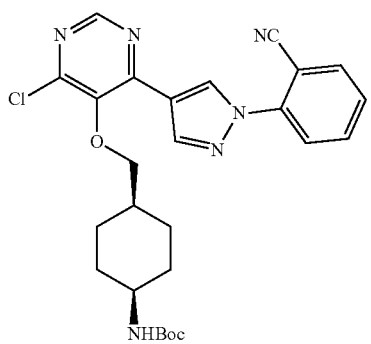 [SMILES: CC(C)(C)OC(=O)N[C@H]1CC[C@@H](COc2c(Cl)ncnc2-c2cnn(-c3ccccc3C#N)c2)CC1]

Using Method 4A, 431 mg of 2-(4-(4,4,5,5-tetramethyl-1,3,2-dioxaborolan-2-yl)-1H-pyrazol-1-yl)benzonitrile was converted into tert-butyl ((1s, 4s)-4-(((4-chloro-6-(1-(2-cyanophenyl)-1H-pyrazol-4-yl)pyrimidin-5-yl)oxy)methyl)cyclohexyl)carbamate.
Yield (44%): 300 mg.
Appearance: White solid.
LC/MS: Calculated 509.01; Observed m/z [M+H]⁺509.2.
LC/MS purity: 98.91%.

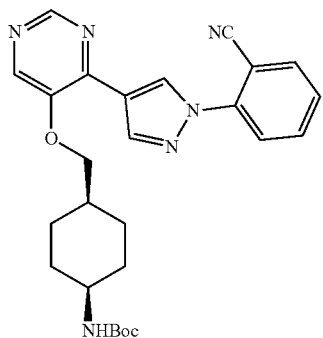 [SMILES: CC(C)(C)OC(=O)N[C@H]1CC[C@@H](COc2cncnc2-c2cnn(-c3ccccc3C#N)c2)CC1]

Using Method 5A, 150 mg of tert-butyl ((1s, 4s)-4-(((4-chloro-6-(1-(2-cyanophenyl)-1H-pyrazol-4-yl)pyrimidin-5-yl)oxy)methyl)cyclohexyl)carbamate was converted into tert-butyl ((1s, 4s)-4-(((4-(1-(2-cyanophenyl)-1H-pyrazol-4-yl)pyrimidin-5-yl)oxy)methyl)-cyclohexyl)carbamate.
Yield (72%): 100 mg.
Appearance: White solid.
LC/MS: Calculated 474.57; Observed m/z [M+H]⁺475.2.
LC/MS purity: 98.63%.

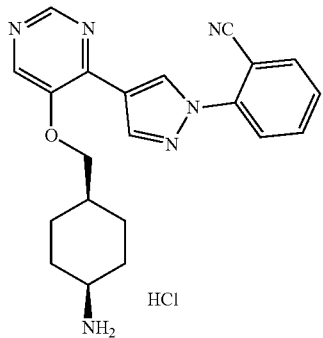 [SMILES: N#Cc1ccccc1-n1cc(-c2ncncc2OC[C@H]2CC[C@@H](N)CC2)cn1 ; Cl]

Using Method 6B, 80 mg of tert-butyl ((1s, 4s)-4-(((4-(1-(2-cyanophenyl)-1H-pyrazol-4-yl)pyrimidin-5-yl)oxy) methyl)cyclohexyl)carbamate was converted into 2-(4-(5-(((1s, 4s)-4-aminocyclohexyl)methoxy)pyrimidin-4-yl)-1H-pyrazol-1-yl)benzonitrile hydrochloride.
Yield (65%): 45 mg.
Appearance: Off white solid.
LC/MS: Calculated 410.91; Observed m/z [M+H]⁺375.2.
HPLC purity: 97.00%.

Example 18

Synthesis of Compound I-5

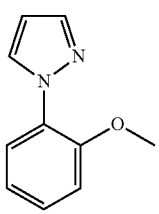

Using Method 1B, 4.5 g of (2-methoxyphenyl)hydrazine hydrochloride was converted into 1-(2-methoxyphenyl)-1H-pyrazole.
Yield (40%): 2.2 g.
Appearance: Pale brown liquid.
LC/MS: Calculated 174.20; Observed m/z [M+H]⁺175.1.
LC/MS purity: 98.56%.

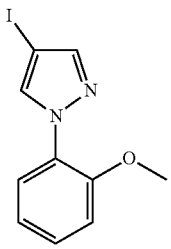

Using Method 2C, 2.0 g of 1-(2-methoxyphenyl)-1H-pyrazole was converted into 4-iodo-1-(2-methoxyphenyl)-1H-pyrazole.
Yield (73%): 2.5 g.
Appearance: Pale brown liquid.
LC/MS: Calculated 300.10; Observed m/z [M+H]⁺301.1.
LC/MS purity: 90.58%.

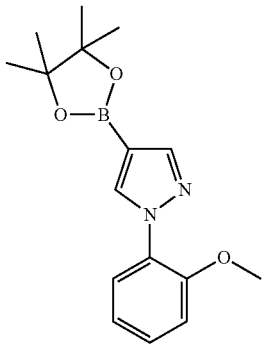

Using Method 3B, 1 g of 4-iodo-1-(2-methoxyphenyl)-1H-pyrazole was converted into 1-(2-methoxyphenyl)-4-(4,4,5,5-tetramethyl-1,3,2-dioxaborolan-2-yl)-1H-pyrazole.

Yield (60%): 600 mg.
Appearance: White solid.
LC/MS: Calculated 300.17; Observed m/z [M+H]⁺301.1.
LC/MS purity: 91.95%.

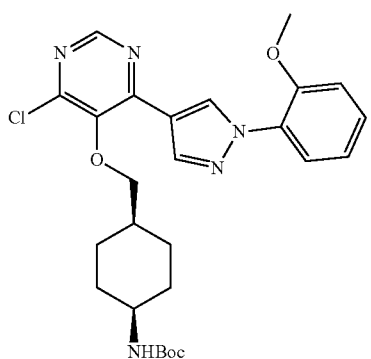 [SMILES: COc1ccccc1-n1cc(-c2ncnc(Cl)c2OC[C@H]2CC[C@@H](NC(=O)OC(C)(C)C)CC2)cn1]

Using Method 4A, 600 mg of 1-(2-methoxyphenyl)-4-(4,4,5,5-tetramethyl-1,3,2-dioxaborolan-2-yl)-1H-pyrazole was converted into tert-butyl ((1s, 4s)-4-(((4-chloro-6-(1-(2-methoxyphenyl)-1H-pyrazol-4-yl)pyrimidin-5-yl)oxy)methyl)cyclohexyl)carbamate.

Yield (34%): 350 mg.
Appearance: White solid.
LC/MS: Calculated 514.02; Observed m/z [M+H]⁺515.1.
LC/MS purity: 89.35%.

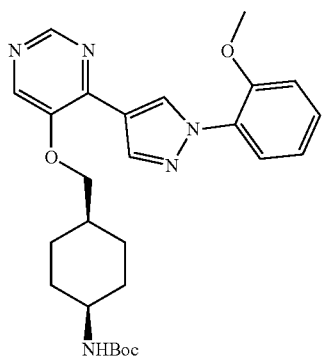 [SMILES: COc1ccccc1-n1cc(-c2ncncc2OC[C@H]2CC[C@@H](NC(=O)OC(C)(C)C)CC2)cn1]

Using Method 5A, 300 mg of tert-butyl ((1s, 4s)-4-(((4-chloro-6-(1-(2-methoxyphenyl)-1H-pyrazol-4-yl)pyrimidin-5-yl)oxy)methyl)cyclohexyl)carbamate was converted into tert-butyl ((1s, 4s)-4-(((4-(1-(2-methoxyphenyl)-1H-pyrazol-4-yl)pyrimidin-5-yl)oxy)-methyl)cyclohexyl)carbamate.

Yield (79%): 220 mg.
Appearance: White solid.
LC/MS: Calculated 479.58; Observed m/z [M+H]⁺480.3.
LC/MS purity—99.66%.

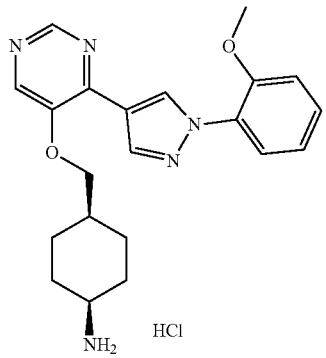 [SMILES: COc1ccccc1-n1cc(-c2ncncc2OC[C@H]2CC[C@@H](N)CC2)cn1 ; Cl]

Using Method 6A, 220 mg of tert-butyl ((1s, 4s)-4-(((4-(1-(2-methoxyphenyl)-1H-pyrazol-4-yl)pyrimidin-5-yl)oxy)methyl)cyclohexyl)carbamate was converted into (1s, 4s)-4-(((4-(1-(2-methoxyphenyl)-1H-pyrazol-4-yl)pyrimidin-5-yl)oxy)methyl)-cyclohexan-1-amine hydrochloride.

Yield (100%): 200 mg.
Appearance: Pale yellow solid.
LC/MS: Calculated 415.92; Observed m/z [M+H]⁺380.1.
HPLC purity: 99.60%.

Example 19

Synthesis of Compound I-6

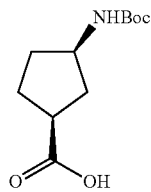 [SMILES: CC(C)(C)OC(=O)N[C@@H]1CC[C@H](C(=O)O)C1]

Using the Method 10A, 2 g of ((1S,3R)-3-aminocyclopentyl)(l1-oxidaneyl)methanone was converted into tert-butyl ((1R,3S)-3-((l1-oxidaneyl)carbonyl)cyclopentyl)carbamate.

Yield (75%): 1.6 g.
Appearance: Off white solid.
LC/MS: Calculated 228; Observed m/z 174 [M+H]-56.
LC/MS purity: 99%.

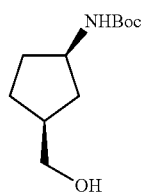 [SMILES: CC(C)(C)OC(=O)N[C@@H]1CC[C@H](CO)C1]

Using Method 11A, 2.0 g of tert-butyl ((1R,3S)-3-((l1-oxidaneyl)carbonyl)cyclopentyl) carbamate was converted into tert-butyl ((1R,3S)-3-(hydroxymethyl)cyclopentyl)carbamate.

Yield: (2.7 g, 75% yield).
Appearance: Off white solid.
LC/MS: Calculated 215.29; Observed m/z 160; [M+H-56].

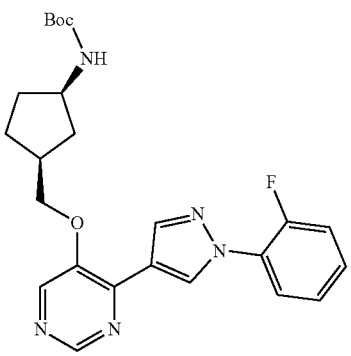 [SMILES: CC(C)(C)OC(=O)N[C@@H]1CC[C@H](COc2cncnc2-c2cnn(-c3ccccc3F)c2)C1]

Using the modified Mitsunobu procedure used to synthesize compound I-8, tert-butyl ((1R,3S)-3-(hydroxymethyl)cyclopentyl)carbamate (180 mg) was converted into tert-butyl ((1R,3S)-3-(((4-(1-(2-fluorophenyl)-1H-pyrazol-4-yl)pyrimidin-yl)oxy)methyl)cyclopentyl) carbamate.

Yield: (800 mg) crude containing triphenylphosphine impurity.
Appearance: Off white solid
LC/MS: Calculated 453.52; Observed m/z [M+H]$^+$454.2.

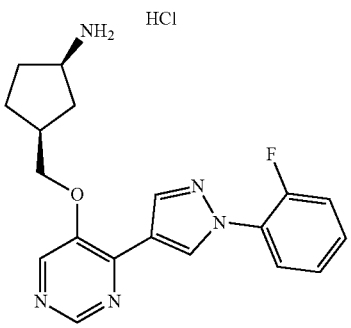 [SMILES: Cl ; N[C@@H]1CC[C@H](COc2cncnc2-c2cnn(-c3ccccc3F)c2)C1]

Using Method 6A, tert-butyl ((1R, 3S)-3-(((4-(1-(2-fluorophenyl)-1H-pyrazol-4-yl) pyrimidin-5-yl) oxy) methyl) cyclopentyl) carbamate (800 mg crude contain TPPO) was converted into (1R,3S)-3-(((4-(1-(2-fluorophenyl)-1H-pyrazol-4-yl)pyrimidin-5-yl)oxy)methyl) cyclopentan-1-amine hydro chloride.

Yield: (200 mg).
Appearance: White solid.
LC/MS: Calculated 389.86; Observed m/z [M+H]$^+$354.1.
HPLC purity: 95.31%.

Example 20

Synthesis of Compound I-7

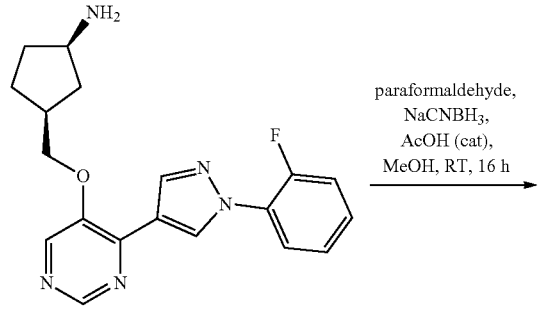

paraformaldehyde,
NaCNBH$_3$,
AcOH (cat),
MeOH, RT, 16 h

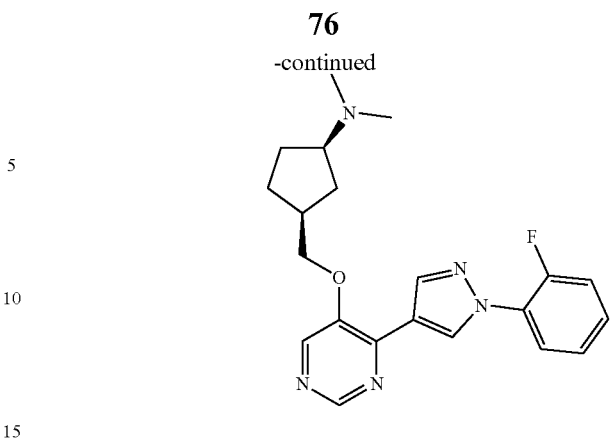

To a stirred solution of (1R, 3S)-3-(((4-(1-(2-fluorophenyl)-1H-pyrazol-4-yl) pyrimidin-5-yl) oxy) methyl) cyclopentan-1-amine (170 mg, 0.4810 mmol) in methanol was added paraformaldehyde (300 mg), NaCNBH$_3$ (200 mg) and AcOH (cat). The resulting mixture was stirred at room temperature for 16 h. After completion of the reaction, the mixture was filtered through a celite bed, the celite was washed with methanol and the combined organic layer was concentrated in vacuo. The crude material obtained was purified by preparative HPLC to afford as a gummy material which was dissolved in water and basified by saturated sodium bicarbonate solution and extracted with ethyl acetate. The combined organic layer was dried over sodium sulfate, filtered and concentrated to obtain as colorless gummy material.

Yield: 26.2% (48 mg).
Appearance: Colorless gum.
LC/MS: Calculated 381.46; Observed m/z [M+H]$^+$382.1.
HPLC purity: 94.24%.
$^1$H-NMR (400 MHz, DMSO-d$_6$): δ 8.86 (d, J=2.48 Hz, 1H), 8.78 (t, J=0.92 Hz, 1H), 4.64 (d, J=1.72 Hz, 1H), 8.50 (d, J=1.88 Hz, 1H), 7.93 (t, J=8.00 Hz, 1H), 7.48-7.54 (m, 2H), 7.40-7.44 (m, 1H), 4.21 (d, J=6.72 Hz, 2H), 2.42-2.51 (m, 1H), 2.07-2.12 (m, 7H), 1.80-1.89 (m, 3H), 1.48-1.58 (m, 2H), 1.25 (d, J=11.20 Hz, 1H).

Example 21

Synthesis of Compound I-8

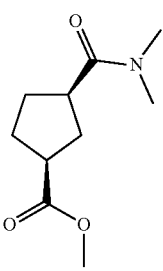

To an ice cold solution of (1R,3S)-3-(methoxycarbonyl)cyclopentane-1-carboxylic acid (2 g, 11.6 mmol), dimethylamine.HCl (1.22 g, 15.12 mmol) and triethylamine (3.5 g, 35 mmol) in dichloromethane (20 mL) was added propylphosphonic anhydride (T3P, 5.5 g, 17.4 mmol) and the mixture was stirred at room temperature for 16 h. The reaction mixture was diluted with water and the crude product was extracted with dichloromethane. The combined extracts were concentrated and purified by column chromatography to afford methyl (1S,3R)-3-(dimethylcarbamoyl) cyclopentane-1-carboxylate as off white solid.

Yield: (1.6 g, 70% yield).

LC/MS: Calculated 199.15; Observed m/z 200; [M+H].

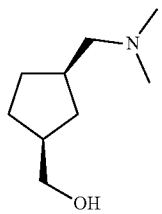

To an ice cold solution of methyl (S, 3R)-3-(dimethylcarbamoyl) cyclopentane-1-carboxylate (1.5 g, 7.5 mmol) in THF (20 mL) was added LAH (7.5 mL, 2M in THF, 15 mmol) and the reaction mixture was stirred at room temperature for 16 h. The reaction mixture was quenched with ethyl acetate/ice and the crude product was extracted with ethyl acetate. The combined extracts were concentrated and purified by column chromatography to afford ((1S, 3R)-3-((dimethylamino) methyl)cyclopentyl)methanol as pale brown liquid.

Yield: (0.7 g, 45% yield).

LC/MS: Calculated 157.26; Observed m/z 158.26 [M+H].

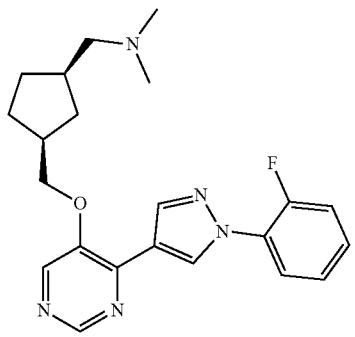 [SMILES: CN(C)C[C@@H]1CC[C@H](COc2cncnc2-c2cnn(-c3ccccc3F)c2)C1]

To a solution of 4-(1-(2-fluorophenyl)-1H-pyrazol-4-yl) pyrimidin-5-ol (100 mg, 0.3902 mmol) in Toluene (3 mL) were added ((1R,3S)-3-((dimethylamine) methyl)cyclopentyl)methanol (67.50 mg, 0.4292 mmol) and (cyanomethylene)tributylphosphorane (CMBP, modified Mitsunobu reaction, 117.46 mg, 0.4866 mmol) at 0° C., the mixture was stirred at 100° C. for 18 h. The organic layer was concentrated in vacuo. The crude material obtained was purified by preparative HPLC.

Yield: 23.2% (36 mg).

Appearance: Colorless gum.

LC/MS: Calculated 395.48; Observed m/z [M+H]⁺396.3.

HPLC purity: 99.45%.

Example 22

Preparation of Compound I-9

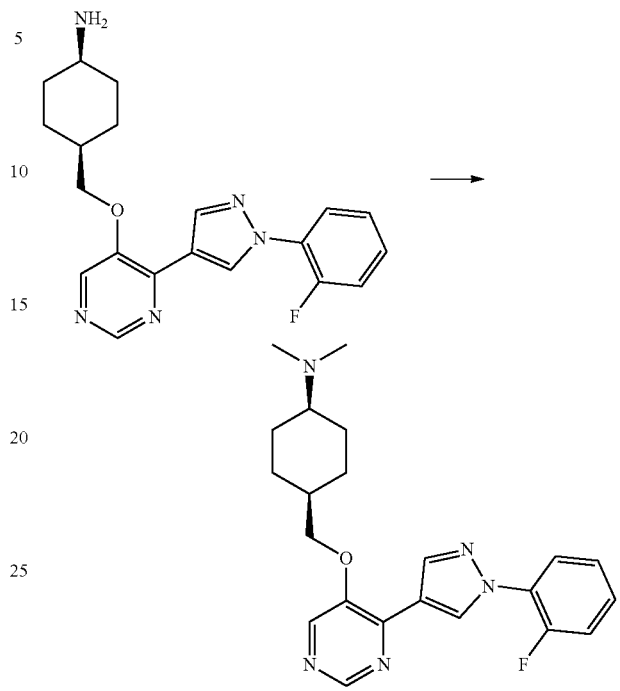

Paraformaldehyde (75 mg) and Na(OAc)₃BH (259 mg, 1.224 mmol, 6 eq) were added to a stirred solution of (1s, 4s)-4-(((4-(1-(2-fluorophenyl)-1H-pyrazol-4-yl)pyrimidin-5-yl)oxy)methyl)cyclohexan-1-amine (75 mg, 0.204 mmol, 1 eq) in AcOH (2 mL) and ethanol (2 mL) at ambient temperature. Reaction mixture was stirred at 100° C. for 48 h. The reaction mass was cooled to ambient temperature and concentrated in vacuo. The residue thus obtained was diluted with water (20 mL) and extracted with dichloromethane (2×30 mL). The combined organic layer was washed with saturated brine solution, dried over anhydrous sodium sulfate, filtered and concentrated in vacuo.

The crude product was purified by prep HPLC afford compound I-9.

Yield (18%): 15 mg.

Appearance: Off white solid

LC/MS: Calculated 395.48; Observed m/z [M+H]⁺396.1.

HPLC purity: 99.03%.

Example 23

Synthesis of Compound I-10

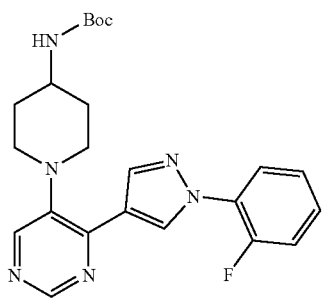 [SMILES: CC(C)(C)OC(=O)NC1CCN(c2cncnc2-c2cnn(-c3ccccc3F)c2)CC1]

Using Method 8A, 300 mg of 5-chloro-4-(1-(2-fluorophenyl)-1H-pyrazol-4-yl)pyrimidine was converted into tert-butyl (1-(4-(1-(2-fluorophenyl)-1H-pyrazol-4-yl)pyrimidin-5-yl)piperidin-4-yl)carbamate.
Yield (7%): 30 mg.
Appearance: White solid.
LC/MS: Calculated 438.51; Observed m/z [M+H]$^+$439.2.
LC/MS purity: 59.64%.

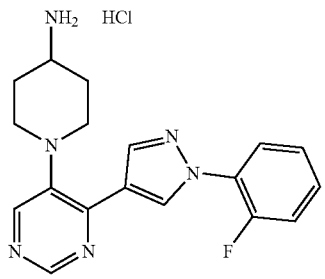 [SMILES: NC1CCN(c2cncnc2-c2cnn(-c3ccccc3F)c2)CC1 ; Cl]

Using Method 9B, 30 mg of tert-butyl (1-(4-(1-(2-fluorophenyl)-1H-pyrazol-4-yl)pyrimidin-5-yl)piperidin-4-yl)carbamate was converted into 1-(4-(1-(2-fluorophenyl)-1H-pyrazol-4-yl)pyrimidin-5-yl)piperidin-4-amine hydrochloride.
Yield (100%): 25 mg.
Appearance: Pale yellow solid.
LC/MS: Calculated 374.85; Observed m/z [M+H]$^+$339.0.
HPLC purity: 99.61%.

Example 24

Synthesis of Compound I-11

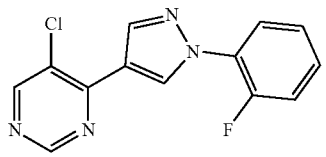 [SMILES: Fc1ccccc1-n1cc(-c2ncncc2Cl)cn1]

Using Method 7A, 1.0 g of 4,5-dichloropyrimidine was converted into 5-chloro-4-(1-(2-fluorophenyl)-1H-pyrazol-4-yl)pyrimidine.
Yield (43%): 0.8 g.
Appearance: White solid.
LC/MS: Calculated 274.68; Observed m/z [M+H]$^+$275.0.
LC/MS purity: 99.14%.

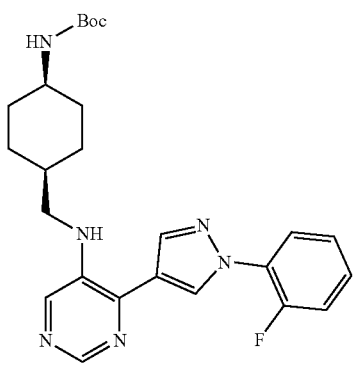 [SMILES: CC(C)(C)OC(=O)N[C@H]1CC[C@@H](CNc2cncnc2-c2cnn(-c3ccccc3F)c2)CC1]

Using Method 8A, 200 mg of 5-chloro-4-(1-(2-fluorophenyl)-1H-pyrazol-4-yl)pyrimidine was converted into tert-butyl ((1s, 4s)-4-(((4-(1-(2-fluorophenyl)-1H-pyrazol-4-yl)-pyrimidin-5-yl)amino)methyl)cyclohexyl)carbamate.

Yield (29%): 100 mg.

Appearance: Pale brown gummy solid.

LC/MS: Calculated 466.56; Observed m/z [M+H]$^+$467.3.

LC/MS purity: 91.69%.

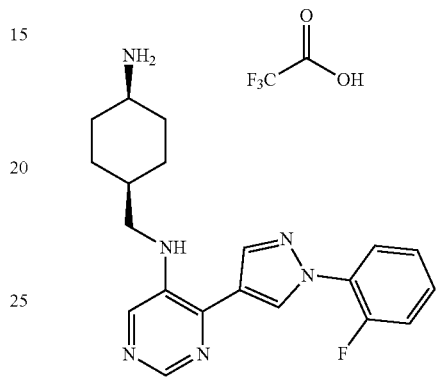

Using Method 9A, 100 mg of tert-butyl ((1s, 4s)-4-(((4-(1-(2-fluorophenyl)-1H-pyrazol-4-yl)pyrimidin-5-yl)amino)methyl)cyclohexyl)carbamate was converted into N-(((1s, 4s)-4-aminocyclohexyl)methyl)-4-(1-(2-fluorophenyl)-1H-pyrazol-4-yl)pyrimidin-5-amine trifluoroacetate.

Yield (45%): 50 mg.

Appearance: Pale yellow solid.

LC/MS: Calculated 480.47; Observed m/z [M+H]$^+$367.2.

HPLC purity: 99.28%.

Example 25

Synthesis of Compound I-12

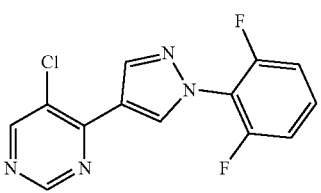 [SMILES: Fc1cccc(F)c1-n1cc(-c2ncncc2Cl)cn1]

Using Method 7A, 500 mg of 4,5-dichloropyrimidine was converted into 5-chloro-4-(1-(2,6-difluorophenyl)-1H-pyrazol-4-yl)pyrimidine.

Yield (51%): 500 mg.

Appearance: White solid.

LC/MS: Calculated 292.67; Observed m/z [M+H]$^+$293.0.

LC/MS purity: 99.19%.

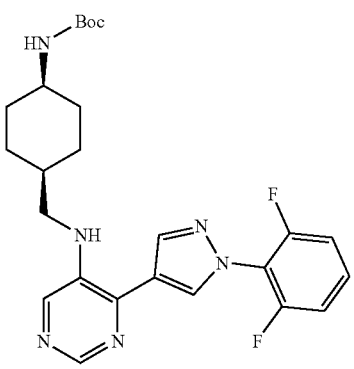 [SMILES: CC(C)(C)OC(=O)N[C@H]1CC[C@@H](CNc2cncnc2-c2cnn(-c3c(F)cccc3F)c2)CC1]

Using Method 8A, 300 mg of 5-chloro-4-(1-(2,6-difluorophenyl)-1H-pyrazol-4-yl)pyrimidine was converted into tert-butyl ((1s, 4s)-4-(((4-(1-(2,6-difluorophenyl)-1H-pyrazol-4-yl)pyrimidin-5-yl)amino)methyl)cyclohexyl)carbamate.
Yield (8%): 40 mg.
Appearance: Pale brown solid.
LC/MS: Calculated 484.55; Observed m/z [M+H]$^+$485.3.
LC/MS purity: 75.46%.

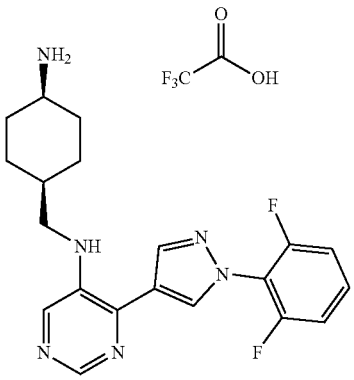 [SMILES: N[C@H]1CC[C@@H](CNc2cncnc2-c2cnn(-c3c(F)cccc3F)c2)CC1 ; O=C(O)C(F)(F)F]

Using Method 9A, 40 mg of tert-butyl ((1s, 4s)-4-(((4-(1-(2,6-difluorophenyl)-1H-pyrazol-4-yl)pyrimidin-5-yl)amino)methyl)cyclohexyl)carbamate was converted into N-(((1s, 4s)-4-aminocyclohexyl)methyl)-4-(1-(2,6-difluorophenyl)-1H-pyrazol-4-yl)-pyrimidin-5-amine trifluoroacetate.
Yield (60%): 25 mg.
Appearance: Pale yellow solid.
LC/MS: Calculated 498.2; Observed m/z [M+H]$^+$385.0 (no trifluoracetate ion).
HPLC purity: 97.70%.

Example 26

Synthesis of Compound I-13

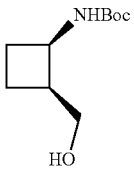 [SMILES: CC(C)(C)OC(=O)N[C@@H]1CC[C@@H]1CO]

Using Method 11A, 0.22 g of (1S,2R)-2-((tert-butoxycarbonyl)amino)cyclobutane-1-carboxylic acid was converted into tert-butyl ((1R,2S)-2-(hydroxymethyl) cyclobutyl) carbamate.
Yield (14%): 30 mg. It was taken as such for the next step without any purification.

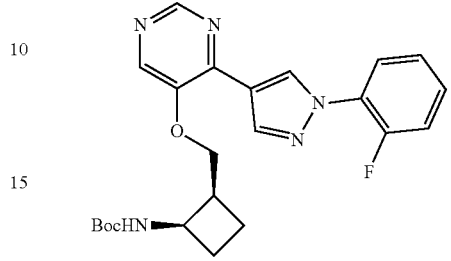

Using Method 11A, 0.03 g of tert-butyl ((1R,2S)-2-(hydroxymethyl) cyclobutyl)carbamate was converted into tert-butyl ((1R,2S)-2-(((4-(1-(2-fluorophenyl)-1H-pyrazol-4-yl)pyrimidin-5-yl)-oxy)methyl) cyclobutyl)carbamate.
Yield (38%): 25 mg. It was taken as such for the next step without any purification.

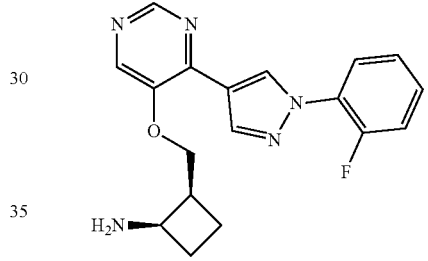

Using Method 6A, 0.03 g of tert-butyl ((1R,2S)-2-(((4-(1-(2-fluorophenyl)-1H-pyrazol-4-yl)pyrimidin-5-yl)oxy) methyl) cyclobutyl)carbamate was converted into (1R,2S)-2-(((4-(1-(2-fluorophenyl)-1H-pyrazol-4-yl)pyrimidin-5-yl)oxy)-methyl)-cyclobutan-1-amine (HCl salt).
Yield (78%): 15 mg.
Appearance: Off white solid.
LC/MS: Calculated 339.37; Observed m/z 340 [M+H].

Example 27

Preparation of Compound I-14

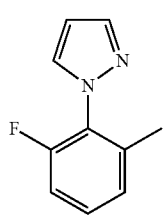

Using Method 1B, 3.0 g of (2-fluoro-6-methylphenyl) hydrazine hydrochloride was converted into 1-(2-fluoro-6-methylphenyl)-1H-pyrazole.
Yield (46%): 1.4 g.
Appearance: Pale brown liquid.
LC/MS: Calculated 176.19; Observed m/z [M+H]$^+$177.1.
LC/MS purity: 97.71%.

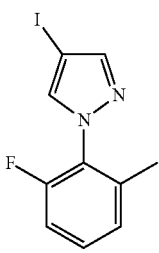

Using Method 2C, 1.4 g of 1-(2-fluoro-6-methylphenyl)-1H-pyrazole was converted into 1-(2-fluoro-6-methylphenyl)-4-iodo-1H-pyrazole.
Yield (67%): 1.6 g.
Appearance: Pale brown liquid.
LC/MS: Calculated 302.09; Observed m/z [M+H]⁺303.0.
LC/MS purity: 89.86%.

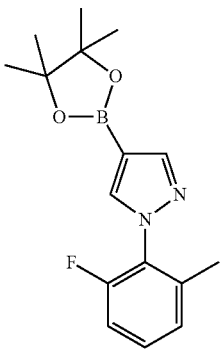

Using Method 3B, 1.6 g of 1-(2-fluoro-6-methylphenyl)-4-iodo-1H-pyrazole was converted into 1-(2-fluoro-6-methylphenyl)-4-(4,4,5,5-tetramethyl-1,3,2-dioxaborolan-2-yl)-1H-pyrazole.
Yield (62%): 1 g.
Appearance: Pale brown liquid.
LC/MS: Calculated 302.16; Observed m/z [M+H]⁺303.2.
LC/MS purity: 95.28%.

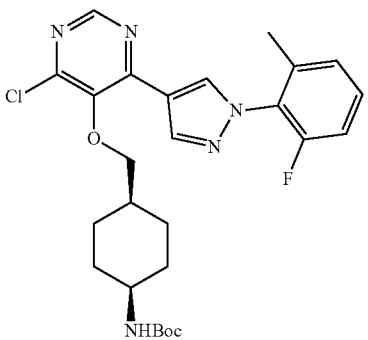 [SMILES: Cc1cccc(F)c1-n1cc(-c2ncnc(Cl)c2OC[C@H]2CC[C@@H](NC(=O)OC(C)(C)C)CC2)cn1]

Using Method 4A, 250 mg of 1-(2-fluoro-6-methylphenyl)-4-(4,4,5,5-tetramethyl-1,3,2-dioxaborolan-2-yl)-1H-pyrazole was converted into tert-butyl ((1s, 4s)-4-(((4-chloro-6-(1-(2-fluoro-6-methylphenyl)-1H-pyrazol-4-yl)pyrimidin-5-yl)oxy)methyl)-cyclohexyl)-carbamate.
Yield (35%): 150 mg.
Appearance: White solid.
LC/MS: Calculated 516.01; Observed m/z [M+H]⁺516.1.
LC/MS purity: 97.87%.

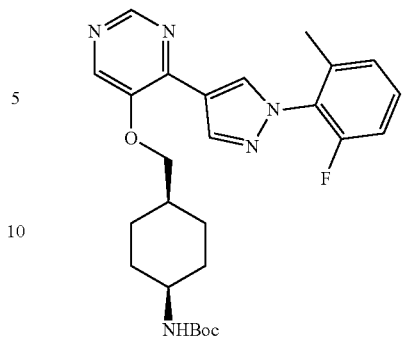

Using Method 5A, 150 mg of tert-butyl ((1s, 4s)-4-(((4-chloro-6-(1-(2-fluoro-6-methylphenyl)-1H-pyrazol-4-yl)pyrimidin-5-yl)oxy)methyl)cyclohexyl)carbamate was converted into tert-butyl ((1s, 4s)-4-(((4-(1-(2-fluoro-6-methylphenyl)-1H-pyrazol-4-yl)-pyrimidin-5-yl)oxy)methyl)cyclohexyl)carbamate.
Yield (72%): 100 mg.
Appearance: White solid.
LC/MS: Calculated 481.57; Observed m/z [M+H]⁺482.2.
LC/MS purity: 99.89%.

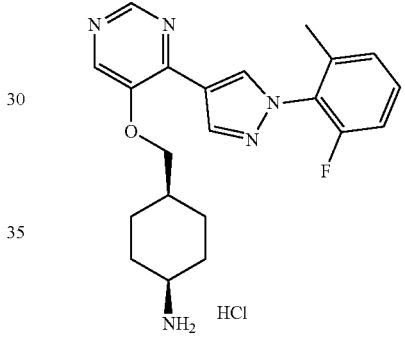

Using Method 6A, 100 mg of tert-butyl ((1s, 4s)-4-(((4-(1-(2-fluoro-6-methylphenyl)-1H-pyrazol-4-yl)pyrimidin-5-yl)oxy)methyl)cyclohexyl)carbamate was converted into (1s, 4s)-4-(((4-(1-(2-fluoro-6-methylphenyl)-1H-pyrazol-4-yl)pyrimidin-5-yl)oxy)methyl)-cyclohexan-1-amine hydrochloride.
Yield (97%): 85 mg.
Appearance: Off white solid.
LC/MS: Calculated 417.91; Observed m/z [M+H]⁺382.2.
HPLC purity: 98.05%.

Example 28

Preparation of Compound I-15

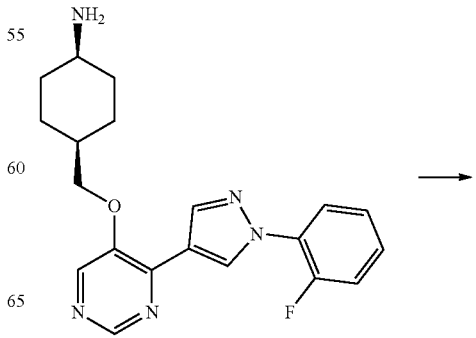

-continued

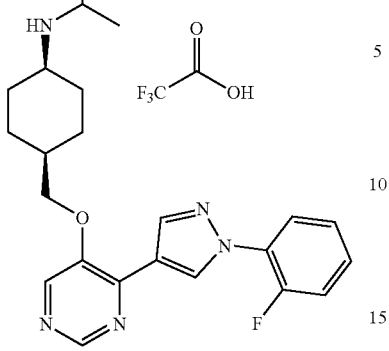

Acetone (0.2 mL) was added to a stirred solution of (s, 4s)-4-(((4-(1-(2-fluorophenyl)-1H-pyrazol-4-yl)pyrimidin-5-yl)oxy)methyl)cyclohexan-1-amine (75 mg, 0.204 mmol, 1 eq) in methanol (2 mL) at ambient temperature. The reaction mixture was concentrated in vacuo. To the residue dissolved in methanol, was added Na(OAc)$_3$BH (216.36 mg, 1.02 mmol, 5 eq) at 0° C. Reaction mixture was stirred at ambient temperature for 4 h. The reaction mass was concentrated in vacuo. The residue thus obtained was diluted with water (20 mL) and extracted with dichloromethane (2×30 mL). The combined organic layer was washed with saturated brine solution, dried over anhydrous sodium sulfate, filtered and concentrated in vacuo. The crude product was purified by prep HPLC afford compound I-15.

Yield (18%): 15 mg.
Appearance: Off white solid.
LC/MS: Calculated 523.53; Observed m/z [M+H]$^+$410.2.
HPLC purity: 96.02%.

Example 29

Synthesis of Compound I-16

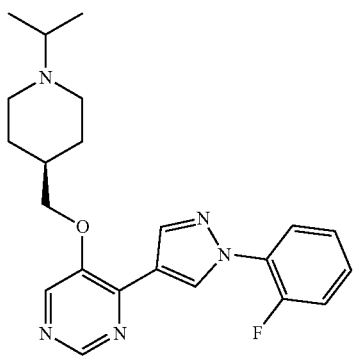

Using the modified Mitsunobu procedure used to synthesize compound I-8, 4-(1-(2-fluorophenyl)-1H-pyrazol-4-yl)pyrimidin-5-ol (100 mg) was converted into 4-(1-(2-fluorophenyl)-1H-pyrazol-4-yl)-5-((1-isopropyl piperidin-4-yl)methoxy)pyrimidine.

Yield (39%): 60 mg.
Appearance: Colorless gum.
LC/MS: Calculated 395.48; Observed m/z [M+H]$^+$ 396.21.
HPLC purity: 98.59%.

Example 30

Synthesis of Compound I-17

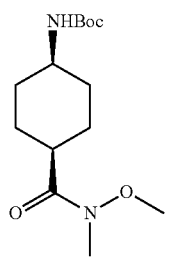 [SMILES: CON(C)C(=O)[C@H]1CC[C@@H](NC(=O)OC(C)(C)C)CC1]

To an ice cold solution of (1s, 4s)-4-((tert-butoxycarbonyl)amino)cyclohexane-1-carboxylic acid (5 g, 20 mmol), N—O dimethyl hydroxylamine. HCl (2.52 g, 26 mmol) and triethylamine (6.2 g, 60 mmol) in dichloromethane (50 mL) was added propylphosphonic anhydride (T3P, 6.7 g, 30 mmol) and the reaction mixture was stirred at room temperature for 16 h. The reaction mixture was diluted with water and the crude product was extracted with dichloromethane. The combined extracts were concentrated and purified by column chromatography to afford the tert-butyl ((1s, 4s)-4-(methoxy(methyl)carbamoyl)cyclohexyl)carbamate as off white solid.

Yield (74%): 4.2 g.
LC/MS: Calculated 286.37; Observed m/z 287 [M+H].

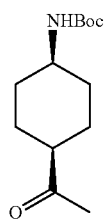 [SMILES: CC(=O)[C@H]1CC[C@@H](NC(=O)OC(C)(C)C)CC1]

MeMgBr (20 mL, 2M in THF, 40 mmol) was added to an ice cold solution of tert-butyl ((1s, 4s)-4-(methoxy(methyl) carbamoyl)cyclohexyl)carbamate (3.0 g, 10.4 mmol) in THE (30 mL) under nitrogen atmosphere and the reaction mixture was stirred at room temperature for 4 h. The reaction mixture was quenched with saturated ammonium chloride and the crude product was extracted with ethyl acetate. The combined extracts were concentrated and purified to afford tert-butyl ((1s, 4s)-4-acetylcyclohexyl)carbamate as off white solid.

Yield (68%): 1.7 g.
LC/MS: Calculated 241.33; Observed m/z 142.1 [M+H]-100.

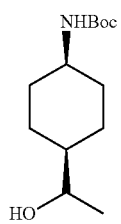

Sodium borohydride (0.057 g, 1.5 mmol) was added to an ice cold solution of tert-butyl ((1s, 4s)-4-acetylcyclohexyl)carbamate (0.25 g, 1.0 mmol) in methanol (5 mL) and the reaction mixture was stirred at room temperature for 3 h. The reaction mixture was concentrated, diluted with water and the crude product was extracted with dichloromethane. The combined extracts were concentrated and purified by column chromatography to afford tert-butyl ((1R, 4s)-4-((S)-1-hydroxyethyl)cyclohexyl)carbamate clear gum.

Yield (60%): 0.15 g.

LC/MS: Calculated 243.35; Observed m/z 142.1 [M+H]-100.

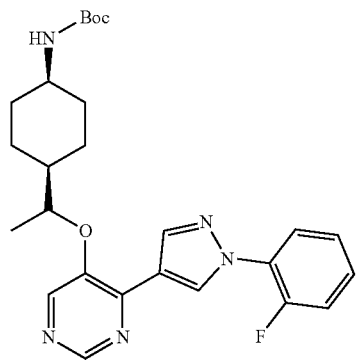 [SMILES: CC(Oc1cncnc1-c1cnn(-c2ccccc2F)c1)[C@H]1CC[C@@H](NC(=O)OC(C)(C)C)CC1]

Using the modified Mitsunobu procedure used for Compound I-8, 4-(1-(2-fluorophenyl)-1H-pyrazol-4-yl)pyrimidin-5-ol (80 mg) was converted into tert-butyl ((1S, 4s)-4-((R)-1-((4-(1-(2-fluorophenyl)-1H-pyrazol-4-yl)pyrimidin-5-yl)oxy)ethyl)cyclohexyl)carbamate.

Yield (39%): 60 mg.

Appearance: Colorless gum.

LC/MS: Calculated 481.57; Observed m/z [M+H]⁺482.2.

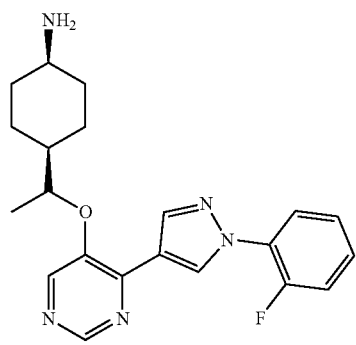 [SMILES: CC(Oc1cncnc1-c1cnn(-c2ccccc2F)c1)[C@H]1CC[C@@H](N)CC1]

Using Method 6A, tert-butyl ((1S, 4s)-4-((R)-1-((4-(1-(2-fluorophenyl)-1H-pyrazol-4-yl)pyrimidin-5-yl)oxy)ethyl)cyclohexyl) carbamate (70 mg) was converted into (1S, 4s)-4-((R)-1-((4-(1-(2-fluorophenyl)-1H-pyrazol-4-yl)pyrimidin-5-yl)oxy)ethyl)-cyclohexan-1-amine.

Yield (95%): 70 mg.

Appearance: Colorless gum.

LC/MS: Calculated 381.46; Observed m/z [M+H]⁺382.3.

HPLC purity: 94.10%.

Example 31

Synthesis of Compound I-18

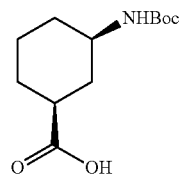 [SMILES: CC(C)(C)OC(=O)N[C@@H]1CCC[C@H](C(=O)O)C1]

Using Method 10A, 2.0 g of (1S,3R)-3-aminocyclohexane-1-carboxylic acid was converted into (1S,3R)-3-((tert-butoxycarbonyl)amino)cyclohexane-1-carboxylic acid.

Yield (75%): 2.5 g.

LC/MS: Calculated 243.30; Observed m/z 144.1 [M+H]-100.

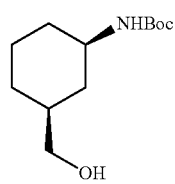 [SMILES: CC(C)(C)OC(=O)N[C@@H]1CCC[C@H](CO)C1]

Using Method 11A, 1.0 g of (1S,3R)-3-((tert-butoxycarbonyl)amino)cyclohexane-1-carboxylic acid was converted into tert-butyl ((1R,3S)-3-(hydroxymethyl)cyclohexyl) carbamate.

Yield (70% yield): 0.6 g

LC/MS: Calculated 229.32; Observed m/z 130.12 [M+H]-100.

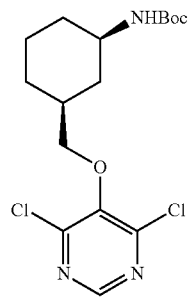 [SMILES: CC(C)(C)OC(=O)N[C@@H]1CCC[C@H](COc2c(Cl)ncnc2Cl)C1]

Using the modified Mitsunobu procedure used for preparation of compound I-8, tert-butyl ((1R,3S)-3-(hydroxymethyl)cyclohexyl)carbamate (400 mg) was converted into tert-butyl ((1R,3S)-3-(((4,6-dichloropyrimidin-5-yl)oxy)methyl)cyclohexyl)carbamate.

Yield (61%): 400 mg.

Appearance: Colorless gum.

LC/MS: Calculated 376.28; Observed m/z [M+H]⁺322.1.

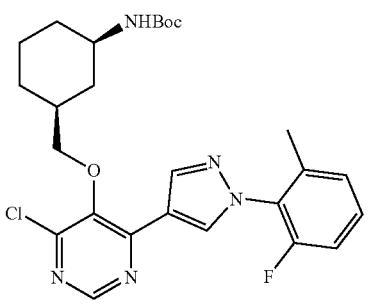 [SMILES: Cc1cccc(F)c1-n1cc(-c2ncnc(Cl)c2OC[C@H]2CCC[C@@H](NC(=O)OC(C)(C)C)C2)cn1]

Using Method 4A tert-butyl ((1R,3S)-3-(((4,6-dichloropyrimidin-5-yl)oxy)methyl)cyclohexyl)carbamate (250 mg) was converted into tert-butyl ((1R,3S)-3-(((4-chloro-6-(1-(2-fluoro-6-methylphenyl)-1H-pyrazol-4-yl)pyrimidin-5-yl)oxy)methyl)cyclohexyl)carbamate.

Yield (40%): 200 mg.

Appearance: Brown solid.

LC/MS: Calculated 516.01; Observed m/z [M+H]$^+$516.5.

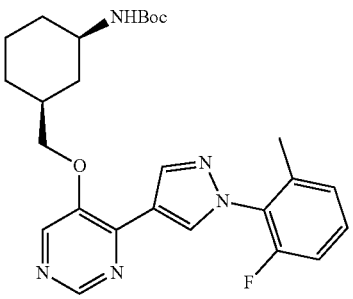 [SMILES: Cc1cccc(F)c1-n1cc(-c2ncncc2OC[C@H]2CCC[C@@H](NC(=O)OC(C)(C)C)C2)cn1]

Using Method 5A, tert-butyl ((1R,3S)-3-(((4-chloro-6-(1-(2-fluoro-6-methylphenyl)-1H-pyrazol-4-yl)pyrimidin-5-yl)oxy)methyl) cyclohexyl) carbamate (200 mg) was converted into tert-butyl ((1R,3S)-3-(((4-(1-(2-fluoro-6-methylphenyl)-1H-pyrazol-4-yl)pyrimidin-5-yl)oxy)-methyl)cyclohexyl)carbamate.

Yield (64%): 120 mg.

Appearance: Colorless gum.

LC/MS: Calculated 481.57; Observed m/z [M+H]$^+$482.2.

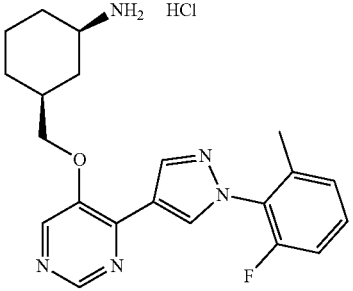 [SMILES: Cl ; Cc1cccc(F)c1-n1cc(-c2ncncc2OC[C@H]2CCC[C@@H](N)C2)cn1]

Using Method 6A, tert-butyl ((1R,3S)-3-(((4-(1-(2-fluoro-6-methylphenyl)-1H-pyrazol-4-yl)pyrimidin-5-yl)oxy)methyl)cyclohexyl)carbamate (200 mg) was converted into (1R,3S)-3-(((4-(1-(2-fluoro-6-methylphenyl)-1H-pyrazol-4-yl)pyrimidin-5-yl)-oxy)-methyl)-cyclohexan-1-amine hydrogen chloride.

Yield (64%): 120 mg.

Appearance: White solid.

LC/MS: Calculated 381.46; Observed m/z [M+H]$^+$382.2.

HPLC purity: 98.27%.

Example 32

Synthesis of Compound I-19

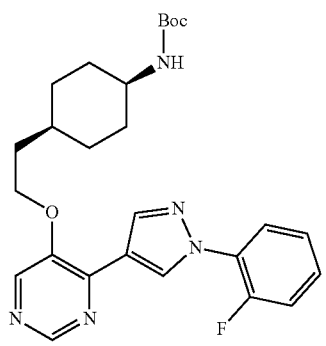 [SMILES: CC(C)(C)OC(=O)N[C@H]1CC[C@@H](CCOc2cncnc2-c2cnn(-c3ccccc3F)c2)CC1]

Using the modified Mitsunobu procedure used for synthesizing Compound I-8, 150 mg of 4-(1-(2-fluorophenyl)-1H-pyrazol-4-yl) pyrimidin-5-ol was converted into tert-butyl ((1s, 4s)-4-(2-((4-(1-(2-fluorophenyl)-1H-pyrazol-4-yl)pyrimidin-5-yl)oxy)ethyl)cyclohexyl)carbamate.

Yield (32%): 90 mg.

Appearance: Brown liquid.

LC/MS: Calculated 481.57; Observed m/z [M+H]$^+$ 482.3.

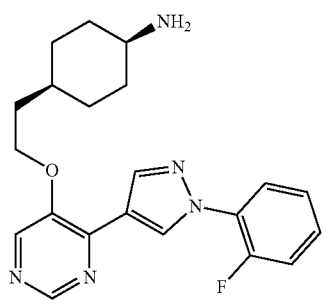 [SMILES: N[C@H]1CC[C@@H](CCOc2cncnc2-c2cnn(-c3ccccc3F)c2)CC1]

Using Method 6A, 90 mg of tert-butyl ((1s, 4s)-4-(2-((4-(1-(2-fluorophenyl)-1H-pyrazol-4-yl)pyrimidin-5-yl)oxy) ethyl)cyclohexyl)carbamate was converted into 1s, 4s)-4-(2-((4-(1-(2-fluoro-phenyl)-1H-pyrazol-4-yl)pyrimidin-5-yl)oxy)ethyl)cyclohexan-1-amine.

Appearance: Colorless gum.

LC/MS: Calculated 381.46; Observed m/z [M+H]$^+$382.2.

HPLC purity: 97.02%.

Example 33

Synthesis of Compound I-20

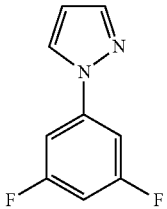

Using Method 1A, 3 g of (3,5-difluorophenyl)hydrazine hydrochloride was converted into 1-(3,5-difluorophenyl)-1H-pyrazole.
Yield (97%): 2.8 g.
Appearance: Pale brown liquid.
LC/MS: Calculated 180.16; Observed m/z [M+H]$^+$181.1.
LC/MS purity: 98.27%.

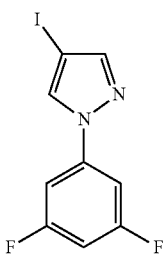

Using Method 2D, 2.8 g of 1-(3,5-difluorophenyl)-1H-pyrazole was converted into 1-(3,5-difluorophenyl)-4-iodo-1H-pyrazole.
Yield (76%): 3.5 g.
Appearance: Pale brown solid.
LC/MS: Calculated 306.05; Observed m/z [M+H]$^+$306.9.
LC/MS purity: 98.32%.

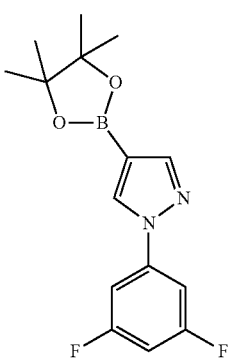 [SMILES: CC1(C)OB(c2cnn(-c3cc(F)cc(F)c3)c2)OC1(C)C]

Using Method 3A, 3 g of 1-(3,5-difluorophenyl)-4-iodo-1H-pyrazole was converted into 1-(3,5-difluorophenyl)-4-(4,4,5,5-tetramethyl-1,3,2-dioxaborolan-2-yl)-1H-pyrazole.
Yield (67%): 2 g.
Appearance: White solid.
LC/MS: Calculated 306.12; Observed m/z [M+H]$^+$307.0.
LC/MS purity: 89.93%.

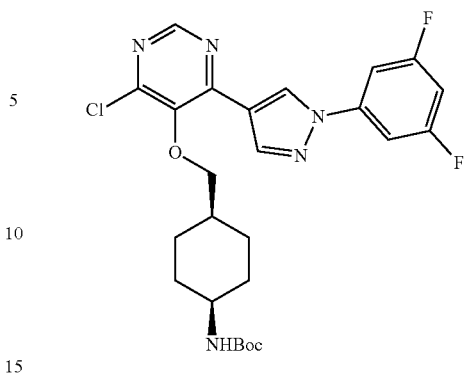

Using Method 4A, 447 mg of 1-(3,5-difluorophenyl)-4-(4,4,5,5-tetramethyl-1,3,2-dioxaborolan-2-yl)-1H-pyrazole was converted into tert-butyl ((1s, 4s)-4-(((4-chloro-6-(1-(3,5-difluorophenyl)-1H-pyrazol-4-yl)pyrimidin-5-yl)oxy)methyl)cyclohexyl)carbamate.
Yield (36%): 250 mg.
Appearance: White solid.
LC/MS: Calculated 519.98; Observed m/z [M+H]$^+$464.1 (Boc fragment mass).
LC/MS purity: 97.43%.

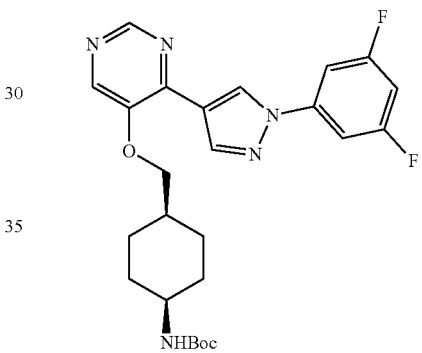

Using Method 5A, 250 mg of tert-butyl ((1s, 4s)-4-(((4-chloro-6-(1-(3,5-difluorophenyl)-1H-pyrazol-4-yl)pyrimidin-5-yl)oxy)methyl)cyclohexyl)carbamate was converted into tert-butyl ((1s, 4s)-4-(((4-(1-(3,5-difluorophenyl)-1H-pyrazol-4-yl)pyrimidin-5-yl)oxy)-methyl)cyclohexyl)carbamate.
Yield (76%): 180 mg.
Appearance: White solid.
LC/MS: Calculated 485.54; Observed m/z [M+H]$^+$486.1.
LC/MS purity: 99.49%.

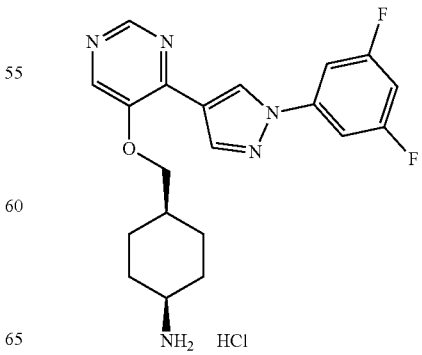

Using Method 6A, 180 mg of tert-butyl (((1s, 4s)-4-(((4-(1-(3,5-difluorophenyl)-1H-pyrazol-4-yl)pyrimidin-5-yl)oxy)-methyl)cyclohexyl)carbamate was converted into (1s, 4s)-4-(((4-(1-(3,5-difluorophenyl)-1H-pyrazol-4-yl)pyrimidin-5-yl)oxy)-methyl)-cyclohexan-1-amine hydrochloride.
Yield (96%): 150 mg.
Appearance: Off white solid.
LC/MS: Calculated 421.88; Observed m/z [M+H]$^+$386.1.
HPLC purity: 97.62%.

Example 34

Preparation of Compound I-21

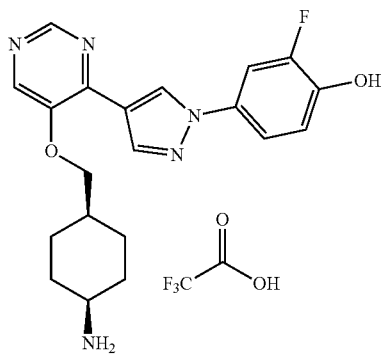 [SMILES: N[C@H]1CC[C@@H](COc2cncnc2-c2cnn(-c3ccc(O)c(F)c3)c2)CC1 ; O=C(O)C(F)(F)F]

BBr$_3$ (1M in dichloromethane) (4 mL, 4.019 mmol, 10 eq) was added to a stirred solution of tert-butyl (((1s, 4s)-4-(((4-(1-(3-fluoro-4-methoxyphenyl)-1H-pyrazol-4-yl)pyrimidin-5-yl)oxy)-methyl)-cyclohexyl)carbamate (200 mg, 0.401 mmol, 1 eq) in dichloromethane (5 mL) at −78° C. The reaction mixture was stirred at ambient temperature for 16 h. The reaction mass was cooled to 0° C., quenched with methanol, and concentrated in vacuo. The crude product was purified by prep HPLC afford compound 4-(4-(5-(((1s, 4s)-4-aminocyclohexyl)-methoxy)pyrimidin-4-yl)-1H-pyrazol-1-yl)-2-fluorophenol trifluoroacetic acid.
Yield (72%): 145 mg.
Appearance: Pale yellow solid.
LC/MS: Calculated 497.45; Observed m/z [M+H]$^+$384.2.
HPLC purity: 99.66%.

Example 35

Preparation of Compound I-22

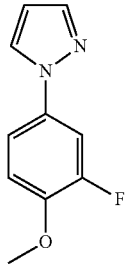

Using Method 1A, 2 g of (3-fluoro-4-methoxyphenyl)hydrazine hydrochloride was converted into 1-(3-fluoro-4-methoxyphenyl)-1H-pyrazole.
Yield (100%): 2 g.
Appearance: Pale brown liquid.
LC/MS: Calculated 192.19; Observed m/z [M+H]$^+$193.1.
LC/MS purity: 84.96%.

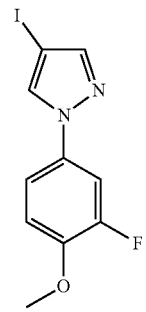

Using Method 2C, 2.0 g of 1-(3-fluoro-4-methoxyphenyl)-1H-pyrazole was converted into 1-(3-fluoro-4-methoxyphenyl)-4-iodo-1H-pyrazole.
Yield (67%): 2.2 g.
Appearance: Pale brown solid.
LC/MS: Calculated 318.09; Observed m/z [M+H]$^+$318.9.
LC/MS purity: 76.57%.

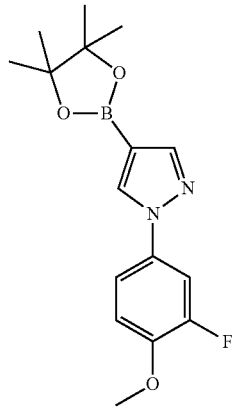 [SMILES: COc1ccc(-n2cc(B3OC(C)(C)C(C)(C)O3)cn2)cc1F]

Using Method 3B, 2.2 g of 1-(3-fluoro-4-methoxyphenyl)-4-iodo-1H-pyrazole was converted into 1-(3-fluoro-4-methoxyphenyl)-4-(4,4,5,5-tetramethyl-1,3,2-dioxaborolan-2-yl)-1H-pyrazole.
Yield (59%): 1.3 g.
Appearance: White solid.
LC/MS: Calculated 318.16; Observed m/z [M+H]$^+$319.2.
LC/MS purity: 49.77%.

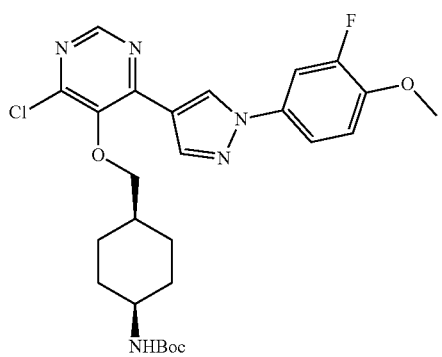 [SMILES: COc1ccc(-n2cc(-c3ncnc(Cl)c3OC[C@H]3CC[C@@H](NC(=O)OC(C)(C)C)CC3)cn2)cc1F]

Using Method 4A, 557 mg of 1-(3-fluoro-4-methoxyphenyl)-4-(4,4,5,5-tetramethyl-1,3,2-dioxaborolan-2-yl)-1H- pyrazole was converted into tert-butyl ((1s, 4s)-4-(((4-chloro-6-(1-(3-fluoro-4-methoxyphenyl)-1H-pyrazol-4-yl)pyrimidin-5-yl)oxy)methyl)cyclohexyl)-carbamate.

Yield (47%): 400 mg.
Appearance: White solid.
LC/MS: Calculated 532.01; Observed m/z [M+H]$^+$532.2.
LC/MS purity: 99.13%.

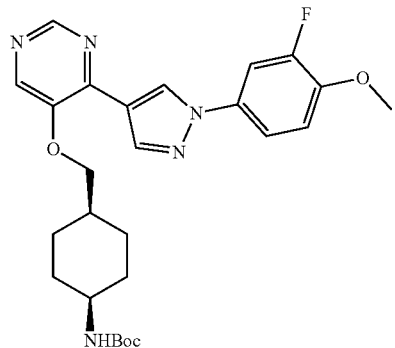 [SMILES: COc1ccc(-n2cc(-c3ncncc3OC[C@H]3CC[C@@H](NC(=O)OC(C)(C)C)CC3)cn2)cc1F]

Using Method 5A, 400 mg of tert-butyl ((1s, 4s)-4-(((4-chloro-6-(1-(3-fluoro-4-methoxyphenyl)-1H-pyrazol-4-yl)pyrimidin-5-yl)oxy)methyl)cyclohexyl)carbamate was converted into tert-butyl ((1s, 4s)-4-(((4-(1-(3-fluoro-4-methoxyphenyl)-1H-pyrazol-4-yl)-pyrimidin-5-yl)oxy)methyl)cyclohexyl)carbamate.

Yield (80%): 300 mg.
Appearance: White solid.
LC/MS: Calculated 497.57; Observed m/z [M+H]$^+$498.1.
LC/MS purity: 98.75%.

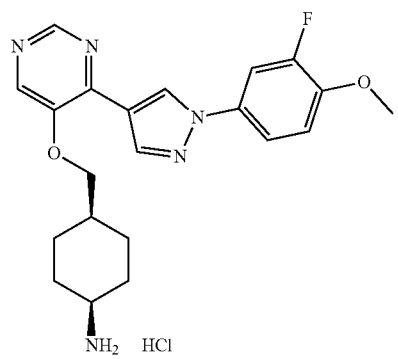 [SMILES: COc1ccc(-n2cc(-c3ncncc3OC[C@H]3CC[C@@H](N)CC3)cn2)cc1F ; Cl]

Using Method 6A, 100 mg of tert-butyl ((1s, 4s)-4-(((4-(1-(3-fluoro-4-methoxyphenyl)-1H-pyrazol-4-yl)pyrimidin-5-yl)oxy)methyl)cyclohexyl)carbamate was converted into (1s, 4s)-4-(((4-(1-(3-fluoro-4-methoxyphenyl)-1H-pyrazol-4-yl)pyrimidin-5-yl)oxy)-methyl)-cyclohexan-1-amine hydrochloride.

Yield (97%): 85 mg.
Appearance: Pale yellow solid.
LC/MS: Calculated 433.91; Observed m/z [M+H]$^+$398.1.
HPLC purity: 99.13%.

Example 36

Synthesis of Compounds I-23 and I-27

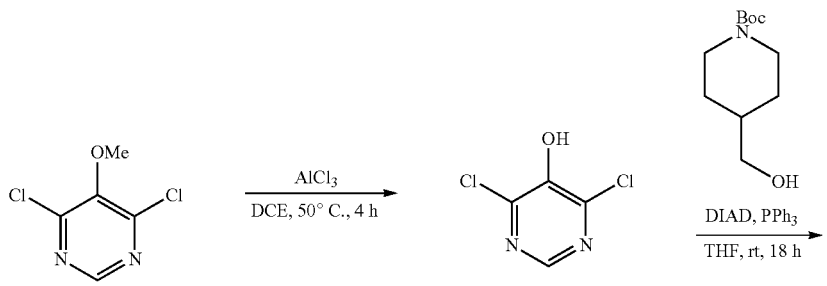

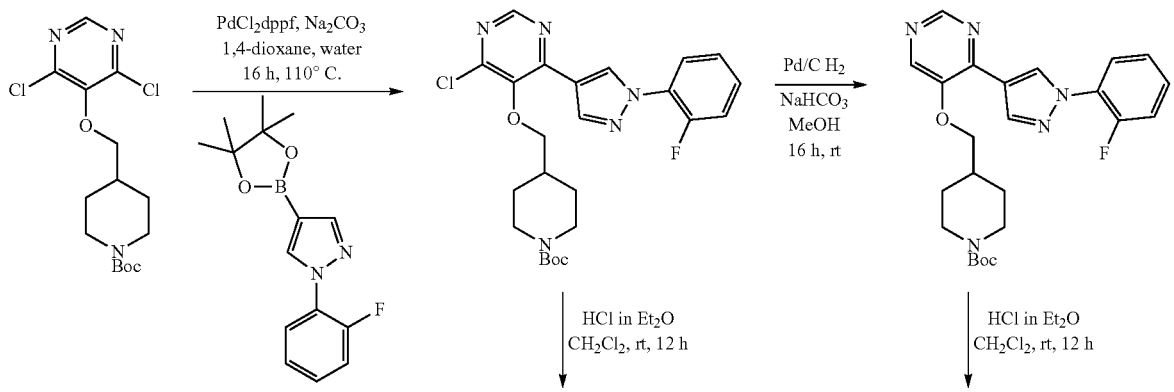

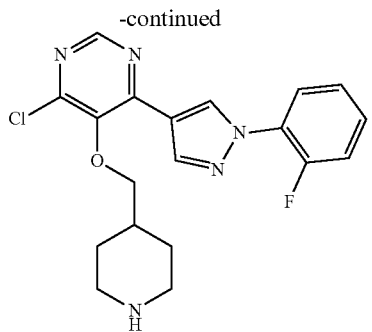

Compound I-27

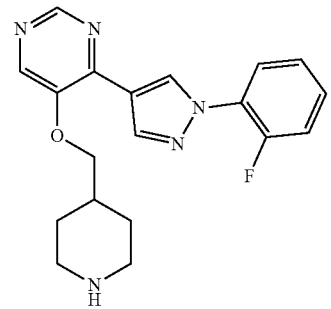

Compound I-23

To a solution of 4,6-dichloro-5-methoxypyrimidine (5.0 g, 28.24 mmol) in DCE (50 mL) at 0° C. was added aluminum trichloride (7.5 g, 56.4 mmol) in two portions. The reaction mixture was stirred at 0° C. for 10 min, then at 50° C. for 4 hr. The mixture was cooled to 0° C. and aqueous HCl (1 M, 20 mL) followed by methanol (20 mL) were added slowly while stirring vigorously. The mixture was poured into water and extracted with diethyl ether. The combined organic layers were washed with brine, dried over magnesium sulfate, filtered and concentrated. The residue was dried in vacuo to afford 4,6-dichloropyrimidin-5-ol as a beige solid.

LC/MS APCI Calculated 163.95; Observed m/z [M+H]$^+$ 165.1.

$^1$H NMR (DMSO-d$_6$): δ (ppm) 11.67 (s, br, 1H), 8.38 (s, 1H).

To a solution of tert-butyl 4-(hydroxymethyl)piperidine-1-carboxylate (1.95 g, 9.06 mmol) in THF (10 mL) was added triphenylphosphine (3.17 g, 12 mmol) and 4,6-dichloropyrimidin-5-ol (1.0 g, 6 mmol). To the mixture was added diisopropylazodicarboxylate (2.4 mL, 12 mmol) at 0° C., and the mixture was stirred at room temperature for 18 hr. The reaction mixture was concentrated in vacuo. The residue was purified by column chromatography on silica gel (hexane:ethyl acetate=40:1 as eluent) to afford the tert-butyl 4-(((4,6-dichloropyrimidin-5-yl)oxy)methyl)piperidine-1-carboxylate as colorless oil (0.6 g, 28% yield).

LC/MS APC: Calculated 361.10; Observed m/z [M+H]$^+$ 362.2.

To 1,4-dioxane (5 mL) was added tert-butyl 4-(((4,6-dichloropyrimidin-5-yl)oxy)methyl)piperidine-1-carboxylate (0.6 g, 1.6 mmol), 1-(2-fluorophenyl)-4-(4,4,5,5-tetramethyl-1,3,2-dioxaborolan-2-yl)-1H-pyrazole (0.47 g, 1.65 mmol), Pd(dppf)Cl$_2$ (0.12 g, 0.16 mmol) and Na$_2$CO$_3$ (0.21 g, 1.98 mmol, in 2 mL water) under N$_2$ atmosphere. The content was heated and kept at 110° C. overnight. The reaction mixture was cooled to room temperature after the completion of the reaction. Dioxane was removed in vacuo and the resultant aqueous solution was extracted with EtOAc. The combined organic phase was washed with water and saturated brine three times, and dried over Na$_2$SO$_4$. After the removal of the solvent under reduced pressure, the residue was purified by flash column chromatography to give pure product tert-butyl 4-(((4-chloro-6-(1-(2-fluorophenyl)-1H-pyrazol-4-yl)pyrimidin-5-yl)oxy)methyl)piperidine-1-carboxylate (0.4 g, 50% yield).

LC/MS APC: Calculated 487.18 Observed m/z [M+H]$^+$ 488.2.

$^1$H-NMR 400 MHz, DMSO-d$_6$: δ 8.88 (s, 1H), 8.75 (s, 1H), 8.46 (s, 1H), 7.94-7.89 (m, 1H), 7.58-7.48 (m, 2H), 7.44-7.40 (m, 1H), 4.79-4.77 (m, 2H), 4.04-3.98 (m, 2H), 3.92-3.90 (m, 2H), 2.81-2.77 (m, 2H), 2.14-2.10 (m, 1H), 1.85-1.81 (m, 2H), 1.07 (s, 9H).

To tert-butyl 4-(((4-chloro-6-(1-(2-fluorophenyl)-1H-pyrazol-4-yl)pyrimidin-5-yl)oxy)methyl)piperidine-1-carboxylate (0.3 g, 0.61 mmol) in methanol was added sodium bicarbonate (0.11 g, 1.23 mmol) and 30 mg of 10% Pd/carbon. The flask was equipped with a hydrogen-filled balloon fitted onto a 3-way stopcock. After several evacuation/hydrogen flush cycles, the reaction mixture was stirred under 1 atm of hydrogen for 16 h. The mixture was filtered through a pad of celite and the pad was rinsed with copious amounts of methanol. The volatiles were removed in vacuo and the crude solid was purified by flash column chromatography to give tert-butyl 4-(((4-(1-(2-fluorophenyl)-1H-pyrazol-4-yl)pyrimidin-5-yl)oxy)methyl)piperidine-1-carboxylate (0.15 g, 56% yield).

LC/MS APC: Calculated 453.22 Observed m/z [M+H]$^+$ 454.3.

$^1$H-NMR 400 MHz, DMSO-d$_6$: δ 8.87 (s, 1H), 8.79 (s, 1H), 8.65 (s, 1H), 8.49 (s, 1H), 7.95-7.92 (m, 1H), 7.57-7.49 (m, 2H), 7.44-7.40 (m, 1H), 4.79-4.60 (m, 2H), 4.21 (d, J=6.40 Hz, 2H), 4.04-4.01 (m, 2H), 2.15-2.12 (m, 1H), 1.84-1.81 (m, 2H), 1.18-1.16 (m, 2H), 1.09 (s, 9H).

To a solution of 4-(((4-chloro-6-(1-(2-fluorophenyl)-1H-pyrazol-4-yl)pyrimidin-5-yl)oxy)methyl)piperidine-1-carboxylate (0.05 g, 0.1 mmol) in dichloromethane was added 4M HCl in diethylether (2.0 mL) and the reaction mixture was stirred at room temperature for 12 h. The reaction mixture was concentrated in vacuo and triturated with diethylether to give 4-chloro-6-(1-(2-fluorophenyl)-1H-pyrazol-4-yl)-5-(piperidin-4-ylmethoxy)pyrimidine (Compound I-27; 18 mg, 46% yield).

LC/MS APC: Calculated 387.13 Observed m/z [M+H]$^+$ 388.0.

$^1$H-NMR 400 MHz, DMSO-d$_6$: δ 8.87 (s, 1H), 8.77 (s, 1H), 8.46 (s, 1H), 7.92 (t, J=8.00 Hz, 1H), 7.58-7.49 (m, 2H), 7.45-7.41 (m, 1H), 4.78-4.75 (m, 2H), 4.02-3.98 (m, 2H), 3.92-3.90 (m, 2H), 2.81-2.77 (m, 2H), 2.14-2.12 (m, 1H), 1.86-1.83 (m, 2H).

To a solution of tert-butyl 4-(((4-(1-(2-fluorophenyl)-1H-pyrazol-4-yl)pyrimidin-5-yl)oxy)methyl)piperidine-1-carboxylate (0.15 g, 0.33 mmol) in dichloromethane was added 4M HCl in diethylether (2.0 mL) and the reaction mixture was stirred at room temperature for 12 h. The reaction mixture was concentrated in vacuo and triturated with diethylether to give 4-(1-(2-fluorophenyl)-1H-pyrazol-4-yl)-5-(piperidin-4-ylmethoxy)pyrimidine (Compound I-23; 40 mg, 37% yield).

LC/MS APC: Calculated 353.17 Observed m/z [M+H]+ 354.2.

$^1$H-NMR 400 MHz, DMSO-d$_6$: δ 8.89 (s, 1H), 8.74 (bs, 1H), 8.61 (s, 1H), 8.44 (s, 1H), 8.36 (s, 1H), 7.90 (t, J=8.00 Hz, 1H), 7.56-7.51 (m, 2H), 7.44 (t, J=8.00 Hz, 1H), 3.29-3.26 (m, 2H), 3.18 (s, 2H), 2.84-2.81 (m, 2H), 1.96-1.93 (m, 1H), 1.93-1.90 (m, 2H), 1.42-1.39 (m, 2H).

Example 37

Synthesis of Compound I-24

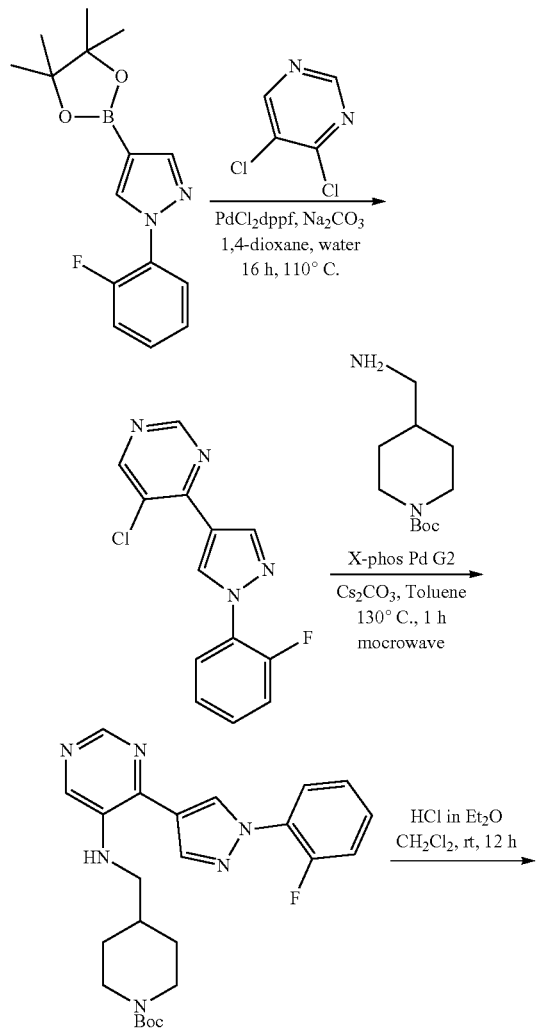

Compound I-24

To 1,4-dioxane (10 mL) was added 4-(4,4,5,5-tetramethyl-1,3,2-dioxaborolan-2-yl)-1H-pyrazole (1.39 g, 4.8 mol), 4,5-dichloropyrimidine (0.718 g, 4.85 mmol), Pd(dppf)Cl$_2$ (0.35 g, 0.47 mmol) and Na$_2$CO$_3$ (0.617 g, 5.82 mmol, in 2 mL water) under N$_2$ atmosphere. The content was heated and kept at 110° C. overnight. The reaction mixture was cooled to room temperature after the completion of the reaction, dioxane was removed under reduced pressure and the resultant aqueous solution was extracted with EtOAc. The combined organic phase was washed with water and saturated brine three times, and dried over Na$_2$SO$_4$. After the removal of the solvent in vacuo, the residue was purified by flash chromatography, which gave the pure product 5-chloro-4-(1-(2-fluorophenyl)-1H-pyrazol-4-yl)pyrimidine (0.2 g, 54% yield).

LC/MS APC: Calculated 180.02 Observed m/z [M+H]+ 181.0.

To toluene (5 mL) was added 5-chloro-4-(1-(2-fluorophenyl)-1H-pyrazol-4-yl)pyrimidine (0.15 g, 0.54 mmol), tert-butyl 4-(aminomethyl)piperidine-1-carboxylate (0.116 g, 1.08 mmol), Xphos second generation catalyst (42 mg, 0.053 mmol) and Cs$_2$CO$_3$ (0.354 g, 5.82 mmol) under N$_2$ atmosphere. The content was heated and kept at 130° C. for 1 h in a microwave reactor. The reaction mixture was cooled to room temperature after the completion of the reaction and toluene was removed in vacuo. The residue was extracted with EtOAc. The combined organic phase was washed with water and saturated brine three times, and dried over Na$_2$SO$_4$. After the removal of the solvent in vacuo, the residue was purified by flash chromatography, which gave the pure product tert-butyl 4-(((4-(1-(2-fluorophenyl)-1H-pyrazol-4-yl)pyrimidin-5-yl)amino)methyl)piperidine-1-carboxylate (40 mg, 18% yield).

LC/MS APC: Calculated 452.23 Observed m/z [M+H]+ 453.0.

To a solution of tert-butyl 4-(((4-(1-(2-fluorophenyl)-1H-pyrazol-4-yl)pyrimidin-5-yl)amino)methyl)piperidine-1-carboxylate 5 (40 mg, 0.088 mmol) in dichloromethane was added 4M HCl in diethylether (2.0 mL) and the reaction mixture was stirred at room temperature for 12 h. The reaction mixture was concentrated in vacuo and purified by preparative HPLC to give 4-(1-(2-fluorophenyl)-1H-pyrazol-4-yl)-N-(piperidin-4-ylmethyl)pyrimidin-5-amine (Compound I-24; 17 mg, 54% yield).

LC/MS APC: Calculated 352.18 Observed m/z [M+H]+ 353.2.

$^1$H-NMR 400 MHz, DMSO-d$_6$: δ 8.89 (s, 1H), 8.86 (bs, 1H), 8.71 (bs, 1), 8.61 (s, 1H), 8.44 (s, 1H), 8.36 (s, 1H), 7.91 (t, J=8.00 Hz, 1H), 7.56-7.51 (m, 2H), 7.44 (t, J=8.00 Hz, 1H), 3.39-3.26 (m, 2H), 3.19-3.17 (m, 2H), 2.84-2.81 (m, 2H), 1.95-1.93 (m, 1H), 1.93-1.90 (m, 2H), 1.42-1.39 (m, 2H).

Example 38

Synthesis of Compound I-25

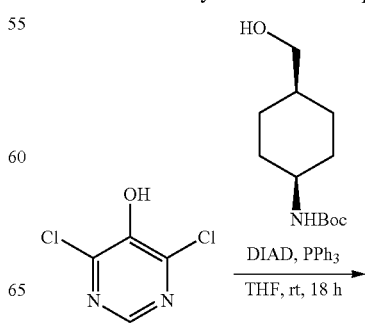

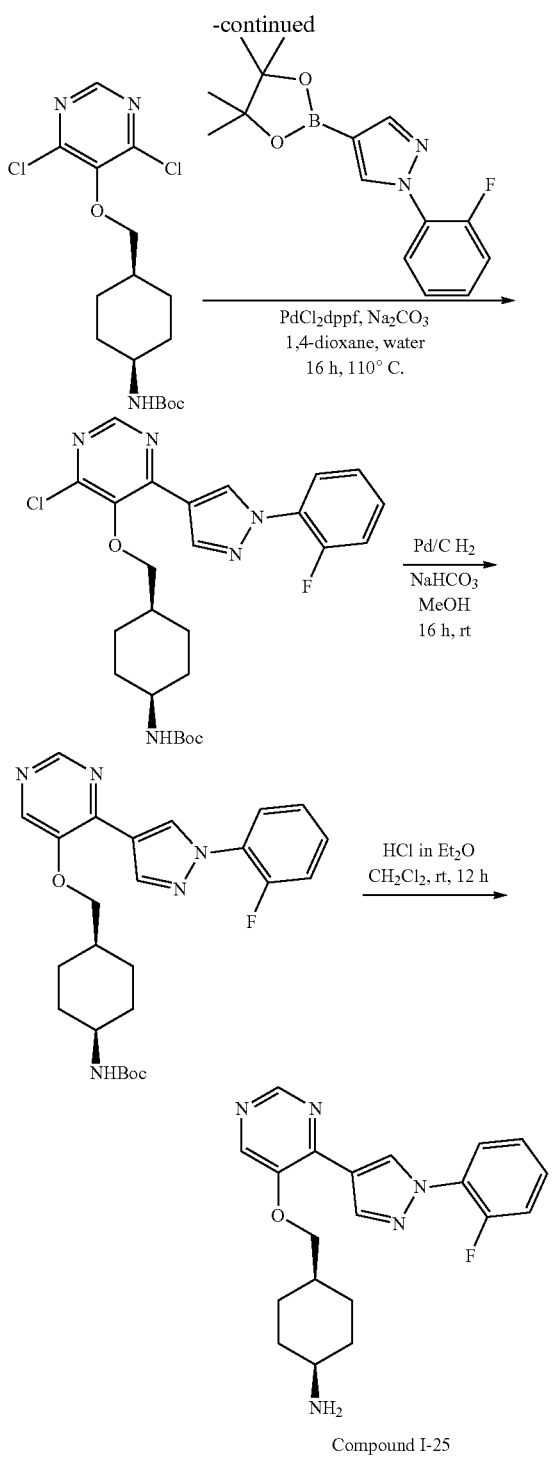

To a solution of tert-butyl (cis-4-(hydroxymethyl)cyclohexyl)carbamate (0.55 g, 2.40 mmol) in THF (15 mL) was added triphenylphosphine (0.96 g, 3.6 mmol) and 4,6-Dichloropyrimidin-5-ol (0.4 g, 2.4 mmol). To the mixture was added diisopropylazodicarboxylate (0.98 g, 4.85 mmol) at 0° C., the mixture was stirred at room temperature for 18 hr. The reaction mixture was concentrated in vacuo and the residue was purified by column chromatography on silica gel (hexane:ethyl acetate=40:1 as eluent) to afford the tert-butyl (cis-4-(((4,6-dichloropyrimidin-5-yl)oxy)methyl)cyclohexyl)carbamate as colorless oil (0.3 g, 38% yield).

LC/MS APC: Calculated 375.11; Observed m/z [M-99 (boc)]$^+$ 276.2.

$^1$H-NMR 400 MHz, DMSO-d$_6$: δ 8.68 (s, 1H), 6.75 (d, J=7.60 Hz, 1H), 3.94 (d, J=6.00 Hz, 2H), 3.14-3.12 (m, 1H), 1.89-1.79 (m, 4H), 1.73-1.71 (m, 1H), 1.38 (s, 9H), 1.19-1.15 (m, 4H).

To 1,4-dioxane (5 mL) were added tert-butyl (cis-4-(((4,6-dichloropyrimidin-5-yl)oxy)methyl)cyclohexyl)carbamate (0.15 g, 0.52 mmol), 1-(2-fluorophenyl)-4-(4,4,5,5-tetramethyl-1,3,2-dioxaborolan-2-yl)-1H-pyrazole (0.19 g, 0.52 mmol), Pd(dppf)Cl$_2$ (38 mg, 0.6 mmol) and Na$_2$CO$_3$ (66 mg, 0.56 mmol, in 2 mL of water) under N$_2$ atmosphere. The content was heated and kept at 110° C. overnight. The reaction mixture was cooled to room temperature after the completion of the reaction, dioxane was removed in vacuo and the resultant aqueous solution was extracted with EtOAc. The combined organic phase was washed with water and saturated brine three times, and dried over Na$_2$SO$_4$. After the removal of the solvent in vacuo, the residue was purified by flash chromatography, which gave the pure product tert-butyl (cis-4-(((4-chloro-6-(1-(2-fluorophenyl)-1H-pyrazol-4-yl)pyrimidin-5-yl)oxy)methyl)cyclohexyl)carbamate (0.1 g, 50% yield).

LC/MS APC: Calculated 501.19 Observed m/z [M+H]$^+$ 502.2.

$^1$H-NMR 400 MHz, DMSO-d$_6$: δ 8.88 (s, 1H), 8.76 (s, 1H), 8.46 (s, 1H), 7.92 (t, J=8.00 Hz, 1H), 7.59-7.48 (m, 2H), 7.44-7.41 (m, 1H), 6.77 (bd, J=8.00 Hz, 1H), 3.86 (d, J=6.40 Hz, 2H), 3.25-3.15 (m, 1H), 1.93-1.82 (m, 5H), 1.38 (s, 9H), 1.26-1.17 (m, 4H).

To tert-butyl (cis-4-(((4-chloro-6-(1-(2-fluorophenyl)-1H-pyrazol-4-yl)pyrimidin-5-yl)oxy)methyl)cyclohexyl)carbamate (0.1 g, 0.19 mmol) in methanol was added sodium bicarbonate (35 mg, 0.38 mmol) and 30 mg of 10% Pd/carbon. The flask was equipped with a hydrogen-filled balloon fitted onto a 3-way stopcock. After several evacuation/hydrogen flush cycles, the reaction mixture was stirred under 1 atm of hydrogen for 16 h. The mixture was filtered through a pad of celite and the pad was rinsed with copious amounts of methanol. The volatiles were removed in vacuo and the crude solid was purified by flash column chromatography to give tert-butyl (cis-4-(((4-(1-(2-fluorophenyl)-1H-pyrazol-4-yl)pyrimidin-5-yl)oxy)methyl)cyclohexyl)carbamate (60 mg, 64% yield).

LC/MS APC: Calculated 467.23 Observed m/z [M+H]$^+$ 468.2.

To a solution of tert-butyl (cis-4-(((4-(1-(2-fluorophenyl)-1H-pyrazol-4-yl)pyrimidin-5-yl)oxy)methyl)cyclohexyl)carbamate (60 mg, 0.13 mmol) in dichloromethane was added 4M HCl in diethylether (2.0 mL) and the reaction mixture was stirred at room temperature for 12 h. The reaction mixture was concentrated in vacuo and triturated with diethylether to give cis-4-(((4-(1-(2-fluorophenyl)-1H-pyrazol-4-yl)pyrimidin-5-yl)oxy)methyl)cyclohexan-1-amine (Compound I-25; 22 mg, 46% yield).

LC/MS APC: Calculated 367.18 Observed m/z [M+H]$^+$ 368.1.

$^1$H-NMR 400 MHz, DMSO-d$_6$: δ 8.87 (d, J=2.80 Hz, 1H), 8.79 (s, 1H), 8.68 (s, 1H), 8.49 (s, 1H), 7.95-7.92 (m, 1H), 7.90 (bs, 2H), 7.55-7.47 (m, 2H), 7.43-7.39 (m, 1H), 4.21 (d, J=7.20 Hz, 2H), 3.27-3.25 (m, 1H), 2.18-2.16 (m, 1H), 1.73-1.71 (m, 8H).

Example 39

Synthesis of Compound I-26

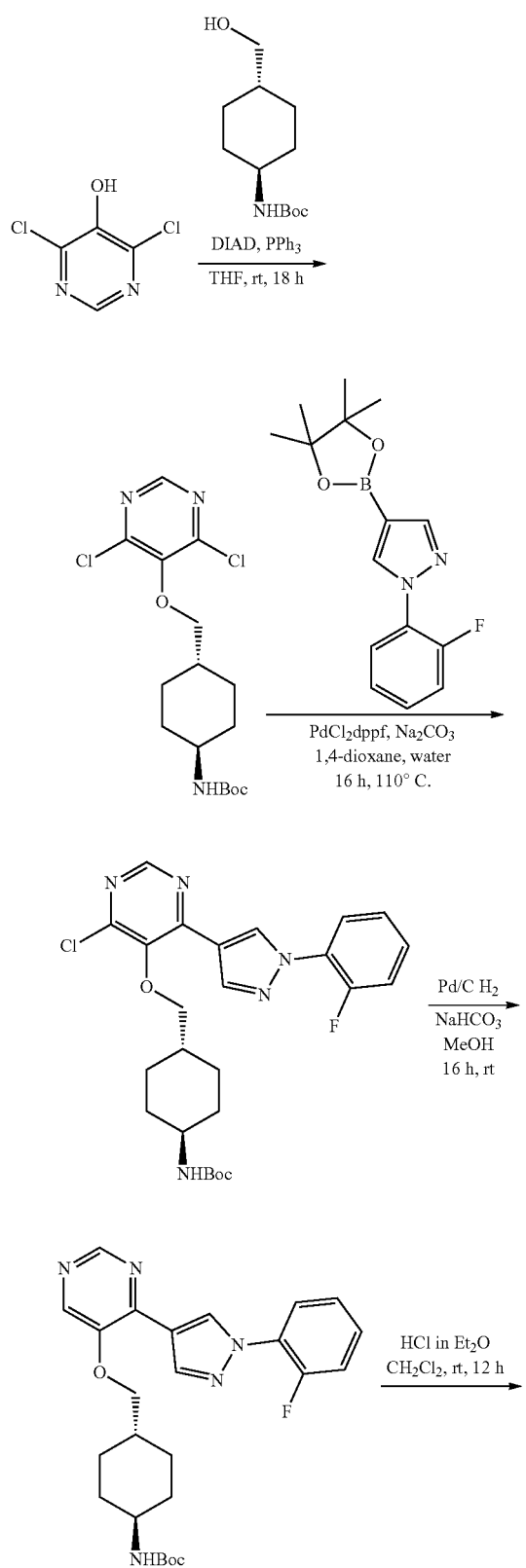

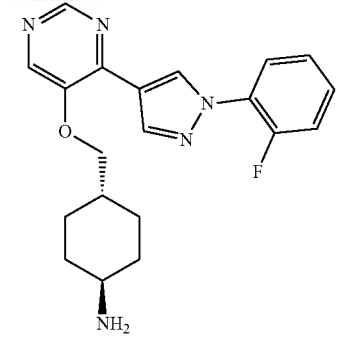

Compound I-26

To a solution of tert-butyl (trans-4-(hydroxymethyl)cyclohexyl)carbamate (0.84 g, 3.65 mmol) in THF (15 mL) was added triphenylphosphine (1.43 g, 5.45 mmol) and 4,6-dichloropyrimidin-5-ol (0.68 g, 3.65 mmol). To the mixture was added diisopropylazodicarboxylate (1.47 g, 7.27 mmol) at 0° C., the mixture was stirred at room temperature for 18 hr. The reaction mixture was concentrated in vacuo and the residue was purified by column chromatography on silica gel (hexane:ethyl acetate=40:1 as eluent) to afford the tert-butyl (trans-4-(((4,6-dichloropyrimidin-5-yl)oxy)methyl)cyclohexyl)carbamate as colorless oil (0.45 g, 33% yield).

LC/MS APC: Calculated 375.11; Observed m/z [M-99 (boc)]$^+$ 276.1.

$^1$H-NMR 400 MHz, DMSO-d$_6$: δ 8.68 (s, 1H), 6.75 (d, J=7.60 Hz, 1H), 3.94 (d, J=6.00 Hz, 2H), 3.16-3.14 (m, 1H), 1.89-1.79 (m, 4H), 1.73-1.71 (m, 1H), 1.38 (s, 9H), 1.19-1.16 (m, 4H).

To 1,4-dioxane (5 mL) was added tert-butyl (trans-4-(((4,6-dichloropyrimidin-5-yl)oxy)methyl)cyclohexyl)carbamate (0.26 g, 0.69 mmol), 1-(2-fluorophenyl)-4-(4,4,5,5-tetramethyl-1,3,2-dioxaborolan-2-yl)-1H-pyrazole (0.2 g, 0.69 mmol), Pd(dppf)Cl$_2$ (50 mg, 0.069 mmol) and Na$_2$CO$_3$ (88 mg, 0.83 mmol, in 2 mL of water) under N$_2$ atmosphere. The content was heated and kept at 110° C. overnight. The reaction mixture was cooled to room temperature after the completion of the reaction, dioxane was removed in vacuo and the resultant aqueous solution was extracted with EtOAc. The combined organic phase was washed with water and saturated brine three times, and dried over Na$_2$SO$_4$. After the removal of the solvent in vacuo, the residue was purified by flash chromatography, which gave the pure product tert-butyl (trans-4-(((4-chloro-6-(1-(2-fluorophenyl)-1H-pyrazol-4-yl)pyrimidin-5-yl)oxy)methyl)cyclohexyl) carbamate (0.15 g, 56% yield).

LC/MS APC: Calculated 501.19 Observed m/z [M+H]$^+$ 502.2.

To tert-butyl (trans-4-(((4-chloro-6-(1-(2-fluorophenyl)-1H-pyrazol-4-yl)pyrimidin-5-yl)oxy)methyl)cyclohexyl) carbamate (200 mg, 0.39 mmol) in methanol was added sodium bicarbonate (71 mg, 0.78 mmol) and 50 mg of 10% Pd/carbon. The flask was equipped with a hydrogen-filled balloon fitted onto a 3-way stopcock. After several evacuation/hydrogen flush cycles, the reaction mixture was stirred under 1 atm of hydrogen for 16 h. The mixture was filtered through a pad of celite and the pad was rinsed with copious amounts of methanol. The volatiles were removed in vacuo and the crude solid was purified by flash column chromatography to give tert-butyl (trans-4-(((4-(1-(2-fluorophenyl)-1H-pyrazol-4-yl)pyrimidin-5-yl)oxy)methyl)cyclohexyl)carbamate (150 mg, 55% yield). The crude reaction mixture was taken to next step without further analysis.

To a solution of tert-butyl (trans-4-(((4-(1-(2-fluorophenyl)-1H-pyrazol-4-yl)pyrimidin-5-yl)oxy)methyl)cyclohexyl)carbamate (150 mg, 0.32 mmol) in dichloromethane was added 4M HCl in diethylether (2.0 mL) and the reaction mixture was stirred at room temperature for 12 h. The reaction mixture was concentrated in vacuo and triturated with diethylether to give trans-4-(((4-(1-(2-fluorophenyl)-1H-pyrazol-4-yl)pyrimidin-5-yl)oxy)methyl)cyclohexan-1-amine (Compound I-26; 80 mg, 72% yield over two steps).

LC/MS APCI Calculated 367.18 Observed m/z [M+H]$^+$ 368.1.

$^1$H-NMR 400 MHz, DMSO-d$_6$: δ 8.89 (s, 1H), 8.80 (s, 1H), 8.65 (s, 1H), 8.51 (s, 1H), 8.30-8.02 (m, 2H), 7.95 (t, J=8.00 Hz, 1H), 7.54-7.49 (m, 2H), 7.45-7.41 (m, 1H), 4.16 (d, J=5.60 Hz, 2H), 3.02-3.00 (m, 1H), 2.05-1.95 (m, 4H), 1.43-1.40 (m, 1H), 1.29-1.20 (m, 4H).

Example 40

Synthesis of Compound I-28

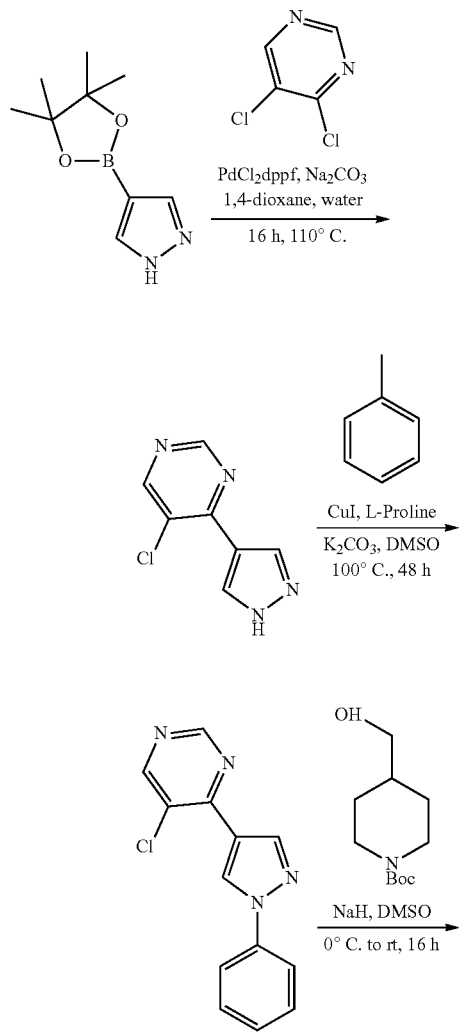

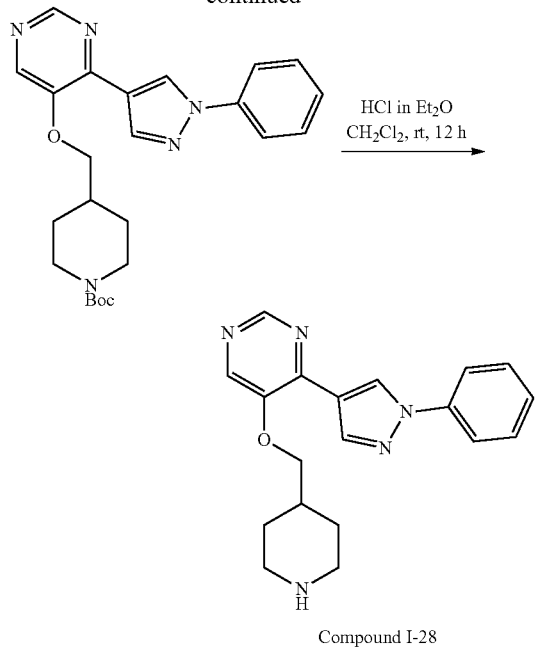

Compound I-28

To 1,4-dioxane (5 mL) was added 4-(4,4,5,5-tetramethyl-1,3,2-dioxaborolan-2-yl)-1H-pyrazole (0.4 g, 0.20 mmol), 4,5-dichloropyrimidine (0.305 g, 0.20 mmol), Pd(dppf)Cl$_2$ (0.15 g, 0.02 mmol) and Na$_2$CO$_3$ (0.26 g, 0.24 mmol) under N$_2$ atmosphere. The content was heated and kept at 110° C. overnight. The reaction mixture was cooled to room temperature after the completion of the reaction, dioxane was removed in vacuo and the resultant aqueous solution was extracted with EtOAc. The combined organic phase was washed with water and saturated brine three times, and dried over Na$_2$SO$_4$. After the removal of the solvent in vacuo, the residue was purified by flash chromatography, which gave the pure product 5-chloro-4-(1H-pyrazol-4-yl)pyrimidine (0.2 g, 54% yield).

LC/MS APCI Observed m/z [M+H]$^+$181.0.

To a solution of 1-iodobenzene (0.35 g, 23.3 mmol) in DMSO (40 mL) was added 5-chloro-4-(1H-pyrazol-4-yl) pyrimidine (0.47 g, 19.4 mmol) followed by CuI (0.037 g, 1.94 mmol), L-proline (0.022 g, 1.94 mmol), and potassium carbonate (0.536 g, 3.88 mmol). The reaction mixture was heated to 100° C. for 48 h. The reaction mixture was cooled to room temperature, filtered through a celite bed and the filtrate was extracted with dichloromethane. The organic layer was concentrated and the residue was purified by flash column chromatography to yield 5-chloro-4-(1-phenyl-1H-pyrazol-4-yl)pyrimidine (0.20 g, 45% yield).

LC/MS APC: Calculated 256.05 Observed m/z [M+H]$^+$ 257.1.

To a solution of tert-butyl 4-(hydroxymethyl)piperidine-1-carboxylate (0.138 g, 0.64 mmol) in DMSO (2 mL) was added sodium hydride (0.185 g, 0.96 mmol) at 0° C. and the reaction stirred at the same temperature for 10 minutes. To the reaction mixture was added 5-chloro-4-(1-phenyl-1H-pyrazol-4-yl)pyrimidine dropwise at 0° C. and the mixture was stirred at room temperature for 16 h. The reaction mixture was quenched with ice and extracted with ethyl acetate. The combined organic layers were washed with saturated aqueous NaCl (15 mL), dried over anhydrous Na$_2$SO$_4$ and concentrated in vacuo. The residue was taken as such to the next step without further purification.

To a solution of tert-butyl 4-(((4-(1-phenyl-1H-pyrazol-4-yl)pyrimidin-5-yl)oxy)methyl)piperidine-1-carboxylate in dichloromethane was added 4M HCl in diethyl ether (2.0 mL) and the reaction mixture was stirred at room temperature for 12 h. The reaction mixture was concentrated in vacuo and purified by preparative HPLC to give 4-(1-phenyl-1H-pyrazol-4-yl)-5-(piperidin-4-ylmethoxy) pyrimidine (Compound I-28; 40 mg, 20% yield over two steps).

LC/MS APC: Calculated 335.17 Observed m/z [M+H]+ 336.1.

$^1$H-NMR 400 MHz, DMSO-d$_6$: δ 9.09 (s, 1H), 8.88 (bs, 1H), 8.80 (d, J=8.00 Hz, 1H), 8.67 (d, J=14.40 Hz, 1H), 8.45 (d, J=6.40 Hz, 1H), 7.96 (d, J=8.00 Hz, 2H), 7.56 (t, J=8.00 Hz, 2H), 7.40 (t, J=7.20 Hz, 1H), 4.25 (d, J=6.00 Hz, 2H), 3.43-3.39 (m, 1H), 3.35-3.31 (m, 1H), 3.00-2.95 (m, 1H), 2.83-2.80 (m, 1H), 2.33-2.29 (m, 1H), 2.00-1.97 (m, 1H), 1.75-1.00 (m, 1H), 1.56-1.53 (m, 1H), 1.36-1.33 (m, 1H).

Example 41

Synthesis of Compounds I-29 and I-30

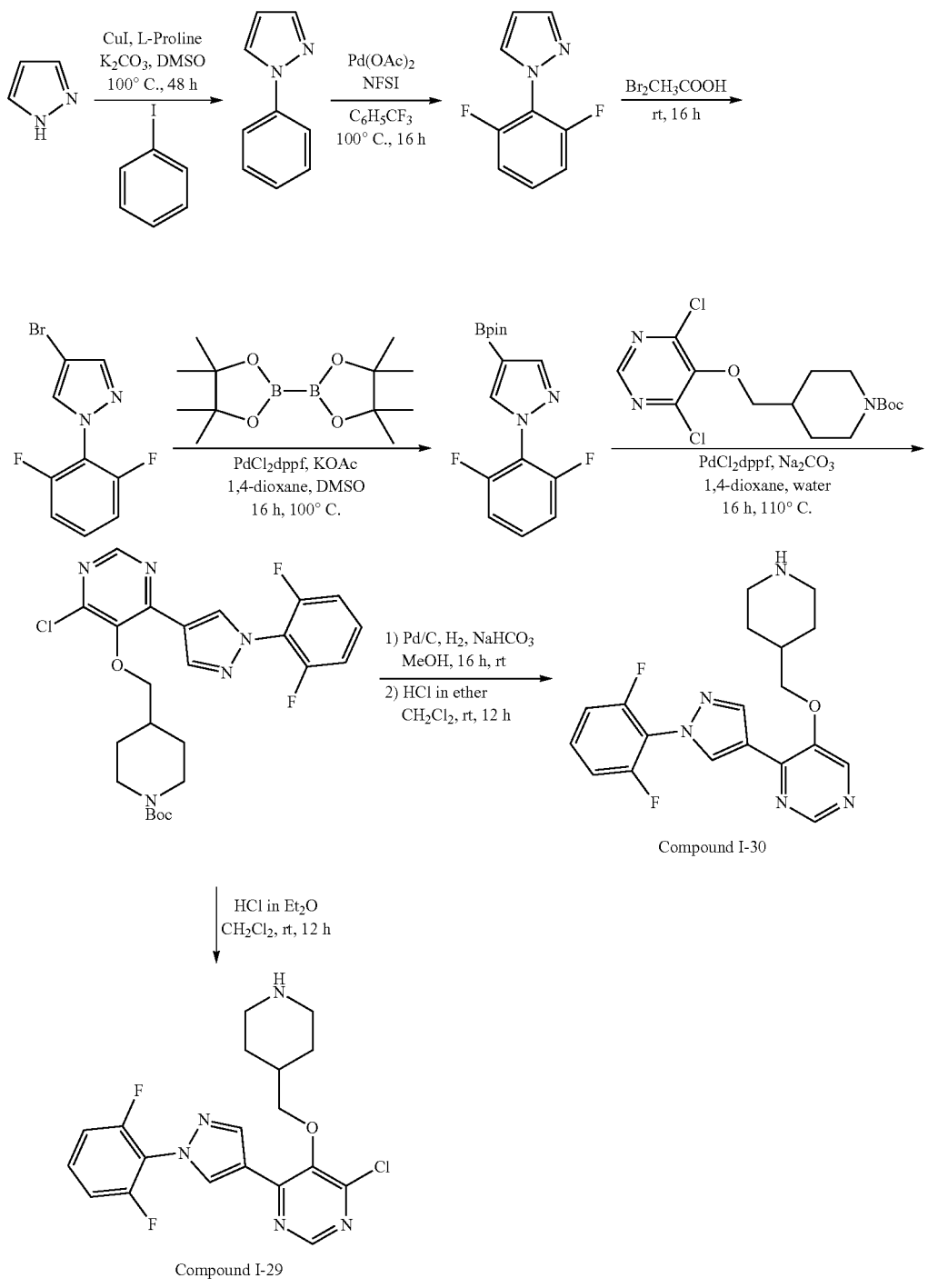

Compound I-30

Compound I-29

To a solution of iodobenzene (7.19 g, 35.2 mmol) in DMSO (40 mL) was added pyrazole (2.0 g, 29.41 mmol) followed by CuI (0.55 g, 2.89 mmol), L-proline (0.337 g, 2.93 mmol), and potassium carbonate (8.1 g, 58.7 mmol). The reaction mixture was heated to 100° C. for 48 h. The reaction mixture was cooled to room temperature, filtered through a celite bed and the filtrate was extracted with dichloromethane. The organic layer was concentrated and the residue was purified by flash column chromatography to yield 1-phenyl-1H-pyrazole (3 g, 71% yield).

LC/MS APC: Calculated 144.07 Observed m/z [M+H]$^+$ 145.1.

$^1$H-NMR 400 MHz, DMSO-d$_6$: δ 8.50 (d, J=2.00 Hz, 1H), 7.85 (d, J=8.40 Hz, 2H), 7.75 (s, 1H), 7.49 (t, J=7.20 Hz, 2H), 7.30 (t, J=7.60 Hz, 1H), 6.54 (t, J=1.60 Hz, 1H).

To a solution of 1-phenyl-1H-pyrazole (0.5 g, 3.47 mmol) in trifluoromethyl benzene was added N-fluorobenzenesulfonimide (NFSI, 3.28 g, 10.4 mmol) followed by palladium acetate (0.077 g, 0.34 mmol) under argon atmosphere and the reaction mixture was heated at 100° C. for 16 h. The reaction mixture was filtered through celite and concentrated under vacuo. The crude residue was purified by flash column chromatography to give 1-(2,6-difluorophenyl)-1H-pyrazole (0.4 g, 64% yield).

LC/MS APC: Calculated 180.05 Observed m/z [M+H]$^+$ 181.1.

$^1$H-NMR 400 MHz, DMSO-d$_6$: δ 8.11 (d, J=2.00 Hz, 1H), 7.82 (d, J=5.20 Hz, 1H), 7.64-7.57 (m, 1H), 7.40-7.34 (m, 2H), 6.57 (t, J=2.00 Hz, 1H).

To solution of 1-(2,6-difluorophenyl)-1H-pyrazole (1.5 g, 8.33 mmol) in acetic acid (5 mL) was added bromine (0.64 g, 4.02 mmol) in acetic acid (5 mL) at 0° C. The reaction mixture was stirred at room temperature for 16 h. The reaction mixture was cooled to room temperature, poured into ice and H$_2$O in a 100 mL beaker and excess saturated, aqueous NaHCO$_3$ was added until all the acetic acid had been quenched. Ethyl acetate (50 mL) was added and the layers were separated. The aqueous layer was extracted with ethyl acetate twice and the combined extracts were dried over Na$_2$SO$_4$ and concentrated in vacuo to give a crude solid which was purified by flash column chromatography (SiO$_2$, 1:1 hexanes-ethyl acetate) to give 4-bromo-1-(2,6-difluorophenyl)-1H-pyrazole (1 g, 46% yield).

LC/MS APC: Calculated 257.96 Observed m/z [M+H]$^+$ 258.9.

$^1$H-NMR 400 MHz, DMSO-d$_6$: δ 8.46 (s, 1H), 7.96 (s, 1H), 7.67-7.61 (m, 1H), 7.43-7.38 (m, 2H).

A mixture of 4-bromo-1-(2,6-difluorophenyl)-1H-pyrazole (1.6 g, 6.1 mmol), potassium acetate (1.21 g, 12.34 mmol), bis(pinacolato)diboron (1.87 g, 7.39 mmol) and Pd(dppf)Cl$_2$ (0.45 g, 0.615 mmol) was suspended in DMSO (4 mL) and 1,4-dioxane (15 mL). The system was purged with N$_2$. The mixture was stirred at 100° C. for 16 h, cooled, and diluted with water (60 mL). The resulting mixture was extracted with dichloromethane (50 mL×3) and the combined organic layers were washed with saturated aqueous NaCl (15 mL), dried over anhydrous Na$_2$SO$_4$ and concentrated in vacuo. The residue was purified by silica gel column chromatography eluted with 20:1 hexanes/ethyl acetate to give 1-(2,6-difluorophenyl)-4-(4,4,5,5-tetramethyl-1,3,2-dioxaborolan-2-yl)-1H-pyrazole (0.6 g, 33% yield).

LC/MS APC: Calculated 306.14 Observed m/z [M+H]$^+$ 307.0.

To 1,4-dioxane (5 mL) was added tert-butyl 4-(((4,6-dichloropyrimidin-5-yl)oxy)methyl)piperidine-1-carboxylate (0.6 g, 1.6 mmol), 1-(2,6-difluorophenyl)-4-(4,4,5,5-tetramethyl-1,3,2-dioxaborolan-2-yl)-1H-pyrazole (0.50 g, 1.65 mmol), Pd(dppf)Cl$_2$ (0.12 g, 0.16 mmol) and Na$_2$CO$_3$ (0.21 g, 1.98 mmol, in 2 mL of water) under N$_2$ atmosphere. The content was heated and kept at 110° C. overnight. The reaction mixture was cooled to room temperature after the completion of the reaction, dioxane was removed in vacuo and the resultant aqueous solution was extracted with EtOAc. The combined organic phase was washed with water and saturated brine three times, and dried over Na$_2$SO$_4$. After the removal of the solvent in vacuo, the residue was purified by flash chromatography, which gave the pure product tert-butyl 4-(((4-chloro-6-(1-(2,6-difluorophenyl)-1H-pyrazol-4-yl)pyrimidin-5-yl)oxy)methyl)piperidine-1-carboxylate (0.4 g, 40% yield).

LC/MS APC: Calculated 505.17 Observed m/z [M+H]$^+$ 506.1.

$^1$H-NMR 400 MHz, DMSO-d$_6$: δ 8.88 (s, 1H), 8.84 (s, 1H), 8.45 (s, 1H), 7.67-7.63 (m, 1H), 7.46-7.38 (m, 2H), 4.80-4.78 (m, 2H), 4.04-4.00 (m, 2H), 3.96-3.92 (m, 2H), 2.32-2.29 (m, 1H), 1.99-1.96 (m, 2H), 1.62-1.57 (m, 2H), 1.17 (s, 9H).

To tert-butyl 4-(((4-chloro-6-(1-(2,6-difluorophenyl)-1H-pyrazol-4-yl)pyrimidin-5-yl)oxy)methyl)piperidine-1-carboxylate (0.2 g, 0.39 mmol) in methanol was added sodium bicarbonate (0.071 g, 0.788 mmol) and 25 mg of 10% Pd/carbon. The flask was equipped with a hydrogen-filled balloon fitted onto a 3-way stopcock. After several evacuation/hydrogen flush cycles, the reaction mixture was stirred under 1 atm of hydrogen for 16 h. The mixture was filtered through a pad of celite and the pad was rinsed with copious amounts of methanol. The volatiles were removed in vacuo to give tert-butyl 4-(((4-(1-(2,6-difluorophenyl)-1H-pyrazol-4-yl)pyrimidin-5-yl)oxy)methyl)piperidine-1-carboxylate (0.10 g, 54% yield) as a crude solid which was taken to next step without further purification.

To a solution of tert-butyl 4-(((4-chloro-6-(1-(2,6-difluorophenyl)-1H-pyrazol-4-yl)pyrimidin-5-yl)oxy)methyl)piperidine-1-carboxylate (0.1 g, 0.19 mmol) in dichloromethane was added 4M HCl in diethylether (2.0 mL) and the reaction mixture was stirred at room temperature for 12 h. The reaction mixture was concentrated in vacuo and purified by preparative HPLC to give 4-chloro-6-(1-(2-fluorophenyl)-1H-pyrazol-4-yl)-5-(piperidin-4-ylmethoxy)pyrimidine (Compound I-29; 12 mg, 15% yield).

LC/MS APC: Calculated 405.12 Observed m/z [M+H]$^+$ 406.0.

$^1$H-NMR 400 MHz, DMSO-d$_6$: δ 8.86 (s, 1H), 8.79 (s, 1H), 8.64 (s, 1H), 8.46 (s, 1H), 7.70-7.65 (m, 1H), 7.46-7.42 (m, 2H), 3.92 (d, J=6.00 Hz, 2H), 2.94-2.91 (m, 2H), 2.51-2.47 (m, 2H), 2.03-1.99 (m, 1H), 1.57-1.48 (m, 2H), 1.24-1.16 (m, 2H).

To a solution of tert-butyl 4-(((4-(1-(2,6-difluorophenyl)-1H-pyrazol-4-yl)pyrimidin-5-yl)oxy)methyl)piperidine-1-carboxylate (0.10 g, 0.19 mmol) in dichloromethane was added 4M HCl in diethylether (2.0 mL) and the reaction mixture was stirred at room temperature for 12 h. The reaction mixture was concentrated in vacuo and purified by preparative HPLC to give 4-(1-(2,6-difluorophenyl)-1H-pyrazol-4-yl)-5-(piperidin-4-ylmethoxy)pyrimidine (Compound I-30; 29.4 mg, 37% yield).

LC/MS APCI Calculated 371.16 Observed m/z [M+H]$^+$ 372.1.

$^1$H-NMR 400 MHz, DMSO-d$_6$: δ 8.81 (s, 1H), 8.80 (s, 1H), 8.68 (s, 1H), 8.57 (bs, 1H), 8.51 (s, 1H), 7.68-7.64 (m, 1H), 7.45-7.41 (m, 2H), 4.23 (d, J=6.00 Hz, 2H), 3.32-3.29 (m, 2H), 2.93-2.88 (m, 2H), 2.28-2.26 (m, 1H), 1.97-1.94 (m, 2H), 1.58-1.52 (m, 2H).

Example 42

Synthesis of Compound I-31

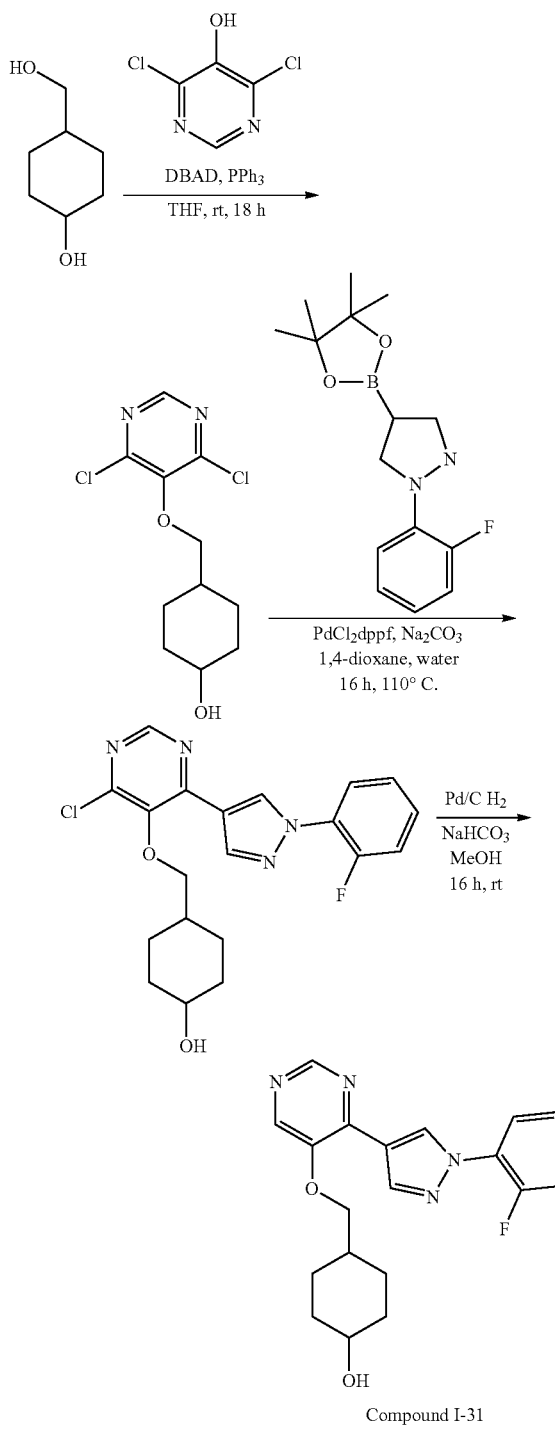

Compound I-31

To a solution of 4-(hydroxymethyl)cyclohexan-1-ol (0.237 g, 1.82 mmol) in THF (15 mL) was added triphenylphosphine (0.718 g, 2.74 mmol) and 4,6-Dichloropyrimidin-5-ol (0.3 g, 1.82 mmol). To the mixture was added di-tert-butyl azodicarboxylate (0.63 g, 2.74 mmol) at 0° C., the mixture was stirred at room temperature for 18 hr. The reaction mixture was concentrated in vacuo. The residue was purified by column chromatography on silica gel (hexane:ethyl acetate=9:1 as eluent) to afford the 4-(((4,6-dichloropyrimidin-5-yl)oxy)methyl)cyclohexan-1-ol (0.15 g, 30% yield).

LC/MS APC: Calculated 276.04; Observed m/z [M+H)]+ 277.0.

To 1,4-dioxane (5 mL) was added 4-(((4,6-dichloropyrimidin-5-yl)oxy)methyl)cyclohexan-1-ol (0.10 g, 0.36 mmol), 1-(2-fluorophenyl)-4-(4,4,5,5-tetramethyl-1,3,2-dioxaborolan-2-yl)-1H-pyrazole (0.104 g, 0.36 mmol), Pd(dppf)Cl₂ (25 mg, 0.034 mmol) and Na₂CO₃ (46 mg, 0.43 mmol in 1 mL water) under N₂ atmosphere. The content was heated and kept at 110° C. overnight. The reaction mixture was cooled to room temperature after the completion of the reaction, dioxane was removed in vacuo and the resultant aqueous solution was extracted with EtOAc. The combined organic phase was washed with water and saturated brine three times, and dried over Na₂SO₄. After the removal of the solvent in vacuo, the residue was purified by flash chromatography, which gave the pure product tert-butyl 4-(((4-chloro-6-(1-(2-fluorophenyl)-1H-pyrazol-4-yl)pyrimidin-5-yl)oxy)methyl)cyclohexan-1-ol (60 mg, 41% yield).

LC/MS APC: Calculated 402.13 Observed m/z [M+H]+ 403.2.

To tert-butyl 4-(((4-chloro-6-(1-(2-fluorophenyl)-1H-pyrazol-4-yl)pyrimidin-5-yl)oxy)methyl)cyclohexan-1-ol (60 mg, 0.15 mmol) in methanol was added sodium bicarbonate (26 mg, 0.28 mmol) and 20 mg of 10% Pd/carbon. The flask was equipped with a hydrogen-filled balloon fitted onto a 3-way stopcock. After several evacuation/hydrogen flush cycles, the reaction mixture was stirred under 1 atm of hydrogen for 16 h. The mixture was filtered through a pad of celite and the pad was rinsed with copious amounts of methanol. The volatiles were removed in vacuo and the crude solid was purified by flash column chromatography to give 4-(((4-(1-(2-fluorophenyl)-1H-pyrazol-4-yl)pyrimidin-5-yl)oxy)methyl)cyclohexan-1-ol (Compound I-31; 15.0 mg, 28% yield).

LC/MS APC: Calculated 368.16 Observed m/z [M+H]+ 369.0.

¹H-NMR 400 MHz, MeOD: δ 8.92-8.89 (m, 1H), 8.73 (d, J=8.80 Hz, 1H), 8.53-7.98 (m, 2H), 7.98-7.91 (m, 1H), 7.48-7.37 (m, 3H), 4.64-4.62 (m, 1H), 4.15 (d, J=14.00 Hz, 2H), 3.58-3.56 (m, 1H), 2.36-2.34 (m, 1H), 2.08-2.05 (m, 2H), 1.68-1.65 (m, 2H), 1.40-1.37 (m, 4H).

Example 43

Synthesis of Compound I-32

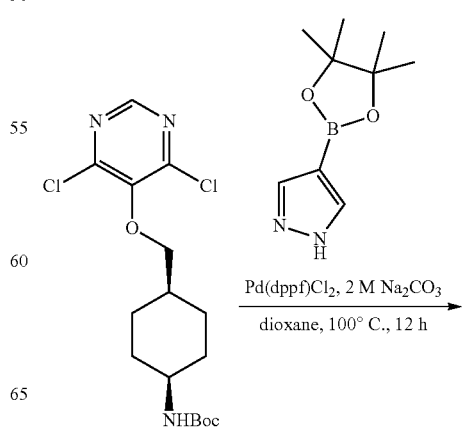

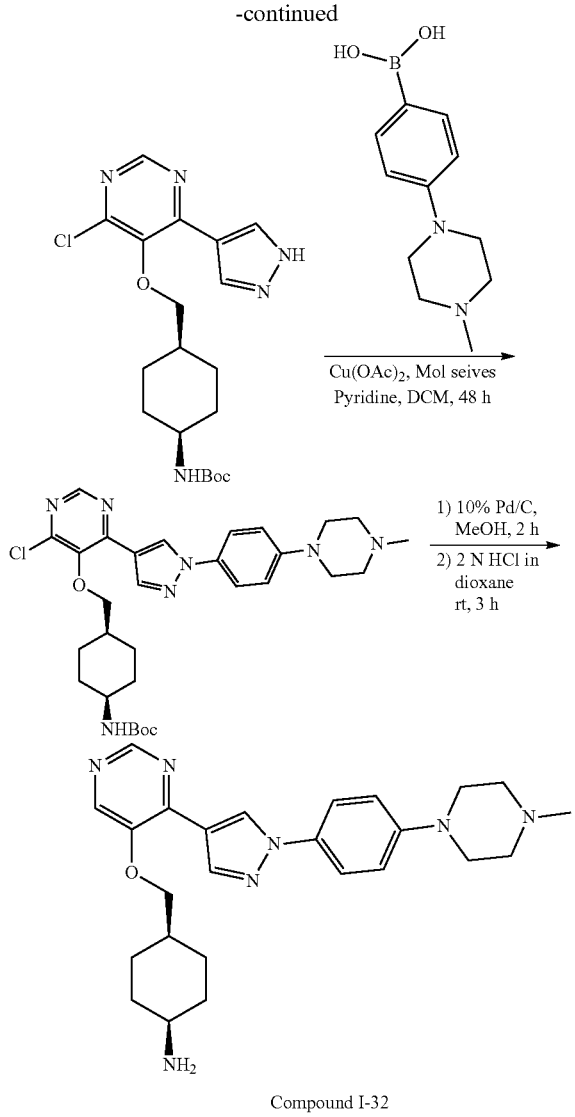

Compound I-32

To a solution of tert-butyl ((1s, 4s)-4-(((4,6-dichloropyrimidin-5-yl)oxy)methyl)cyclohexyl)carbamate (1 g, 2.68 mmol) in 1,4-dioxane (30 mL) was added 4-(4,4,5,5-tetramethyl-1,3,2-dioxaborolan-2-yl)-1H-pyrazole (0.51 g, 2.68 mmol) and aqueous 2 M Na₂CO₃ solution (2.68 mL, 2 eq). The resulting reaction mixture was purged with nitrogen for 20 minutes and then Pd(dppf)Cl₂ (195 mg, 0.268 mmol) was added. The reaction mixture was heated to 100° C. for 12 h in sealed tube. The reaction mixture was cooled, diluted with water, and extracted with ethyl acetate. The combined organic phase was washed with water and brine solution, and dried over Na₂SO₄. After the removal of solvent in vacuo, the crude compound was purified by silica gel column chromatography to obtain tert-butyl ((1s, 4s)-4-(((4-chloro-6-(1H-pyrazol-4-yl)pyrimidin-5-yl)oxy)methyl)cyclohexyl)carbamate as an off brown solid (300 mg, 27.6%).

LC/MS: Calculated 407.17 Observed m/z [M−H]⁺ 406.2.

To a solution of tert-butyl ((1s, 4s)-4-(((4-chloro-6-(1H-pyrazol-4-yl)pyrimidin-5-yl)oxy)methyl)cyclohexyl)carbamate (250 mg, 0.61 mmol) and (4-(4-methylpiperazin-1-yl)phenyl)boronic acid (270 mg, 1.22 mmol) in dichloromethane (20 mL) was added Cu(OAc)₂ (445 mg, 2.45 mmol), molecular sieves powder (400 mg) and pyridine (145 mg, 1.83 mmol). The reaction mixture was stirred at room temperature for 48 h. The reaction mixture was filtered through celite bed and concentrated in vacuo. The crude compound was purified by prep. HPLC to obtain tert-butyl ((1s, 4s)-4-(((4-chloro-6-(1-(4-(4-methylpiperazin-1-yl)phenyl)-1H-pyrazol-4-yl)pyrimidin-5-yl)oxy)methyl)cyclohexyl)carba-mate (110 mg, 30.8%).

LC/MS: Calculated 581.29 Observed m/z [M+H]⁺582.3.

To a solution tert-butyl ((1s, 4s)-4-(((4-chloro-6-(1-(4-(4-methylpiperazin-1-yl)phenyl)-1H-pyrazol-4-yl)pyrimidin-5-yl)oxy)methyl)cyclohexyl)carba-mate (110 mg, 0.19 mmol) in methanol (10 mL) was added triethylamine (76 mg, 0.76 mmol), followed by 10% Pd/carbon (220 mg) and stirred under hydrogen atmosphere for 2 h. The reaction mixture was concentrated in vacuo and was purified by silica gel column chromatography to obtain tert-butyl ((1s, 4s)-4-(((4-(1-(4-(4-methylpiperazin-1-yl)phenyl)-1H-pyrazol-4-yl)pyrimidin-5-yl)oxy)methyl)cyclohexyl)carbamate (60 mg, 58%).

LC/MS: Calculated 547.33 Observed m/z [M+H]⁺548.3.

To a solution of tert-butyl ((1s, 4s)-4-(((4-(1-(4-(4-methylpiperazin-1-yl)phenyl)-1H-pyrazol-4-yl)pyrimidin-5-yl)oxy)methyl)cyclohexyl)carbamate (60 mg, 0.11 mmol) in 3 mL of dioxane was added 4 M HCl in dioxane (3.0 mL) and the reaction mixture was stirred at room temperature for 3 h. The reaction mixture was concentrated in vacuo and triturated with diethyl ether to give (s, 4s)-4-(((4-(1-(4-(4-methylpiperazin-1-yl)phenyl)-1H-pyrazol-4-yl)pyrimidin-5-yl)oxy)methyl)cyclohexan-1-amine hydrochloride salt as yellow solid (Compound I-32; 50 mg, 94.5%).

LC/MS: Calculated 447.27 Observed m/z [M+H]⁺448.2.

HPLC (purity): 97.6%.

¹H-NMR (400 MHz, DMSO-d₆): δ 10.81 (brs, 1H), 8.95 (s, 1H), 8.78 (s, 1H), 8.67 (s, 1H), 8.38 (s, 1H), 8.02 (brs, 3H), 7.79 (d, J=9.2 Hz, 2H), 7.16 (d, J=9.2 Hz, 2H), 4.22 (d, J=7.2 Hz, 2H), 3.90 (d, J=9.2 Hz, 2H), 3.38 (m, 1H), 3.25-3.17 (m, 4H), 2.83 & 2.81 (s, 3H), 2.32-2.20 (m, 1H), 1.73-1.70 (m, 8H).

Example 44

Synthesis of Compound I-32

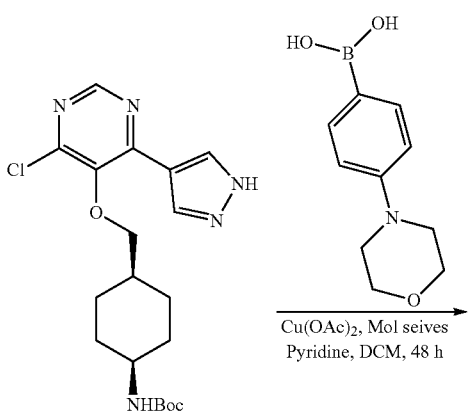

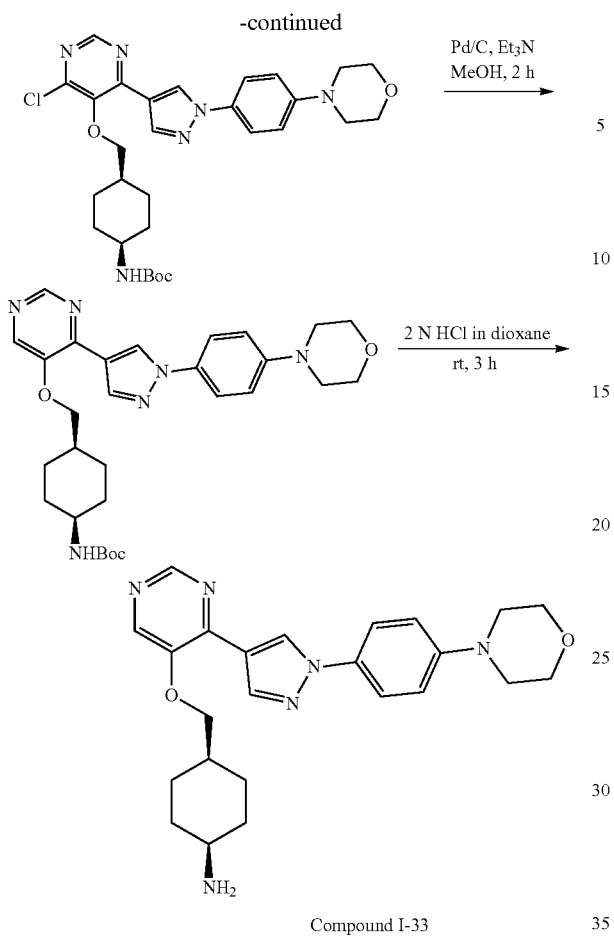

Compound I-33

To a solution of tert-butyl ((1s, 4s)-4-(((4-chloro-6-(1H-pyrazol-4-yl)pyrimidin-5-yl)oxy)methyl)cyclohexyl)carbamate (250 mg, 0.61 mmol) and (4-morpholinophenyl) boronic acid (253 mg, 1.22 mmol) in dichloromethane (20 mL) was added Cu(OAc)$_2$ (445 mg, 2.45 mmol), molecular sieves powder (400 mg) and pyridine (145 mg, 1.83 mmol). The reaction mixture was stirred at room temperature for 48 h. The reaction mixture was filtered through celite bed and concentrated in vacuo. The crude compound was purified by prep. HPLC to obtain tert-butyl ((1s, 4s)-4-(((4-chloro-6-(1-(4-morpholinophenyl)-1H-pyrazol-4-yl)pyrimidin-5-yl)oxy)methyl)cyclohexyl)carbamate (130 mg, 37%).

LC/MS: Calculated 568.26 Observed m/z [M+H]$^+$569.3.

To a solution tert-butyl ((1s, 4s)-4-(((4-chloro-6-(1-(4-morpholinophenyl)-1H-pyrazol-4-yl)pyrimidin-5-yl)oxy)methyl)cyclohexyl)carbamate (130 mg, 0.23 mmol) in methanol (10 mL) was added triethylamine (92 mg, 0.91 mmol), followed by 10% Pd/carbon (260 mg) and the mixture was stirred under hydrogen atmosphere for 2 h. The reaction mixture was concentrated in vacuo and purified by silica gel column chromatography to obtain tert-butyl ((1s, 4s)-4-(((4-(1-(4-morpholinophenyl)-1H-pyrazol-4-yl)pyrimidin-5-yl)oxy)methyl)cyclohexyl)carbamate (55 mg, 45%).

LC/MS: Calculated 534.3 Observed m/z [M+H]$^+$535.2.

To a solution of tert-butyl ((1s, 4s)-4-(((4-(1-(4-morpholinophenyl)-1H-pyrazol-4-yl)pyrimidin-5-yl)oxy)methyl)cyclohexyl)carbamate (55 mg, 0.10 mmol) in 3 mL of dioxane was added 4 M HCl in dioxane (3.0 mL) and the reaction mixture was stirred at room temperature for 3 h. The reaction mixture was concentrated in vacuo and triturated with diethyl ether to give (1s, 4s)-4-(((4-(1-(4-morpholinophenyl)-1H-pyrazol-4-yl)pyrimidin-5-yl)oxy)methyl)cyclohexan-1-amine hydrochloride salt as yellow solid (Compound I-33, 32 mg, 66%).

LC/MS: Calculated 434.24 Observed m/z [M+H]$^+$435.2.

HPLC (purity): 93.66%

$^1$H-NMR (400 MHz, DMSO-d$_6$): δ 8.94 (s, 1H), 8.79 (s, 1H), 8.68 (s, 1H), 8.38 (s, 1H), 7.97 (brs, 3H), 7.76 (d, J=9.2 Hz, 2H), 7.11 (d, J=9.2 Hz, 2H), 4.22 (d, J=7.2 Hz, 2H), 3.78 (t, J=4.8 Hz, 4H), 3.26 (m, 1H), 3.19 (t, J=4.8 Hz, 4H), 2.23 (m, 1H), 1.73-1.70 (m, 8H).

Example 45

Synthesis of Compound I-34

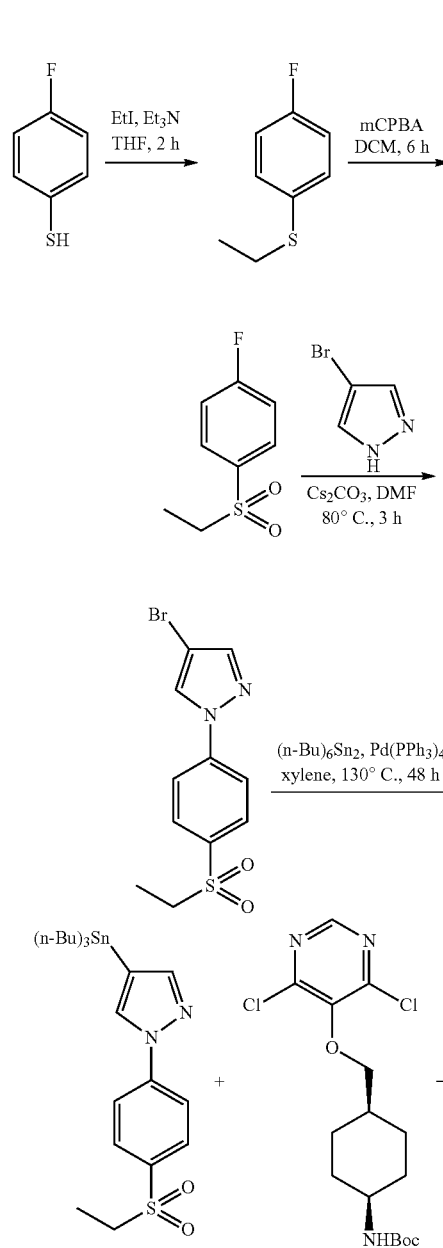

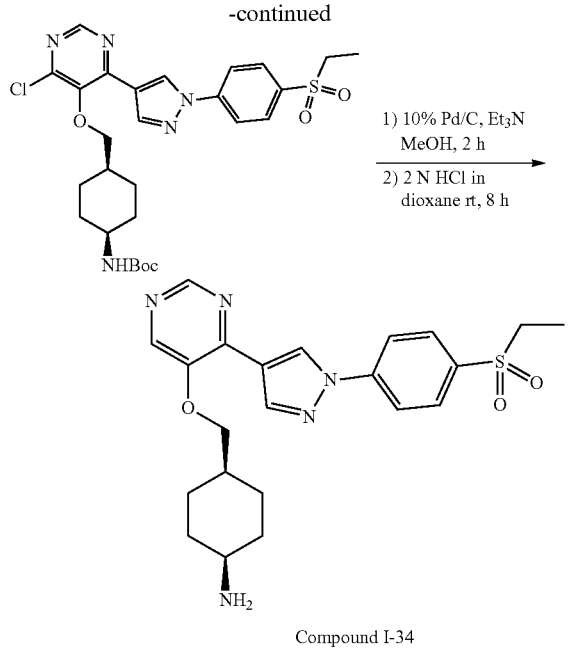

Compound I-34

To a solution of 4-fluorobenzenethiol (5 g, 39 mmol) and iodoethane (3.78 mL, 46.8 mmol) in tetrahydrofuran (50 mL) was added triethylamine (5.44 mL, 39 mmol). The resulting mixture was stirred at ambient temperature for 2 h and then filtered. The filtrate was concentrated, triturated with pentane, and dried in vacuoin vacuo to afford ethyl(4-fluorophenyl)sulfane (2.8 g, 46%). The reaction mixture was used for the next step without further analysis.

To a solution of ethyl(4-fluorophenyl)sulfane (2.5 g, 16 mmol) in dichloromethane (50 mL) was treated with 3-chloroperoxybenzoic acid (8.65 g, 35.2 mmol). The resulting mixture was stirred at ambient temperature for 6 h and then filtered. The filtrate was washed with saturated aqueous sodium bicarbonate solution, dried over anhydrous sodium sulfate, filtered, and concentrated. The residue was purified by silica gel column chromatography to obtain 1-(ethylsulfonyl)-4-fluorobenzene (2.2 g, 73%).

$^1$H-NMR (400 MHz, CDCl$_3$): δ 7.97-7.93 (m, 2H), 7.30-7.25 (m, 2H), 3.14 (q, J=10.0 Hz, 2H), 1.28 (t, J=10.0 Hz, 3H).

To a solution of 1-(ethylsulfonyl)-4-fluorobenzene (2.2 g, 11.7 mmol) and 4-bromo-1H-pyrazole (1.7 g, 11.7 mmol) in DMF (20 mL) was added Cs$_2$CO$_3$ (11.4 g, 35.1 mmol) and the reaction heated at 80° C. for 3 h. The reaction mixture was cooled, treated with water and extracted with ethyl acetate (2×50 mL). The combined organic layers were washed with brine solution, dried over anhydrous sodium sulfate, filtered, and concentrated. The residue was purified by silica gel column chromatography to obtain 4-bromo-1-(4-(ethylsulfonyl)phenyl)-1H-pyrazole (1.4 g, 38%).

LC/MS: Calculated 315.97 Observed m/z [M+H]$^+$317.0.

To a solution of 4-bromo-1-(4-(ethylsulfonyl)phenyl)-1H-pyrazole (1.2 g, 3.8 mmol) and (n-Bu)$_6$Sn$_2$ (6.6 g, 11.4 mmol) in xylene (10 mL) was added Pd(PPh$_3$)$_4$ (439 mg, 0.38 mmol) and heated at 130° C. for 48 h. The reaction mixture was filtered, evaporated and purified by neutral alumina column to furnish 1-(4-(ethylsulfonyl)phenyl)-4-(tributylstannyl)-1H-pyrazole (250 mg, 12.5%) that was used for the next step directly.

To a degassed solution of tert-butyl ((1s, 4s)-4-(((4,6-dichloropyrimidin-5-yl)oxy)methyl)cyclohexyl)carbamate (160 mg, 0.43 mmol) and 1-(4-(ethylsulfonyl)phenyl)-4-(tributylstannyl)-1H-pyrazole (247 mg, 0.47 mmol) in dioxane (10 mL) was added PdCl$_2$(PPh$_3$)$_2$ (30 mg, 0.043 mmol) and the reaction mixture was heated at 110° C. for 16 h. The reaction mixture was filtered through celite bed and concentrated in vacuo. The crude compound was purified by silica gel column chromatography to obtain tert-butyl ((1s, 4s)-4-(((4-chloro-6-(1-(4-(ethylsulfonyl)phenyl)-1H-pyrazol-4-yl)pyrimidin-5-yl)oxy)methyl)cyclohexyl)carbamate 7 (120 mg, 49%).

LC/MS: Calculated 575.20 Observed m/z [M+H]$^+$476.0 (mass corresponding to a loss of BOC group)

To a solution of tert-butyl ((1s, 4s)-4-(((4-chloro-6-(1-(4-(ethylsulfonyl)phenyl)-1H-pyrazol-4-yl)pyrimidin-5-yl)oxy)methyl)cyclohexyl)carbamate 7 (120 mg, 0.21 mmol) in methanol (10 mL) was added triethylamine (84 mg, 0.83 mmol), followed by 10% Pd/carbon (240 mg) and the mixture was stirred under hydrogen atmosphere for 2 h. The reaction mixture was concentrated in vacuo and was purified by silica gel column chromatography to obtain tert-butyl ((1s, 4s)-4-(((4-(1-(4-(ethylsulfonyl)phenyl)-1H-pyrazol-4-yl)pyrimidin-5-yl)oxy)methyl)cyclo-hexyl)carbamate (32 mg, 28%).

LC/MS: Calculated 541.24 Observed m/z [M+H]$^+$442.2 (mass corresponding to a loss of BOC group).

To a solution of tert-butyl ((1s, 4s)-4-(((4-(1-(4-(ethylsulfonyl)phenyl)-1H-pyrazol-4-yl)pyrimidin-5-yl)oxy)methyl)cyclo-hexyl)carbamate (32 mg, 0.06 mmol) in 2 mL of dioxane was added 4 M HCl in dioxane (2.0 mL) and the reaction mixture was stirred at room temperature for 8 h. The reaction mixture was concentrated in vacuum and triturated with diethylether to give (1s, 4s)-4-(((4-(1-(4-(ethylsulfonyl)phenyl)-1H-pyrazol-4-yl)pyrimidin-5-yl)oxy)methyl) cyclo-hexan-1-amine hydrochloride salt as off white solid (Compound I-34; 20 mg, 71%).

LC/MS: Calculated 441.18 Observed m/z [M+H]$^+$442.1. HPLC (purity): 95.19%.

$^1$H-NMR (400 MHz, DMSO-d$_6$): δ 9.24 (s, 1H), 8.83 (s, 1H), 8.75 (s, 1H), 8.51 (s, 1H), 8.23 (d, J=8.8 Hz, 2H), 8.04 (d, J=8.8 Hz, 2H), 7.91 (brs, 3H), 4.24 (d, J=7.2 Hz, 2H), 3.36 (q, 7.2 Hz, 2H), 3.25 (m, 1H), 2.24 (m, 1H), 1.73-1.70 (m, 8H), 1.13 (t, J=7.2 Hz, 3H).

Example 46

Synthesis of Compound I-35

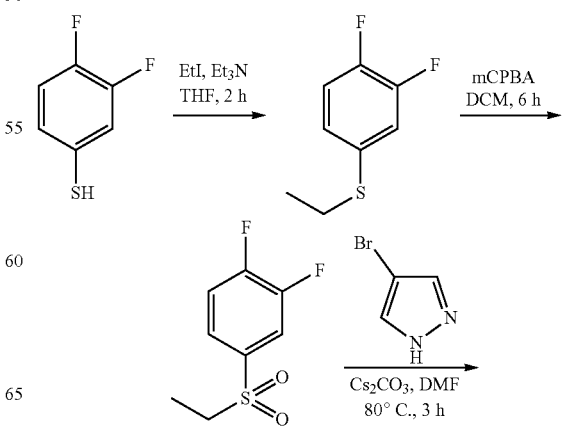

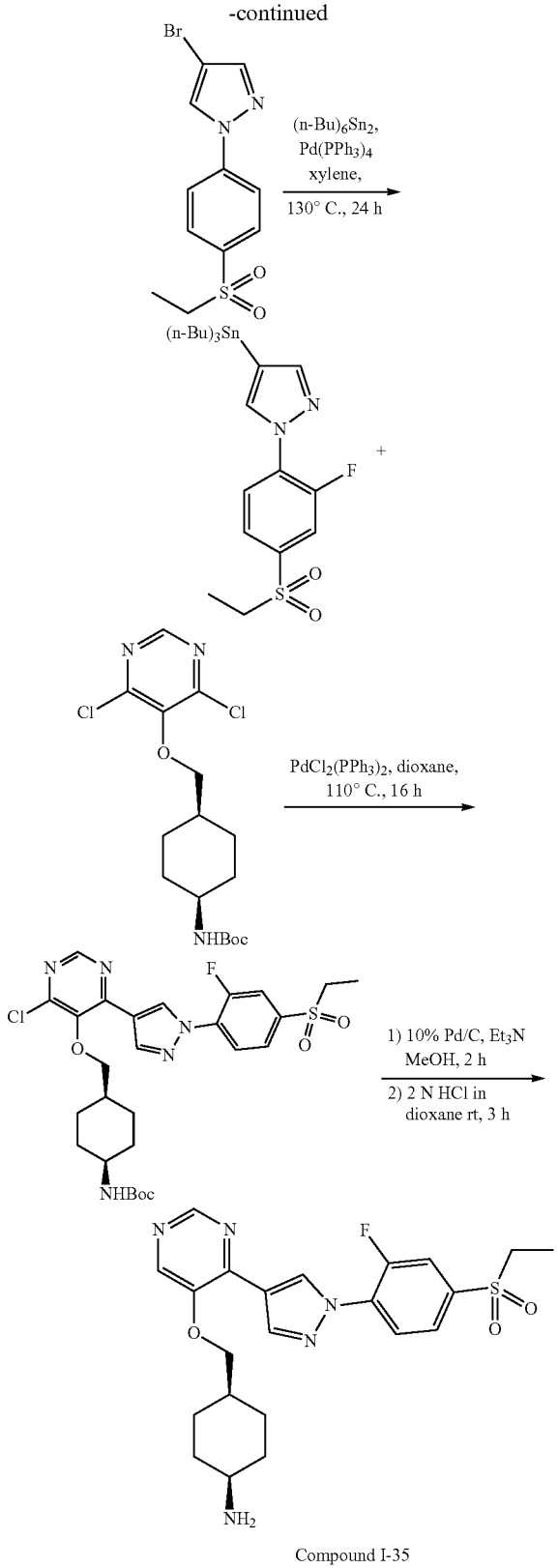

Compound I-35

To a solution of 3,4-difluorobenzenethiol (3 g, 20.5 mmol) and iodoethane (2.0 mL, 24.6 mmol) in tetrahydrofuran (30 mL) was added triethylamine (2.86 mL, 20.5 mmol). The resulting mixture was stirred at ambient temperature for 2 h and then filtered. The filtrate was concentrated, triturated with pentane, and dried in vacuoin vacuo to afford (3,4-difluorophenyl)(ethyl)sulfane (2.6 g, 73%).

GC-MS: Calculated 174.03 Observed m/z 174.1.

To a solution of (3,4-difluorophenyl)(ethyl)sulfane (2.6 g, 14.9 mmol) in dichlromethane (50 mL) was treated with 3-chloroperoxybenzoic acid (8.1 g, 32.8 mmol). The resulting mixture was stirred at ambient temperature for 6 h and then filtered. The filtrate was washed with saturated aqueous sodium bicarbonate solution, dried over anhydrous sodium sulfate, filtered, and concentrated. The residue was purified by silica gel column chromatography to obtain 4-(ethylsulfonyl)-1,2-difluorobenzene (3.0 g, 97.4%).

GC-MS: Calculated 206.02 Observed m/z 206.0.

To a solution of 4-(ethylsulfonyl)-1,2-difluorobenzene (2.5 g, 12.1 mmol) and 4-bromo-1H-pyrazole (1.77 g, 12.1 mmol) in DMF (20 mL) was added $Cs_2CO_3$ (11.8 g, 36.3 mmol) and the reaction heated at 80° C. for 3 h. The reaction mixture was cooled, treated with water and extracted with ethyl acetate (2×50 mL). The combined organic layers were washed with brine solution, dried over anhydrous sodium sulfate, filtered, and concentrated. The residue was purified by silica gel column chromatography to obtain 4-bromo-1-(4-(ethylsulfonyl)-2-fluorophenyl)-1H-pyrazole (2.3 g, 57%).

LC/MS: Calculated 331.96 Observed m/z [M+H]$^+$333.0.

To a solution of 4-bromo-1-(4-(ethylsulfonyl)-2-fluorophenyl)-1H-pyrazole (500 mg, 1.5 mmol) and (n-Bu)$_6$Sn$_2$ (2.62 g, 4.5 mmol) in xylene (10 mL) was added Pd(PPh$_3$)$_4$ (173 mg, 0.15 mmol) and heated at 130° C. for 24 h. The reaction mixture was filtered, evaporated and purified by silica gel column chromatography to furnish 1-(4-(ethylsulfonyl)-2-fluorophenyl)-4-(tributylstannyl)-1H-pyrazole (200 mg, 24.5%).

LC/MS: Calculated 544.16 Observed m/z [M+H]$^+$545.2.

To a degassed solution of tert-butyl ((1s, 4s)-4-(((4,6-dichloropyrimidin-5-yl)oxy)methyl)cyclohexyl)carbamate (125 mg, 0.33 mmol) and 1-(4-(ethylsulfonyl)-2-fluorophenyl)-4-(tributylstannyl)-1H-pyrazole (200 mg, 0.37 mmol) in dioxane (10 mL) was added PdCl$_2$(PPh$_3$)$_2$ (23.1 mg, 0.033 mmol) and the reaction mixture was heated at 110° C. for 16 h. The reaction mixture was filtered through celite bed and concentrated in vacuo. The crude compound was purified by silica gel column chromatography to obtain tert-butyl ((1s, 4s)-4-(((4-chloro-6-(1-(4-(ethylsulfonyl)-2-fluorophenyl)-1H-pyrazol-4-yl)pyrimidin-5-yl)oxy)methyl)cyclohexyl) carbamate 7 (150 mg, 76%).

LC/MS: Calculated 593.19 Observed m/z [M+H]$^+$494.1 (mass corresponding to a loss of BOC group).

To a solution of tert-butyl ((1s, 4s)-4-(((4-chloro-6-(1-(4-(ethylsulfonyl)-2-fluorophenyl)-1H-pyrazol-4-yl)pyrimidin-5-yl)oxy)methyl)cyclohexyl)carbamate 7 (130 mg, 0.22 mmol) in methanol (10 mL) was added triethylamine (89 mg, 0.88 mmol), followed by 10% Pd/carbon (260 mg) and the mixture was stirred under hydrogen atmosphere for 2 h. The reaction mixture was concentrated in vacuo and was purified by silica gel column chromatography to obtain tert-butyl ((1s, 4s)-4-(((4-(1-(4-(ethylsulfonyl)-2-fluorophenyl)-1H-pyrazol-4-yl)pyrimidin-5-yl)oxy)methyl)cyclohexyl)carbamate (70 mg, 57%).

LC/MS: Calculated 559.23 Observed m/z [M+H]$^+$460.1 (mass corresponding to a loss of BOC group).

To a solution of tert-butyl ((1s, 4s)-4-(((4-(1-(4-(ethylsulfonyl)-2-fluorophenyl)-1H-pyrazol-4-yl)pyrimidin-5-yl)oxy)methyl)cyclohexyl)carbamate (70 mg, 0.125 mmol) in 4 mL of dioxane was added 4 M HCl in dioxane (4.0 mL) and the reaction mixture was stirred at room temperature for 3 h. The reaction mixture was concentrated in vacuum and triturated with diethyl ether to give (1s, 4s)-4-(((4-(1-(4-(ethylsulfonyl)-2-fluorophenyl)-1H-pyrazol-4-yl)pyrimidin-5-yl)oxy)methyl)cyclohexan-1-amine hydrochloride salt as off white solid (Compound I-35; 60 mg, 96%).

LC/MS: Calculated 459.17 Observed m/z [M+H]$^+$460.1. HPLC (purity): 98.57%.

$^1$H-NMR (400 MHz, DMSO-d$_6$): δ 9.01 (d, J=2.8 Hz, 1H), 8.83 (s, 1H), 8.72 (s, 1H), 8.59 (s, 1H), 8.27 (t, J=8.0 Hz, 1H), 8.08 (dd, J=1.6 Hz, 11.2 Hz, 1H), 8.02 (brs, 3H), 7.92 (d, J=8.1 Hz, 1H), 4.23 (d, J=7.2 Hz, 2H), 3.34 (q, J=7.2 Hz, 2H), 3.29 (m, 1H), 2.17 (m, 1H), 1.75-1.72 (m, 8H), 1.16 (t, J=7.2 Hz, 3H).

Example 47

Formation of Exemplary Pharmaceutical Salts

Hydrochloric acid salts of the foregoing compounds are prepared by solubilizing a compound in a minimum amount of ethanol and a solution of ethanolic HCl 20% is added drop-wise while the mixture stirred for 1 hour followed by addition of diethyl ether. A precipitated off-white solid hydrochloride is separated by filtration, washed with diethyl ether and dried.

Additionally, salts can be prepared by reacting free acid or base forms of the compounds of the present disclosure with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in Remington's Pharmaceutical Sciences. 18$^{th}$ ed., Mack Publishing Company, Easton, Pa., 1990, p. 1445.

Example 48

Inhibition Assays

Experimental Procedures:

Kinase assays are performed at room temperature. Compounds are added 10-dose IC$_{50}$ mode into enzyme/substrate mixture using acoustic technology with 20 minute compound pre-incubation. Then 5 concentrations of ATP are added to initiate the reaction. The activity is monitored every 5-15 minutes for a time course study. The ATP, substrate, and compound concentrations tested are as follows:

ATP Competition Evaluation and K$_i$ Determination for Both MELK and FLT3:

ATP concentrations tested with 10, 30, 75, 150, and 300 µM ATP and the substrate concentration is constant at 20 µM. Compound concentrations tested for 10-dose IC$_{50}$ with 3-fold serial dilution start at 100 µM for test compounds. Time points are measured at 0, 5, 10, 15, 20, 30, 45, 60, 75, 90, 105, and 120 minutes.

The experiments are designed to obtain K$_m$ values for ATP in the presence of different concentrations of the inhibitor; ideally including at IC$_{25}$, IC$_{50}$, and IC$_{75}$. However, IC$_{50}$ values will be shifted if the compounds are ATP competitive inhibitors. Therefore, 10-dose IC$_{50}$ mode is taken to ensure covering the optimal concentration range. The 20 minute pre-incubation of compound and enzyme is performed to ensure the compound binding to the enzyme and equilibration. The reactions are monitored every 5-15 minutes to obtain progress curves with time course. At each time point, radioisotope signal ($^{33}$P) is converted into "µM phosphate transferred to substrate" and is plotted against time. The slopes of linear portion of progress curves are obtained by linear regression using Microsoft Excel. The slopes (or velocity; µM/min) are then plotted against ATP concentrations for Michaelis-Menten plot, and subsequent Lineweaver-Burk plot (double-reciprocal plot), using GraphPad Prism software. The results are further analyzed with global fit using GraFit software. The inhibition of MELK and FLT3 (ITD) by test compounds is not time-dependent and competitive with respect to ATP.

Example 49

General Protein Kinase Assay Methodology Employed for Selected Kinases

In vitro profiling of the MELK, MELK (T460M) kinase panel was performed at Reaction Biology Corporation using the "HotSpot" assay platform. In vitro profiling of the FLT3, FLT3 mutant forms; FLT3 (D835Y), FLT3 (F594R595insR), FLT3 (F594R595insREY), FLT3 (ITD), FLT3 (ITD)-NPOS, FLT3 (ITD)-W51 and FLT3 (R595_E596insEY) kinase panel is performed in the same manner.

Briefly, specific kinase/substrate pairs along with required cofactors were prepared in reaction buffer; 20 mM Hepes (pH 7.5), 10 mM MgCl$_2$, 1 mM EGTA, 0.02% Brij35, 0.02 mg/mL BSA, 0.1 mM Na$_3$VO$_4$, 2 mM DTT, 1% DMSO. Compounds were delivered into the reaction, followed ~20 min later by addition of a mixture of ATP (Sigma) and $^{33}$P ATP (PerkinElmer) to a final concentration of 10 M. Reactions were carried out at 25° C. for 120 min, followed by spotting of the reactions onto P81 ion exchange filter paper (Whatman). Unbound phosphate was removed by extensive washing of filters in 0.75% phosphoric acid. After subtraction of background derived from control reactions containing inactive enzyme, kinase activity data were expressed as the percent remaining kinase activity in test samples compared to vehicle (dimethyl sulfoxide) reactions. IC$_{50}$ values and curve fits were obtained using Prism (GraphPad Software).

TABLE 2

List of compounds IC$_{50}$ values (nM) for MELK and FLT3

| Compound | MELK | FLT3 |
|---|---|---|
| I-1 | +++ | +++ |
| I-2 | + | ++ |
| I-3 | ++ | ++ |
| I-4 | ++ | +++ |
| I-5 | +++ | +++ |
| I-6 | ++ | ++ |
| I-7 | ++ | ++ |
| I-8 | +++ | +++ |
| I-9 | ++ | +++ |
| I-10 | + | ++ |
| I-11 | + | ++ |
| I-12 | + | ++ |
| I-13 | + | + |
| I-14 | + | ++ |
| I-15 | ++ | +++ |
| I-16 | + | + |
| I-17 | ++ | ++ |
| I-18 | + | ++ |
| I-19 | +++ | +++ |
| I-20 | + | ++ |
| I-21 | +++ | +++ |
| I-22 | +++ | +++ |
| I-23 | +++ | +++ |
| I-24 | + | + |
| I-25 | +++ | +++ |
| I-26 | +++ | +++ |

TABLE 2-continued

List of compounds IC$_{50}$ values (nM) for MELK and FLT3

| Compound | MELK | FLT3 |
|---|---|---|
| I-27 | ++ | +++ |
| I-28 | ++ | ++ |
| I-29 | + | ++ |
| I-30 | ++ | ++ |
| I-31 | + | ++ |
| I-32 | +++ | +++ |
| I-33 | +++ | +++ |
| I-34 | ++ | +++ |
| I-35 | ++ | ++ |

+ denotes an IC$_{50}$ value greater than 1,000 nM
++ denotes an IC$_{50}$ value from 200 to 1,000 nM
+++ denotes an IC$_{50}$ value up to 200 nM
— indicates no data Example 50

Cancer Cell Efficacy Study

The effect of compounds of structure (I) on cancer cell lines from different cancers is tested in order to determine the ability of the compound to affect the growth of cell lines from different tissue origins. This study is conducted on Oncolead GmbH cancer cell line test system on a broader disease panel and multiple hematological cell lines. Cell lines are purchased by Oncolead directly from the ATCC, NCI, CLS and DSMZ cell line collections. A master bank and working aliquots are prepared from these cell lines, and cells used for the study have undergone less than 20 passages. To ensure the absence of potential contamination or wrong assignment, all cell lines are tested by STR analysis. Absence of mycoplasma and SMRV contamination is confirmed for all cell lines used in the studies. In addition, all studies include a set of 6 reference agents—paclitaxel, 5-FU, SN-38 (an active metabolite of irinotecan), sorafenib, geldanamycin, and doxorubicin—to ensure reproducible responses of cell lines and provide a control for day-to-day experimental variations. 82 cell lines are tested in parallel. The test concentration ranges represent 6 data points as a 10-fold dilution. Each experiment is performed in duplicates arranged in different micro-titre plates and using independent compound dilutions. The experimental set-up allows minimization of systematic errors and accounts for variations within experiments.

The most sensitive and resistant cell lines are visualized either by using a box-plot graph or by selecting the 8 most and least sensitive cell lines using the z-score for each agent. This also applies to the cell lines where activity of a test compound against panel of cancer cell lines against Z-Score sensitivity and resistant readouts. The specific AML cancer cell line MV4-11 in this profiling assay is sensitive and few of the hematological cancer lines are sensitive to test compound is observed.

Example 51

In Vivo Models of AML

To assess the anti-tumor efficacy of compounds of structure (I) in MV4-11 (ATCC CRL-9591) human biphenotypic B myelomonocytic leukemia (lymphoblast) cell line xenograft in female SCID-Beige mice, MV4-11 (ATCC CRL-9591cell line obtained from ATCC, is propagated in cell culture, RPMI+10% Fetal Calf Serum.

Experimental Design:

MV4-11 cells are harvested while in logarithmic growth and implanted subcutaneously (5×10$^6$ cells) in the flank of mice. Tumor growth is monitored daily, and when tumors reach 100-120 mm$^3$, mice are randomized to 3 groups of 8 mice per group and compounds are dosed using a positive control (Pacritinib) and negative control (vehicle only) and a vehicle including 10% PG, 25% Solutol in WFI and 65% PBS. All groups are dosed once per day orally at a dosage volume of 10 mL per Kg.

TABLE 3

Dosing parameters for in vivo xenograft model

| Groups | Formulation vehicle | Dose (mg/Kg) |
|---|---|---|
| G1: Vehicle | 10% PG + 25% Solutol in WFI + 65% PBS | — |
| G2: Compound of Structure (I) | 10% PG + 25% Solutol in WFI + 65% PBS | 50 |
| G3: Pacritinib | 10% PG + 25% Solutol in WFI + 65% PBS | 50 |

Animals are terminated when tumors reach 2000 mm$^3$, 10% of body weight, or develop ulceration and necrosis. Upon termination, tumors tissue is dissected, and flash frozen in liquid nitrogen and samples stored at −80° C. until shipped to sponsor. The tumor volume is measured by digital Vernier calipers by using formula as follows:

(smallest diameter$^2$)×largest diameter/2

Body weight is monitored daily and tumor volume is measured three times a week. Plasma samples are collected at 1, 2, 4 & 6 hour for bioanalysis and PK/PD correlation studies just before the termination of the study. Four animals in group 2 test compound treated animals are left over without sacrificing for observation post-completion of 33 days dosing.

All of the U.S. patents, U.S. patent application publications, U.S. patent applications, foreign patents, foreign patent applications and non-patent publications referred to in this specification or the attached Application Data Sheet, such as U.S. 62/751,405, are incorporated herein by reference, in their entirety to the extent not inconsistent with the present description.

From the foregoing it will be appreciated that, although specific embodiments of the disclosure have been described herein for purposes of illustration, various modifications may be made without deviating from the spirit and scope of the invention. Accordingly, the disclosure is not limited except as by the appended claims.

The invention claimed is:

1. A compound having structure (I):

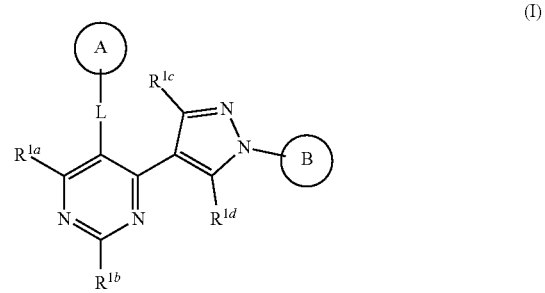

or a pharmaceutically acceptable salt or stereoisomer thereof, wherein:

Ring A is cycloalkyl or heterocyclyl, wherein the cycloalkyl and heterocyclyl are optionally substituted with one or more substituents independently selected from the group consisting of oxo, halo, CN, alkyl, haloalkyl, alkylNR$_g$R$_h$, CH$_2$S(O)$_2$R$_h$, CH$_2$S(O)$_2$NR$_g$R$_h$, C(NR$_g$)R$_h$, C(NN(R$_g$)$_2$)R$_h$, C(NOR$_g$)R$_h$, C(O)R$_g$, C(O)NR$_g$R$_h$, C(O)OR$_g$, NR$_g$R$_h$, NR$_g$C(O)R$_h$, NR$_g$C(O)NR$_g$R$_h$, NR$_g$C(O)OR$_h$, NR$_g$S(O)$_2$R$_h$, (=N)S(O)$_2$R$_g$, OR$_g$, OC(O)NR$_g$R$_h$, OS(O)$_2$R$_g$, SR$_g$, S(O)R$_g$, S(O)$_2$R$_g$, S(O)$_2$NR$_g$R$_h$, S(O)$_2$OR$_g$, Si(R$_g$)$_3$, cycloalkyl, heterocyclyl, and aryl;

Ring B is aryl, wherein the aryl is optionally substituted with one or more substituents independently selected from the group consisting of halo, CN, alkyl, haloalkyl, alkylNR$_g$R$_h$, CH$_2$S(O)$_2$R$_g$, CH$_2$S(O)$_2$NR$_g$R$_h$, C(NR$_g$)R$_h$, C(NN(R$_g$)$_2$)R$_h$, C(NOR$_R$)R$_h$, C(O)R$_g$, C(O)NR$_g$R$_h$, C(O)OR$_g$, NR$_g$R$_h$, NR$_g$C(O)R$_h$, NR$_g$C(O)NR$_g$R$_h$, NR$_g$C(O)OR$_h$, NR$_g$S(O)$_2$R$_h$, (=N)S(O)$_2$ R$_g$, OR$_g$, OC(O)NR$_g$R$_h$, OS(O)$_2$R$_g$, SR$_g$, S(O)R$_g$, S(O)$_2$R$_g$, S(O)$_2$NR$_g$R$_h$, S(O)$_2$OR$_g$, Si(R$_g$)$_3$, cycloalkyl, heterocyclyl, and aryl, and further wherein the heterocyclyl substituent is optionally substituted with one or more independently selected alkyl substituents;

L is a direct bond, alkylene, NR$^2$CHR$^2$—, —NR$^2$CHR$^2$CHR$^2$—, —OCHR$^2$—, or —OCHR$^2$CR$^2$—;

each R$_g$ is independently H, alkyl, haloalkyl, (aminyl)alkyl, O(alkyl), cycloalkyl, heterocyclyl, or aryl;

each R$_h$ is independently H, alkyl, haloalkyl, (aminyl)alkyl, O(alkyl), cycloalkyl, heterocyclyl, or aryl;

R$^{1a}$ is H, halo, C$_1$-C$_6$ alkyl, C$_2$-C$_6$ alkenyl, or C$_2$-C$_6$ alkynyl;

R$^{1b}$ is H, halo, C$_1$-C$_6$ alkyl, C$_2$-C$_6$ alkenyl, or C$_2$-C$_6$ alkynyl;

R$^{1c}$ is H, halo, C$_1$-C$_6$ alkyl, C$_2$-C$_6$ alkenyl, or C$_2$-C$_6$ alkynyl;

R$^{1d}$ is H, halo, C$_1$-C$_6$ alkyl, C$_2$-C$_6$ alkenyl, or C$_2$-C$_6$ alkynyl; and each R$^2$ is independently H or C$_1$-C$_6$ alkyl.

2. The compound of claim 1, or a pharmaceutically acceptable salt or stereoisomer thereof, wherein the compound is a pharmaceutically acceptable salt thereof.

3. The compound of claim 1, or a pharmaceutically acceptable salt or stereoisomer thereof, wherein the compound is a stereoisomer thereof.

4. The compound of claim 1, or a pharmaceutically acceptable salt or stereoisomer thereof, wherein Ring A is optionally substituted cyclobutyl, optionally substituted cyclopentyl, or optionally substituted cyclohexyl.

5. The compound of claim 1, or a pharmaceutically acceptable salt or stereoisomer thereof, wherein Ring A is optionally substituted piperidinyl.

6. The compound of claim 1, or a pharmaceutically acceptable salt of stereoisomer thereof, wherein Ring A is substituted with one or more substituents independently selected from the group consisting of C$_1$-C$_6$ alkyl, alkylNH$_2$, alkylNH(alkyl), NH$_2$, NH(alkyl) and OH.

7. The compound of claim 1, or a pharmaceutically acceptable salt or stereoisomer thereof, wherein Ring A is:

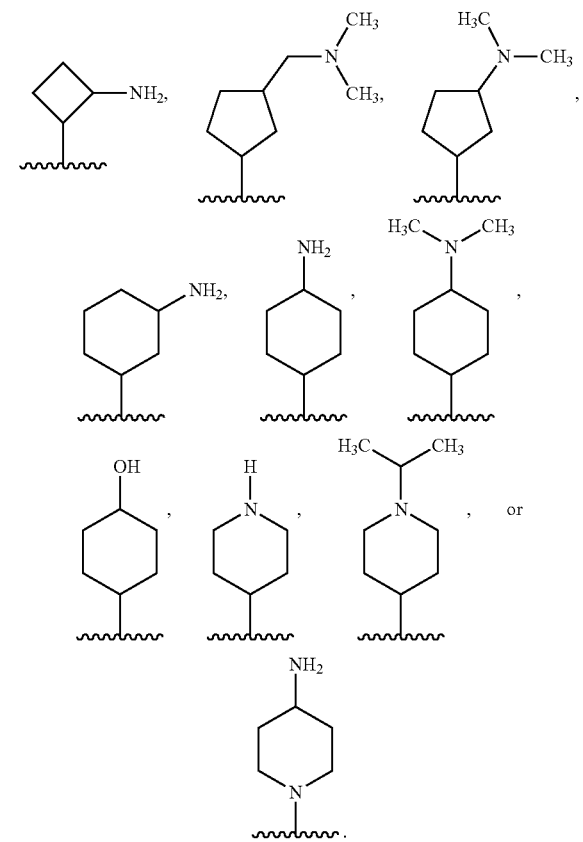

8. The compound of claim 1, or a pharmaceutically acceptable salt or stereoisomer thereof, wherein Ring B is optionally substituted phenyl.

9. The compound of claim 1, or a pharmaceutically acceptable salt or stereoisomer thereof, wherein Ring B is substituted with one or more substituents independently selected from the group consisting of halo, CN, C$_1$-C$_6$ alkyl, haloalkyl, OH, O(alkyl), O(haloalkyl), S(O)$_2$alkyl, and heterocyclyl.

10. The compound of claim 1, or a pharmaceutically acceptable salt or stereoisomer thereof, wherein Ring B is substituted with ne or more substituents independently selected from F, CN, CH$_3$, OH, OCH$_3$, OCF$_3$, S(O)$_2$CH$_2$CH$_3$, N-methylpiperazinyl, and morpholinyl.

11. The compound of claim 1, or a pharmaceutically acceptable salt or stereoisomer thereof, wherein Ring B is:

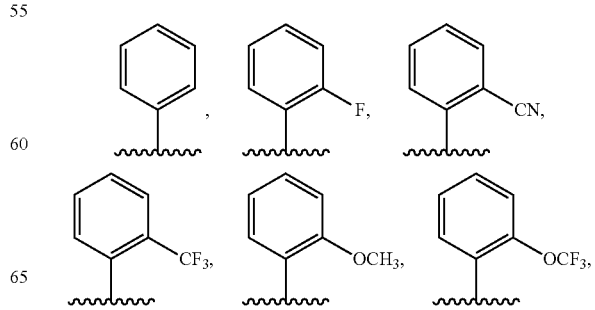

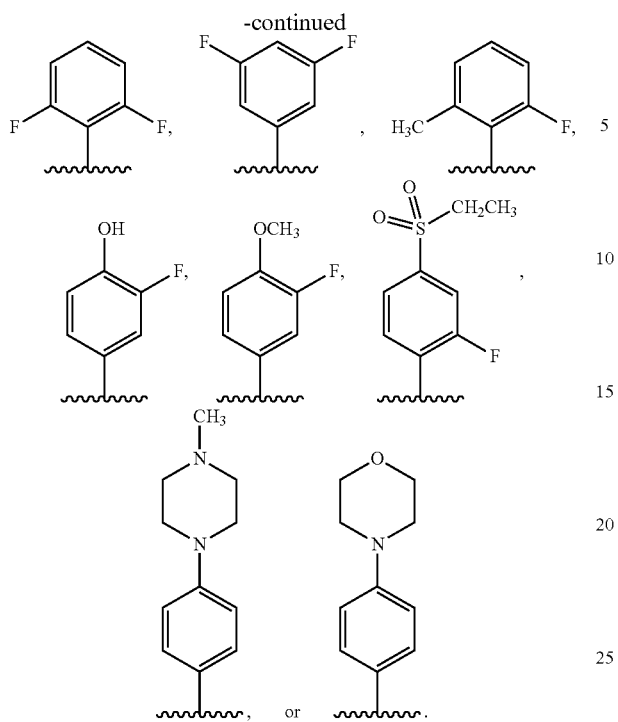

12. The compound of claim 1, or a pharmaceutically acceptable salt or stereoisomer thereof, wherein L is a direct bond, —NR²CR²—, —NR²CHR²CHR²—, —OCHR²—, or —OCHR²CHR²—.

13. The compound of 12, or a pharmaceutically acceptable salt or stereoisomer thereof, wherein L is —NR²CHR²—, —NR²CHR²CHR²—, —OCHR²—, or —OCHR²CHR²—.

14. The compound of claim 1, or a pharmaceutically acceptable salt or stereoisomer thereof, wherein
$R^{1a}$ is H; and
$R^{1b}$ is H.

15. The compound of claim 1, or a pharmaceutically acceptable salt or stereoisomer thereof, wherein:
$R^{1c}$ is H; and
$R^{1d}$ is H.

16. The compound of claim 1, or a pharmaceutically acceptable salt or stereoisomer thereof, wherein
$R^{1a}$ is H or halo;
$R^{1b}$ is H or halo;
$R^{1c}$ is H or halo; and
$R^{1d}$ is H or halo.

17. The compound of claim 1, wherein the compound has structures (Ia), structure (Ib), structure (Ic), or structure (Id):

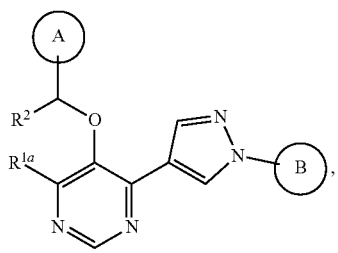

(Ia)

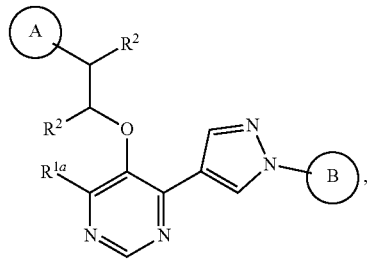

(Ib)

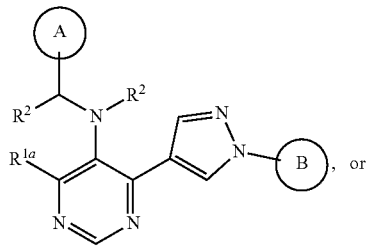

(Ic)

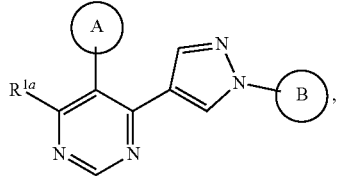

(Id)

or a pharmaceutically acceptable salt of stereoisomer thereof,
wherein:
$R^{1a}$ is H or halo; and
each $R^2$ is independently H or $CH_3$.

18. The compound of claim 1, wherein the compound is selected from the group consisting of:

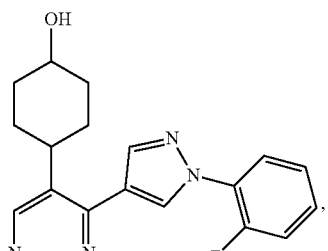

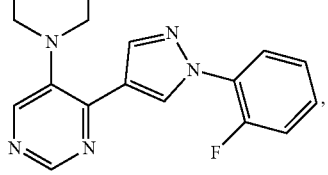

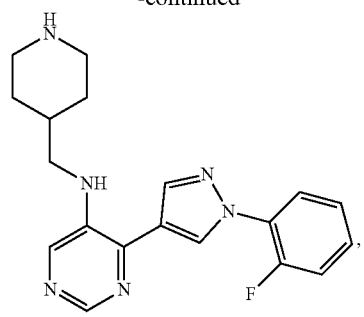
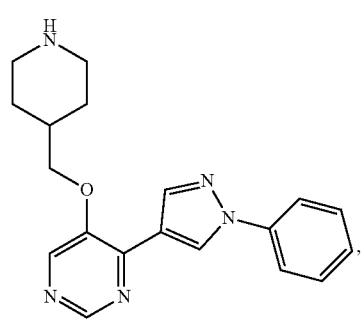
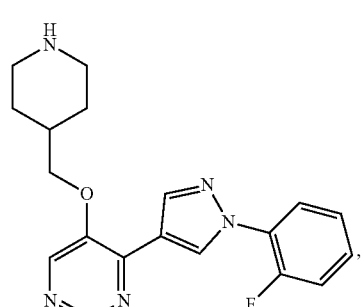
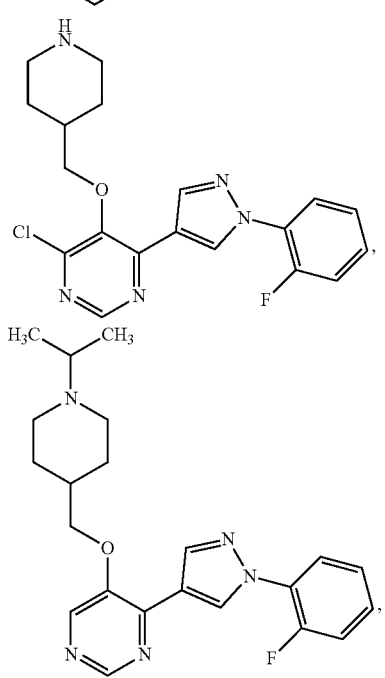
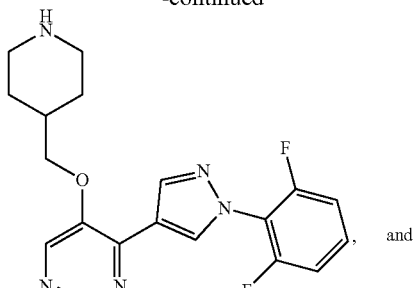
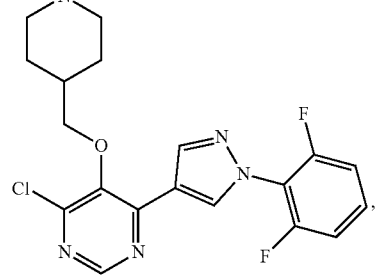
and
or a pharmaceutically acceptable salt thereof.
19. The compound of claim 1, or a stereoisomer thereof, wherein the stereoisomer of the compound is selected from the group consisting of:
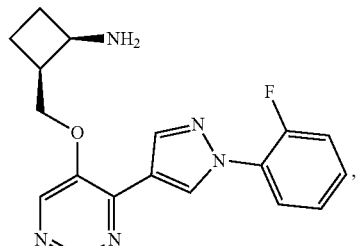
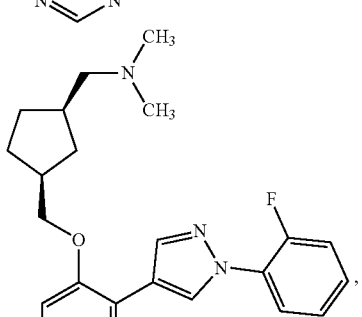
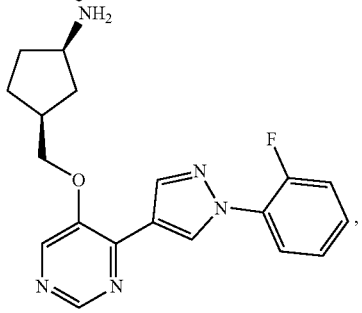

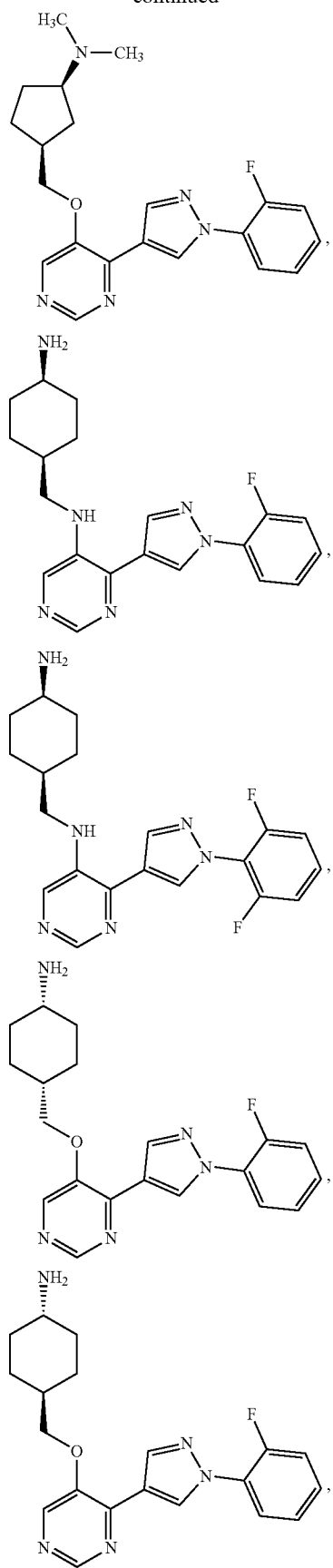
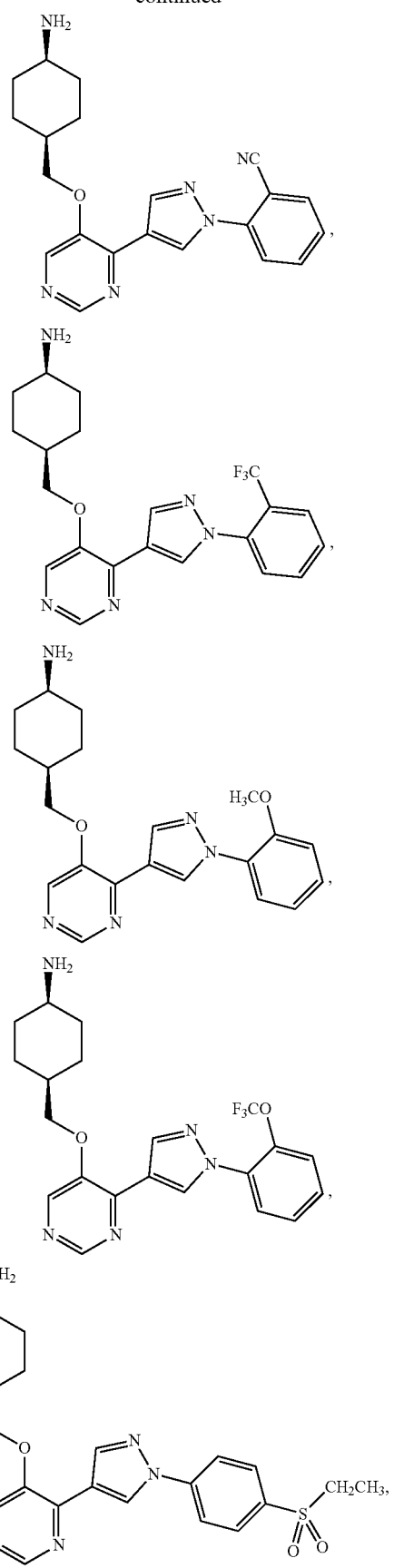

133
-continued
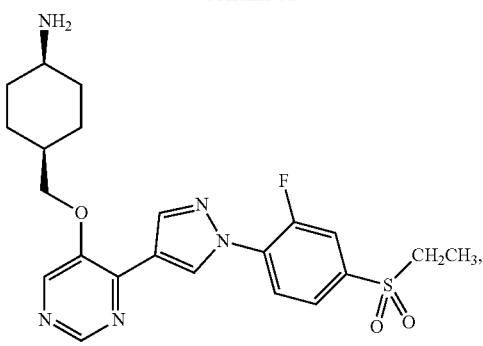
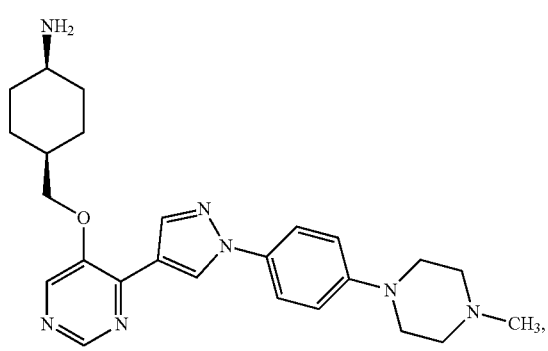
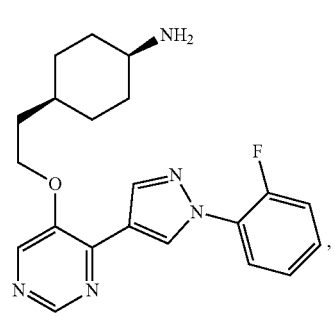
134
-continued
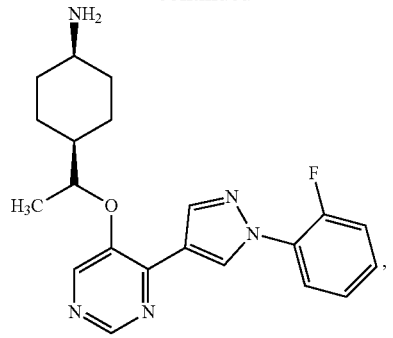
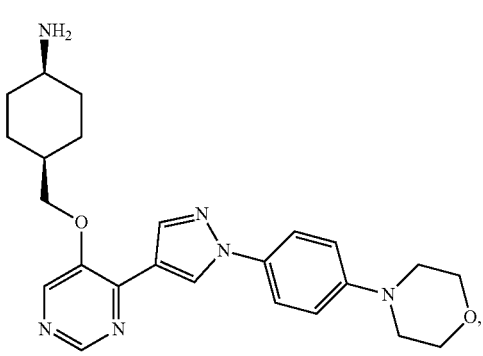
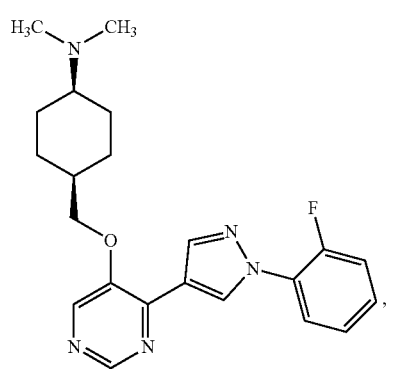
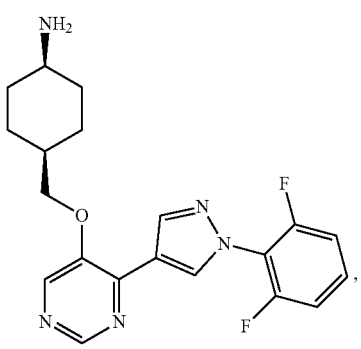

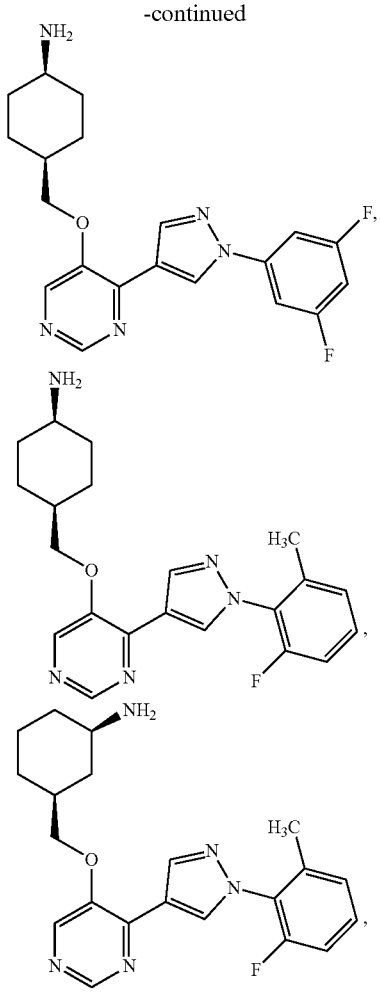

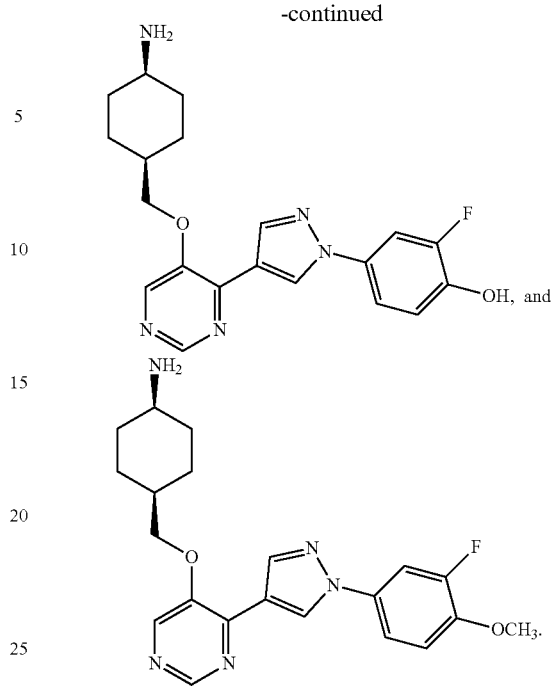

20. A pharmaceutical composition comprising a pharmaceutically acceptable carrier and a compound of claim 1, or a pharmaceutically acceptable salt or stereoisomer thereof.

21. A method for inhibiting maternal embryonic leucine zipper kinase activity in a subject, wherein the method comprises administering to the subject in need thereof a therapeutically effective amount of the pharmaceutical composition of claim 20.

22. The method of claim 21, wherein the subject has cancer.

* * * * *

UNITED STATES PATENT AND TRADEMARK OFFICE
CERTIFICATE OF CORRECTION

PATENT NO. : 11,053,221 B2
APPLICATION NO. : 16/664649
DATED : July 6, 2021
INVENTOR(S) : Hariprasad Vankayalapati Page 1 of 1

It is certified that error appears in the above-identified patent and that said Letters Patent is hereby corrected as shown below:

On the Title Page

Item (57) Abstract:
" , and  and are as defined herein." should read: -- , and  are as defined herein. --.

In the Claims

Column 125, Claim 1, Line 28:
"alkylene, NR2CHR2–," should read: -- alkylene, –NR2CHR2–, --.

Column 126, Claim 10, Line 48:
"with ne or" should read: -- with one or --.

Column 127, Claim 12, Line 32:
"bond, –NR2CR2–," should read: -- bond, –NR2CHR2–, --.

Column 127, Claim 17, Line 54:
"structures (Ia)," should read: -- structure (Ia), --.

Signed and Sealed this
Nineteenth Day of July, 2022

Katherine Kelly Vidal
*Director of the United States Patent and Trademark Office*